(12) United States Patent
Li et al.

(10) Patent No.: US 10,052,340 B2
(45) Date of Patent: Aug. 21, 2018

(54) USE OF IVERMECTIN AND DERIVATIVES THEREOF

(71) Applicant: XIAMEN UNIVERSITY, Xiamen, Fujian (CN)

(72) Inventors: Yong Li, Xiamen (CN); Lihua Jin, Xiamen (CN); Xuhui Feng, Xiamen (CN)

(73) Assignee: XIAMEN UNIVERSITY, Xiamen (CN)

( * ) Notice: Subject to any disclaimer, the term of this patent is extended or adjusted under 35 U.S.C. 154(b) by 35 days.

(21) Appl. No.: 14/436,836

(22) PCT Filed: Jun. 24, 2013

(86) PCT No.: PCT/CN2013/077796
§ 371 (c)(1),
(2) Date: Apr. 17, 2015

(87) PCT Pub. No.: WO2014/059797
PCT Pub. Date: Apr. 24, 2014

(65) Prior Publication Data
US 2015/0306123 A1   Oct. 29, 2015

(30) Foreign Application Priority Data
Oct. 19, 2012  (CN) .......................... 2012 1 0403320

(51) Int. Cl.
*A61K 31/7048*   (2006.01)
(52) U.S. Cl.
CPC ............................... *A61K 31/7048* (2013.01)
(58) Field of Classification Search
None
See application file for complete search history.

(56) References Cited

U.S. PATENT DOCUMENTS 4,199,569 A * 4/1980 Chabala ................. A01N 43/90
514/30
5,248,669 A * 9/1993 Amer ..................... A61K 31/70
455/62

FOREIGN PATENT DOCUMENTS

| CN | 102872066 | | 1/2013 | | |
|---|---|---|---|---|---|
| EP | 0214731 B1 | * | 1/1991 | ............. | A01N 43/90 |
| WO | WO 2004/006906 A2 | * | 1/2004 | .......... | A61K 31/165 |
| WO | WO 2004/093886 A1 | | 11/2004 | | |
| WO | WO 2005/089806 A1 | | 9/2005 | | |
| WO | WO 2008/034202 A2 | | 3/2008 | | |
| WO | WO 2011/011632 A1 | | 1/2011 | | |

OTHER PUBLICATIONS

Lichtenberger, P. et al., Transplant Infectious Disease, "Hyperinfection strongyloidiasis in a liver transplant recipient treated with parenteral ivermectin", 2009, vol. 11, pp. 137-142 (Year: 2009).*
English Translation of the International Preliminary Report on Patentability and Written Opinion of the International Searching Authority dated Sep. 26, 2013 from counterpart foreign application PCT/CN2013/077796.

* cited by examiner

*Primary Examiner* — Shaojia A Jiang
*Assistant Examiner* — Bahar Craigo
(74) *Attorney, Agent, or Firm* — Rabin & Berdo, P.C.

(57) ABSTRACT

The present invention relates to the new use of antiparasitic agents, such as ivermectin, abamectin/avermectin, doramectin and so on, and the design method of the derivatives for the new use. The said compounds including macrolide abamectin/avermectin, ivermectin, doramectin and the derivatives thereof, may be used in the manufacture of a medicament for use in treating metabolic related diseases in a mammal, such as hyperglycemia, insulin resistance, hypertriglyceridemia, hypercholesterolemia, diabetes, obesity, etc, and Farnesoid X receptor mediated diseases, such as cholestasia, gallstone, non alcohol fatty liver disease, atherosclerosis, inflammation, cancer, etc.

3 Claims, 7 Drawing Sheets

USE OF IVERMECTIN AND DERIVATIVES THEREOF

CROSS-REFERENCE TO RELATED APPLICATIONS

This application is a National Stage filing under 35 U.S.C. § 371 of International Patent Application No. PCT/CN2013/077796, filed on Jun. 24, 2013, entitled "Use of Ivermectin and Derivatives Thereof", which claims the benefit of and priority to Chinese Application No. 201210403320.2, filed on Oct. 19, 2012, entitled "Use of Ivermectin and Derivatives Thereof", which are incorporated by reference in their entireties.

TECHNICAL FIELD

The present invention relates to a new use of new effective ligands, such as ivermectin, doramectin, and abamectin/avermectin and the derivatives thereof, of Farnesoid X receptor (FXR), relative to antiparasitic agents, and a method for designing and optimizing the derivatives for the new use.

BACKGROUND ART

A nuclear receptor is a ligand-activated transcription factor. FXR is a very important member of nuclear receptors in humans, which plays an important regulating role in serious diseases of metabolism, inflammation, tumor, etc. and in the relevant physiological function. The FXR ligand mediated pharmacological action principle is that a ligand binds to the ligand binding domain (LBD) of FXR, thereby recruiting various coactivators (or corepressors) to regulate downstream target genes. In the body, bile acid is an endogenous ligand of FXR, the activation of FXR can maintain normal circulation and homeostasis of bile acid in the liver and small intestine, and can meanwhile regulate the levels of saccharides, lipids and cholesterol. FXR is involved in many signal pathways associated with metabolism, and has become a remarkable target molecule of a medicament for treating metabolic diseases such as hyperglycemia, insulin resistance, hypertriglyceridemia, hypercholesterolemia, diabetes, obesity, cholestasia, gallstones, non-alcoholic fatty liver, and atherosclerosis. Recently it has been found that FXR can regulate the regeneration of the liver, and the knockout of the FXR gene in a mouse can result in the development of liver cancer. Chenodeoxycholic acid (abbreviated as CDCA) is a type of bile acid which can bind to and activate FXR and can be used for treating gallstones. Among the ligands capable of binding to FXR, CDCA is the only medicament which is used clinically. However, the affinity of CDCA to FXR is far lower than that of synthetic ligand GW4064 of FXR, furthermore CDCA can also bind to bile acid binding protein (I-BABP), bile acid transporter and other proteins; therefore, CDCA is also not a medicament specifically targeting FXR. About 13% of the existing medicaments target nuclear receptors, and based on the important physiological action regulated by FXR, screening new ligand medicaments targeting FXR and optimizing, designing and developing the ligand medicaments have an important application value.

Ivermectin and doramectin are derivatives of macrolide abamectin/avermectin produced by streptomycetes, and have a highly effective and broad-spectrum antiparasitic effect, wherein ivermectin, doramectin and abamectin/avermectin are mainly used in controlling livestock parasites and treating filarial infection in humans. There are reports which had suggested that the targets of ivermectin in invertebrates are receptors such as γ-aminobutyric acid (GABA) receptor and glutamic acid mediated chloride ion channel receptor (GluClR). There is no report that there is a target of abamectin/avermectin and its derivatives with high-affinity and specificity in a mammal as of yet.

CONTENTS OF THE INVENTION

The present invention aims to provide a use of ivermectin, abamectin/avermectin and doramectin and the derivatives thereof.

Said ivermectin (indicated as structural formula I) is a derivative of macrolide abamectin/avermectin produced by streptomycetes, has a highly effective and broad-spectrum antiparasitic effect, and is mainly used in controlling livestock parasites and treating filarial infection in humans.

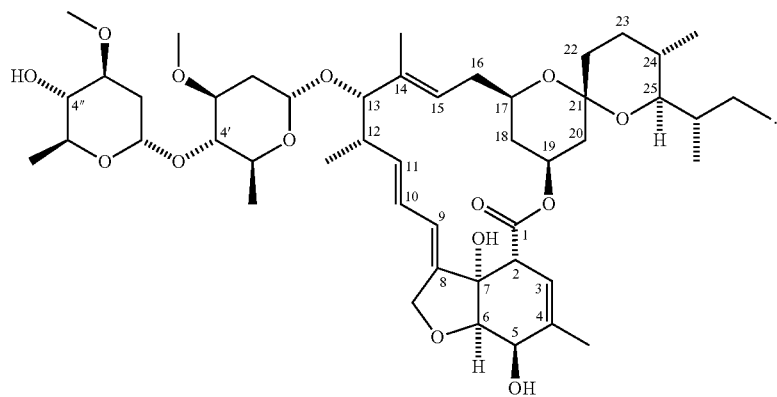

Structural formula I

Said ivermectin has a new function which is totally different from the antiparasitic effect. The function is characterized in that it is firstly proposed that Farnesoid X receptor is a target protein to which ivermectin binds specifically in a mammal. Ivermectin specifically binds to Farnesoid X receptor (FXR) with high affinity, regulates the metabolism of saccharides, lipids and cholesterol in serum of a mammal, effectively decreases the levels of saccharides, lipids and cholesterol in serum of a diabetes animal model, and improves the corresponding symptoms. Ivermectin can also inhibit inflammatory response through the mediation of Farnesoid X receptor. Therefore, ivermectin and its derivatives have a good application prospect in preparing a medicament for treating metabolism associated diseases in a mammal, such as hyperglycemia, insulin resistance, hypertriglyceridemia, hypercholesterolemia, diabetes and obesity, and Farnesoid X receptor mediated diseases, such as cholestasia, gallstones, non-alcoholic fatty liver, atherosclerosis, inflammation and cancer.

Said derivatives or analogs of ivermectin, such as abamectin/avermectin (structural formula II) and doramectin (structural formula III), have properties and use similar to ivermectin.

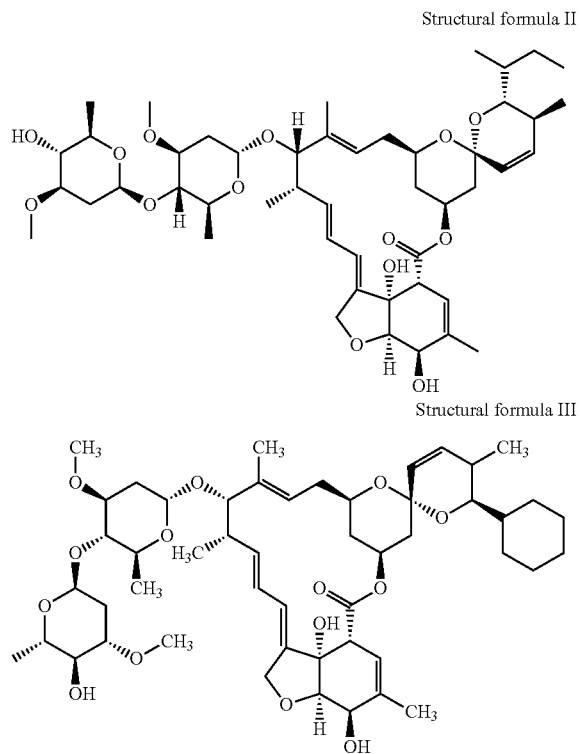

Structural formula II

Structural formula III

Abamectin/avermectin has a double bond at position C22-C23 in the structural formula of ivermectin. We find that abamectin/avermectin can specifically bind to FXR with high affinity, is also a ligand of FXR, and can effectively decrease the levels of saccharides, lipids and cholesterol in sera of mice fed with high-fat diet, and the weight of the epididymal fat pad. Therefore, abamectin/avermectin has a new use for treating metabolism associated diseases in a mammal, such as hyperglycemia, insulin resistance, hypertriglyceridemia, hypercholesterolemia, diabetes and obesity, and Farnesoid X receptor mediated diseases, such as cholestasia, gallstones, non-alcoholic fatty liver, atherosclerosis, inflammation and cancer.

Doramectin has a double bond at position C22-C23 in the structural formula of ivermectin, wherein position C25 is substituted at the side chain of a benzene ring. We find that doramectin can specifically bind to FXR with high affinity, is also a ligand of FXR, and can effectively decrease the levels of saccharides, lipids and cholesterol in sera of mice fed with high-fat diet, and the weight of the epididymal fat pad. Therefore, doramectin has the new use for treating metabolism associated diseases in a mammal, such as hyperglycemia, insulin resistance, hypertriglyceridemia, hypercholesterolemia, diabetes and obesity, and Farnesoid X receptor mediated diseases, such as cholestasia, gallstones, non-alcoholic fatty liver, atherosclerosis, inflammation and cancer.

As claimed in the structures and functions of abamectin/avermectin, ivermectin, and the derivative doramectin, it can be presumed that other structural analogs or derivatives of abamectin/avermectin and ivermectin, which can bind to FXR, may also have similar functions and use.

For more than twenty years, abamectin/avermectin, ivermectin and the derivatives thereof have mainly been used in controlling livestock parasites and treating filarial infection in humans, the mechanism of action is that they selectively bind to glutamic acid mediated chloride ion channel receptors in nerve and muscle cells of an invertebrate, and interrupt the transmission of nerve impulses to a muscle cell, thereby resulting in the parasite being fatally paralyzed, or expelled from the body. Ivermectin and its derivatives can also bind to γ-aminobutyric acid receptors and play the same role. However, there is no report which has suggested the presence of glutamic acid mediated chloride ion channel receptors in a mammal, γ-aminobutyric acid receptors in a mammal are present merely in the central nervous system, while mammals have the blood brain barrier and can effectively prevent abamectin/avermectin, ivermectin and the derivatives thereof arriving at the central nervous system; therefore, in a normal case, abamectin/avermectin, ivermectin and the derivatives thereof have a high safety factor in the mammal. Since abamectin/avermectin, ivermectin and the derivatives thereof have been applied clinically in humans for more than twenty years, the safety in humans has been assured, and the present invention finds that abamectin/avermectin, ivermectin and the derivatives thereof can effectively regulate the metabolism of saccharides, lipids and cholesterol in serum of a mammal, effectively decreasing the levels of saccharides, insulin, triglycerides and cholesterol in serum of an animal model, suggesting that abamectin/avermectin, ivermectin and the derivatives thereof have a good prospect in treating Farnesoid X receptor mediated diseases associated with for example glycometabolism and lipid metabolism.

The present invention sufficiently demonstrates the novelty, safety, effectiveness, high drug production, low cost, and great social value and economic benefit of abamectin/avermectin, ivermectin and the derivatives thereof in treating Farnesoid X receptor mediated relevant diseases such as metabolic diseases in a mammal. In addition, the present invention provides a unique structural pattern of binding of ivermectin to Farnesoid X receptor at the atomic level through x-ray crystal diffraction, and provides the ligand drug design targeting Farnesoid X receptor with safe leading drug small molecules and drug optimization structure templates and a design method.

In accordance with the three-dimensional crystal structural pattern where Farnesoid X receptor binds with ivermectin (Appendix 1), using the structural formula (for example structural formula I) of ivermectin as the structural basis, methods of drug designing, drug synthesizing and drug screening are performed in the following specific steps: using the structural formula I as the structural basis, carbon-carbon double bonds of C3-C4, C8-C9, C10-C11 and C14-C15 in the structural formula are modified; hydroxyl groups at positions C5, C7 and C4" are modified; side chains at positions C4, C12, C14, C24 and C25 are modified; and the glycosyl at position C13 is hydrolyzed and other groups are modified such as through substitution. The above methods are characterized in that any single modification and a combination of various modifications mentioned above can be used for preparing and treating metabolism associated diseases in a mammal, such as hyperglycemia, insulin resistance, hypertriglyceridemia, hypercholesterolemia, diabetes and obesity, and Farnesoid X receptor mediated diseases, such as cholestasia, gallstones, non-alcoholic fatty liver, atherosclerosis, inflammation and cancer.

The Technical Solutions of the Present Invention

Antiparasitic agents ivermectin, abamectin/avermectin and doramectin, obtained from high throughput screening, are specific ligands of FXR.

Based on the luciferase reporter gene activity analysis in in vitro transfection experiment, the selective recognition between the receptor and the ligands at a molecular structural level is indicated; the expression of the relevant target genes and the regulation state of the relevant signal pathways after the treatment with ivermectin are detected through primary culture of liver cells of a mouse in a mouse model, and the effects on the downstream signal pathways are indicated; the changes in various biochemical indices in the mouse model treated with abamectin/avermectin, ivermectin and doramectin are detected, so as to indicate the pathogenic molecular mechanism in connection with the changes in the corresponding signal pathways; and a diabetes and obesity mouse model is treated with medicaments abamectin/avermectin, ivermectin and doramectin, so as to determine the efficacy of such medicaments in treating diseases in a mammal, such as hyperglycemia, insulin resistance, hypertriglyceridemia, hypercholesterolemia, diabetes and obesity, and the use for treating Farnesoid X receptor mediated diseases associated with metabolism, such as cholestasia, gallstones, non-alcoholic fatty liver, and atherosclerosis. The use of ivermectin in treating inflammatory response is determined through regulating inflammatory response target genes.

In the same manner, wild-type mice and FXR knockout mice both fed with high-fat diet are respectively treated by injection of abamectin/avermectin, ivermectin and doramectin, and it is found that these derivatives can effectively decrease the epididymal fat pad/body weight ratio and the levels of glucose, triglycerides and cholesterol in sera in the wild-type mice. Therefore, it can be determined that the use of abamectin/avermectin, ivermectin and doramectin in treating diseases in a mammal, such as hyperglycemia, insulin resistance, hypertriglyceridemia, hypercholesterolemia, diabetes and obesity, and Farnesoid X receptor mediated diseases associated with metabolism, such as cholestasia, gallstones, non-alcoholic fatty liver, atherosclerosis is achieved through FXR.

FXR and ivermectin are prepared as a complex, and crystallization, x-ray crystal diffraction and structural resolution are performed on the complex by means of crystallography, thereby indicating the unique binding pattern of FXR to ivermectin at the atomic level, and providing the design of the therapeutic medicaments targeting FXR for the above diseases in a mammal with safe leading drug small molecules and the drug design and synthesis method of derivatives with the molecular structures as a template.

PARTICULAR EMBODIMENTS

Protein Purification

Figure 1:
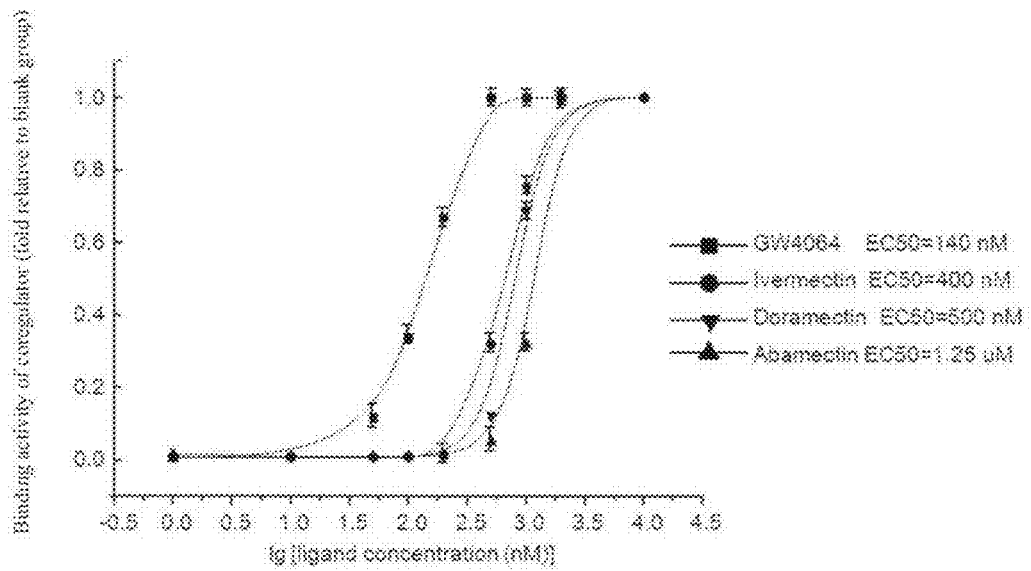
FIG. 1 shows the activity of recruiting coregulator SRC1 by abamectin, ivermectin, and doramectin after binding to FXR. GW4064 is used as FXR activator positive control.

1. Cloning (1) PCR reaction is performed using human FXR expression plasmid (pCMX-FXR) as a template, 0.5 µl 50 mM forward primer 5'GATATGGATCCAATCCAGAGTC-CGCTGACCTC and 0.5 µl 50 mM reverse primer 3'GATATCTCGAGCTAGTACAAGTCCTTGTAGATC as primers, 4 µl 10× PCR buffer, 1 µl 10 mM dNTP and 5 U pfu enzyme (Invitrogen), made up to 50 µl system with water (Milli-Q), to obtain a PCR product of human FXR LBD (ligand binding domain) (amino acid residue number being 243-472) containing two restriction enzyme digestion sites of BamH I and Xho I. PCR procedures are performed as follows: 94° C. for 2 min; 94° C. for 30 s, 58° C. for 1 min, 72° C. for 1 min, 30 cycles; and 72° C. for 10 min.

(2) Enzyme digestion is performed on DNA fragments obtained from PCR and prokaryotic cell expression vector pET24a (Novagen), the PCR products and pET24a vector are digested with BamH I and Xho I. The enzyme digestion system comprises FXR LBD PCR products or pET24a vector of 1 µg (10 µl), BamH I (Thermo) of 0.5 µl, Xho I (Thermo) of 0.5 µl, 10× enzyme digestion buffer (Thermo) of 4 µl and ddH$_2$O (Milli-Q) of 25 µl. The system is incubated at 37° C. for 1.5 h. The digested PCR products and pET24a vector are separated by 1% agarose gel with SYBR DNA dye, and DNA is recovered by Promega gel extraction kit.

(3) The recovered fragments and vector are ligated in a molar ratio of 3:1. The ligation system comprises FXR LBD DNA fragments of 2 µl, pET24a (Novagen) vector of 2 µl, 5× ligation buffer (Invitrogen) of 2 µl, and T4 DNA ligase (Invitrogen) of 0.5 µl, made up to 10 µl with ddH$_2$O. The system is reacted at room temperature for 30 min.

(4) The ligated product of 2 µl is transformed to 50 µl Trans109 competent cells, and subjected to ice bath for 30 min followed by heat shock at 42° C. for 30 s. 250 µl of LB liquid medium without antibiotics is added, and preshaken at 225 rpm at 37° C. for 40 min, followed by taking 150 µl of transformation products, spreading same on LB solid medium plates with kanamycin at 50 µg/ml and culturing them at 37° C. overnight. On the next day, the single colony is picked out and placed in 2 ml LB liquid media containing kanamycin at 50 µg/ml, and cultured under shaking at 37° C. for 10 h.

(5) Plasmid extraction is performed on the shaken bacterial solution using Qiagen MiniPrep Plasmid Miniprepara-tion Kit.

(6) The extracted plasmid is identified using enzyme digestion. The enzyme digestion identification system comprises plasmid of 1 µg (2 µl), BamH I (Thermo) of 0.5 µl, Xho I (Thermo) of 0.5 µl, 10× enzyme digestion buffer (Thermo) of 2 µl and ddH$_2$O (Milli-Q) of 15 µl. The system is subjected to enzyme digestion reaction in an incubator at 37° C. for 30 min, and detected with 1% agarose gel so as to determine the successful insertion of target fragment into the expression vector. Finally, the obtained plasmid is identified by sequencing. The expression plasmid of human nuclear receptor FXR LBD tagged with hexahistine is obtained and represented as pET24a-His6-FXR LBD.

2. The Target Protein Expression and Purification (1) Transformation. pET24a-His6-FXR LBD is transformed into BL21 (DE3) competent cells. 1 µl of plasmid is taken and transformed into 50 µl BL21 competent cells, and subjected to ice bath for 30 min, followed by heat shock in water bath at 42° C. for 30 s. 250 µl of LB liquid medium without antibiotics is added, and preshaken at 225 rpm at 37° C. for 40 min, followed by taking 15 µl of products, spreading same on LB solid medium plates with kanamycin at 50 µg/ml and culturing them at 37° C. overnight.

(2) Shaking culture. On the next day, the single colony is picked out and placed in 50 ml LB liquid media containing kanamycin at 50 µg/ml, preshaken at 37° C. for 8 h, and transferred to 1.5 l LB liquid media containing kanamycin at 50 µg/ml, and when OD$_{600}$ reaches about 1.0, 0.1 mM IPTG is added to induce the expression at a low temperature of 16° C.

(3) The bacterial cells containing induced target protein are collected. 1.5 l of bacterial solution induced and expressed overnight is centrifuged at 3,000 rpm at 4° C. for 10 min to collect the bacteria, the bacterial solution is resuspended with a purificaton buffer of 100 ml (20 mM Tris pH 8.0, 150 mM NaCl, 10% glycerol, and 25 mM imidazole) and cryopreserved at −80° C.

(4) The protein extraction. Fisher Scientific Sonic Dismembrator Ultrasonic Cell Disruptor is used to perform the ultrasonic processing at an amplitude of vibration of 60%, frequency of working for 5 s and resting for 10 s, for 10 min. The product is centrifuged at 20,000 rpm at 4° C. for 30 min, followed by taking the supernatant.

(5) The protein purification. The supernatant is passed over 5 ml nickel ion exchange column (NiSO4-loaded HisTrap HP column, GE Healthcare) so that the target protein is enriched at the nickel column sufficiently. AKTA protein purification system from GE Co. and UNICORN software are used for the operation. Washing the pump: the pump is washed firstly with water and then with a buffer. The operation procedures comprise: in the System Control window, Manual→Pump→Pumpwashbasic→PumpA, Pump-B→On→Excute are selected sequentially. The connection of chromatographic column: the system pump is firstly activated, and when there is solution flowing out, the chromatographic column is connected to the system dynamically, so that the peak value of flowed protein can be detected via UV, and UNICORN software is opened to edit the procedure of protein elution: performing column equilibration with 20 ml elution buffer; performing competitive binding to the column with 25-500 mM imidazole in a gradient to elute off the target protein; and performing column equilibration with 15 ml buffer. Protein elution: the protein on the column is subjected to gradient elution with elution buffers A and B (the components of elution buffer A: 25 mM Tris, 150 mM NaCl, 25 mM imidazole and 10% glycerine, pH 7.5; the components of elution buffer B: 25 mM Tris, 150 mM imidazole and 10% glycerine, pH 7.5), and the target protein containing histidine-tag with a structure similar to imidazole can be eluted off under competition of suitable concentrations by controlling the imidazole concentration gradient to be varied from 25 to 500 mM. The target protein solution eluted from the nickel ion exchange column is further purified for the target protein using Hiload26 molecular sieve chromatography column (GE Healthcare) as claimed in different molecular mass, with the steps as follows: the protein solution collected by nickel column is injected into AKTA sample loading ring by a syringe, followed by starting the program running with the same method as above. The protein elution buffer is changed to elution buffer C containing 10 mM NaCl (elution buffer C: 25 mM Tris, pH 7.5).

(6) The preparation of a protein complex. Synthesized NcoR2 polypeptide (PASNLGLEDIIRKALMGS) customized from GenScript and FXR LBD protein are used for preparing a complex as follows: 20 ml of protein obtained from the molecular sieve chromatography, NcoR2 polypeptide and ivermectin are mixed in a molar ratio of 1:1:1, added to and concentrated in 10 kD MILLIPORE 15 ml concentration tube, centrifuged and concentrated at 4,000 rpm at 4° C., and the protein is concentrated to reach a final concentration of 10 mg/ml.

3. Protein Crystallization, Crystal Data Collection and Structural Resolution

Crystallization screening is performed using hanging drop method, and the FXR/Ivermectin/NcoR2 complex is placed at a condition of room temperature, the components of a hanging drop solution comprising a mixture of 1.0 μl protein polypeptide ligand complex solution mentioned above and 1.0 μl crystallization buffer (50 mM HEPES pH 7.0, 3.5 M sodium formate). Crystals which have grown to be mature are subjected to rapid cryopreservation with liquid nitrogen. The data are acquired with BL17U1 line station of Shanghai Synchrotron Radiation Facility. After the radiation treatment with X-rays, the obtained diffraction data is processed with HKL2000 software to ensure that each asymmetric unit comprises two molecules, the crystal spacial group is I 21 21 21 (a=53.01, b=161.76, c=169.02, α=90°, β=90°, and γ=90°), the specific structural resolution is performed using Molrep, Phaser, etc. in CCP4 software package (http://www.ccp4.ac.uk) by which a general structural model can be determined through molecular replacement, and the final protein complex structure can be obtained by the fine construction of an artificial model of Coot and multiple cycles of further modification by REFMAC and phenix.refine, wherein Rwork and Rfree of this structural model are 25.4% and 28.2% respectively with a resolution of 2.81 Å. Reference of specific three-dimensional crystal structure space elements can be made to Appendix 1.

4. Cofactor Binding Experiment

The binding ability of ligands used to induce the nuclear receptors to recruit various types of coregulators is detected using Alpha Screen nickel chelate detection kit (PerkinElmer) through Alphascreen analysis method. The reaction system of 50 μl in this experiment comprises 20 nM fusion histidine tagged receptor LBD protein, 20 nM biotin tagged cofactor polypeptide, donor and receptor beads at 5 μg/ml, and a buffer (50 mM MOPS, 50 mM NaF, 0.05 mM CHAPS, and 0.1 mg/ml bovine serum albumin, pH 7.4), and the reaction system is reacted in a 384-well plate at room temperature for 1 h, followed by reading signals of excitation light at 680 nm and emission light at 520-620 nm with AlphaScreen detector. The biotin tagged polypeptide and the sequence for Alphascreen analysis are SRC1-2 and SPSSHSSLTERHKILHRLLQEGSP, respectively.

5. Transient Transfection Experiment

1. Plasmid:

(1) FXR full-length plasmid: human FXR full-length cDNA expression sequence is cloned into the pCMX expression vector using classical cloning method.

(2) The expression vector of FXR with point mutations at key binding sites is obtained. Quick-Change site-directed mutagenesis kit (Stratagene) is used for mutation, and the mutation reaction system is as follows: wild-type plasmid pCMX-FXR (50 ng) of 0.5 μl, mutation primer (100 μM) of 0.2 μl, pfu DNA polymerase (Invitrogen) (2 U) of 1 μl, 10 mM dNTPs of 1 μl, 10× PCR buffer of 5 μl, and ddH$_2$O of 43 μl. PCR procedures are performed as follows: 94° C. for 2 min; 94° C. for 30 s, 55° C. for 1 min, 72° C. for 7 min, 15 cycles. 20 μl PCR product is digested with Dpn I methylase, followed by taking and transforming 2 μl digestion product into *E. coli* Trans 109 competent cells, ice bath for 30 min, and heat shock at 42° C. for 30 s. 250 μl of LB liquid medium without antibiotics is added, and preshaken at 225 rpm at 37° C. for 40 min, followed by taking 150 μl of products, spreading same on LB solid medium plates with ampicillin at 100 μg/ml and culturing them at 37° C. overnight. On the next day, the single colony is picked out and placed in 2 ml LB liquid medium containing ampicillin at 100 μg/ml, and cultured at 37° C. overnight. Plasmid extraction is performed on the shaken bacterial solution using Qiagen MiniPrep Plasmid Minipreparation Kit. The plasmid is identified by sequencing.

2. Transfection:

DMEM medium containing 10% fetal bovine serum is used to perform the culture of monkey kidney epithelial cell COS-7 cells, and COS-7 cells are inoculated onto a 24-well plate on the day before transfection with an inoculation density of 5×10$^4$ cells/well, and transfected on the next day. The transfection is the transient transfection performed using Lipofectamine 2000 (Invitrogen). In the reporter gene analysis experiment, 200 ng of a nuclear receptor full-length expression plasmid or the expression plasmid of the mutant thereof, 200 ng of endogenous promoter reporter gene, and 30 ng of Renilla luciferase expression plasmid are used for cotransfection. 500 μl Opti-MEM is added to each well and cultured for 5 h, followed by adding a ligand medicament diluted in Opti-MEM to reach the corresponding concentration, and treating for 18 h. Various nuclear receptors and the corresponding reporter gene used are as follows: human FXR, EcRE-Luc; human PPARs (α, β, and γ), PPRE-Luc; human RORs (α, β and γ), Pcp2/RORE-Luc; human GR and PR, MMTV-Luc; human RARα and RARβ, and βRE-Luc.

Figure 2:
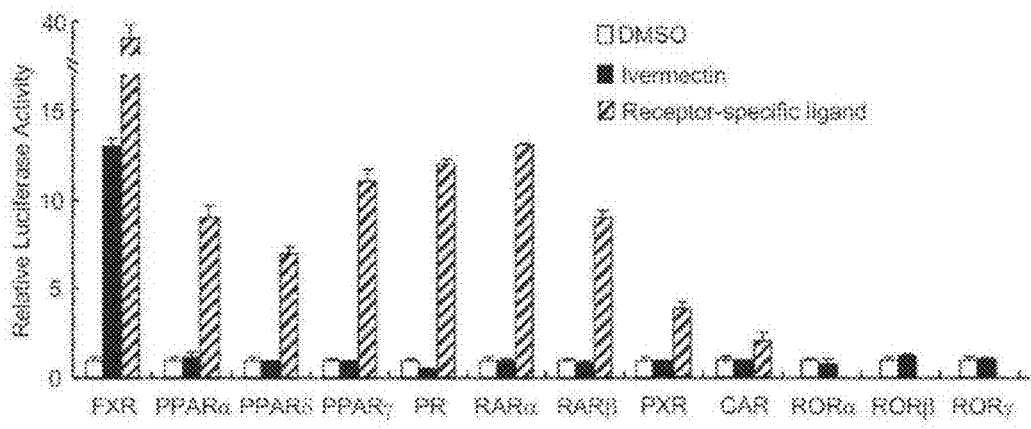
FIG. 2 shows specific transcriptional activation of FXR receptor by 0.5 μM ivermectin. COS-7 cells are cotransfected with full-length expression plasmids of different nuclear receptors such as FXR and the reporter genes constructed by the corresponding endogenous binding elements of different nuclear receptors. After the transfection, cells are treated with DMSO, 0.5 μM ivermectin or the specific agonist against each of the nuclear receptors respectively.

3. The Reporter Gene Analysis:

A ligand medicament is added to the cells treated with the above transfection method 4-6 h after the transfection, and all the concentrations of ivermectin for the reporter gene analysis are 0.5 μM in the examples. In FIG. 2, the specific ligand against each nuclear receptor and the concentration thereof are: FXR, 0.5 μM GW4064; PPARα, 1 μM GW590735; PPARδ, 1 μM GW0472; PPARγ, 1 μM rosiglitazone; glucocorticoid receptor (GR), 0.1 μM dexamethasone; progesterone receptor (PR), 0.1 µM progesterone; RAR and RARβ, 1 µM all-trans-retinoic acid; PXR, 10 µM rifampicin; CAR, 5 µM CITCO ((6-(4-chlorophenyl)imidazo[2,1-b][1,3]thiazole-5-formaldehyde-O-(3,4-dichlorobenzyl)ethyl ketoxime). After the ligand medicament is treated for 18 h, the reporter gene activity analysis is performed using double luciferase reporter gene analysis kit from Promega Co. Cells are lysed for the luciferase detection experiment, 10 µl of lysed cells are transferred to a 96-well plate, and 50 µl of luciferase reaction solution is added, followed by detecting the signal of emission light at 560 nm with EnSpire™ 2300 Multimode Reader (PerkinElmer), adding Stop & Glo® reaction solution to stop the luciferase reaction, and detecting the Renilla luciferase activity. The Renilla activity is used as the internal reference for the activity of reporter genes.

6. Mouse Trials

Wild-type C57BL/6J mice of 9-10 weeks old, and FXR gene deletion homozygous mice (FXR$^{-/-}$) and diabetes and obesity mouse model mice (KK-Ay) with the same background are used, fed with high-fat diet (Research Diets, D12492), with free access to water, in SPF grade animal room in experimental animal center, Xiamen University. Mice are divided into a control group, ivermectin or the derivatives thereof treated group and/or GW4064 treated group, with 6 mice in each group, and are subjected to intraperitoneal injection of a control solution (40% HBC (2-hydroxypropyl-β-cyclodextrin)), ivermectin or the derivatives thereof diluted with the control solution (the injection amount being 1.3 mg/kg calculated according to the medicament mass/mouse body weight), and GW4064 (30 mg/kg) diluted with the control solution respectively. Intraperitoneal injection is performed one time at 9 o'clock every morning, continued for 14 days, and the mice are measured for body weight and the food intake every two days. At the end of 14 days, the mice are provided with free access to water, and after being hungry for 6 h, the mouse body weights are measured, and the percentage of the final body weight relative to the initial body weight before the treatment of the injection trial indicates the change of mouse body weight. Then blood is sampled from the eye balls, and sera are obtained by separation. The components in serum are detected by the following kits respectively: sugar-oxidase method (Beijing Applygen); insulin (Crystal Chem. Inc., USA); total cholesterol and cholesterol in high and low density lipoprotein (Bioassay Systems, USA); triglyceride (Beijing Applygen and WAKO Chemicals Inc., Japan); free fatty acids (Bioassay Systems, USA); and aspartate aminotransferase and alanine aminotransferase (Biosino Bio-technology and Science Inc., Beijing, China). Mouse liver is taken, a part of which is fixed with paraformaldehyde, and embedded with paraffin, sectioned, and stained with hematoxylin and eosin, and a part of which is cryopreserved with liquid nitrogen for use in extracting RNA for measuring gene expression with fluorescence quantitative PCR.

7. Measurement of Gene Expression with Fluorescence Quantitative PCR

Liver tissues are obtained from the wild-type mice treated with the control (40% HBC) or ivermectin, and the FXR knockout mouse model, and from the KK-Ay mouse model treated with the control, GW4064 or ivermectin, then cryopreserved in a refrigerator at −80 degrees. Total RNA is extracted from the tissues using an RNA extraction kit (Omega Bio-Tek, GA). TAKARA reverse transcription kit is used for the reverse transcription, and fluorescence quantitative PCR is performed with CFX™ 96 (BIO-RAD) real-time monitoring system using SYBR green fluorescent dye so as to analyze the gene expression level. The expression level of Actin gene is used as the internal reference for the results. The reaction system comprises SYBR Premix Ex Taq (2×) of 12.5 µl, PCR forward primer (10 µM) of 1 µl, PCR reverse primer (10 µM) of 1 µl, cDNA template of 2 µl, and sterilized distilled water of 8.5 µl, 25 µl in total. The two-step amplification PCR procedures are as follows: pre-denaturation at 95° C. for 30 s, PCR reaction at 95° C. for 5 s, and 60° C. for 40 s. 40 cycles.

Particular examples are provided below:

EXAMPLE 1

It is Demonstrated that Ivermectin is a Novel FXR Ligand with High Affinity and High Specificity A ligand can be tested for the affinity to FXR since the ligand can induce FXR to recruit coregulators after binding to FXR. Specific ligands of FXR are screened by AlphaScreen, and it is found that the affinity of ivermectin, abamectin/avermectin, and doramectin to FXR differs from that of synthetic GW4064 by less than one order of magnitude, wherein the affinity half effective concentration (EC50) of GW4064 to FXR is 140 nM, and EC50 of ivermectin, doramectin and abamectin/avermectin are respectively 400 nM, 500 nM and 1.25 µM in this experiment (FIG. 1). It is suggested that ivermectin, abamectin/avermectin, and doramectin bind to FXR with very high affinity. In order to demonstrate that ivermectin can specifically bind to FXR, we use an endogenous reporter gene EcRE of FXR and a plasmid expressing full-length FXR to cotransfect COS-7 cells. The results indicate that as for different nuclear receptors detected, ivermectin can only specifically activate the transcriptional activity of FXR and does not produce any effect on the other detected nuclear receptors (FIG. 2). This shows the high specificity of ivermectin as the FXR ligand.

EXAMPLE 2

Crystal Structural Resolution of FXR/Ivermectin Complex

Figure 3:
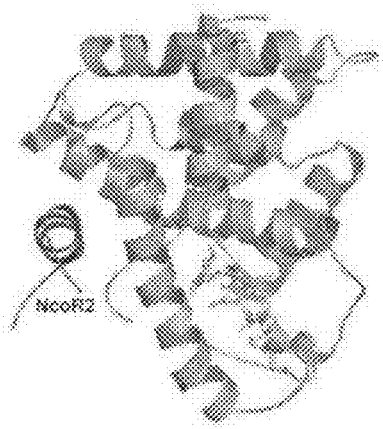
FIG. 3 shows a crystal diffraction structural diagram of the binding complex of FXR protein and ivermectin. Ivermectin binding at the LBD ligand pocket of FXR is represented by a bar structure. NCoR2 indicates a polypeptide with FXR binding sequence among coregulator NCoRs which form a complex with FXR and ivermectin.
Figure 4:
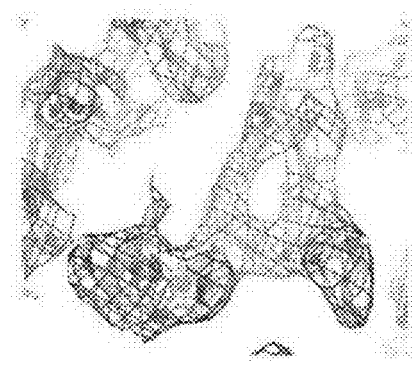
FIG. 4 shows an electron cloud diagram of ivermectin binding to FXR.
Figure 5:
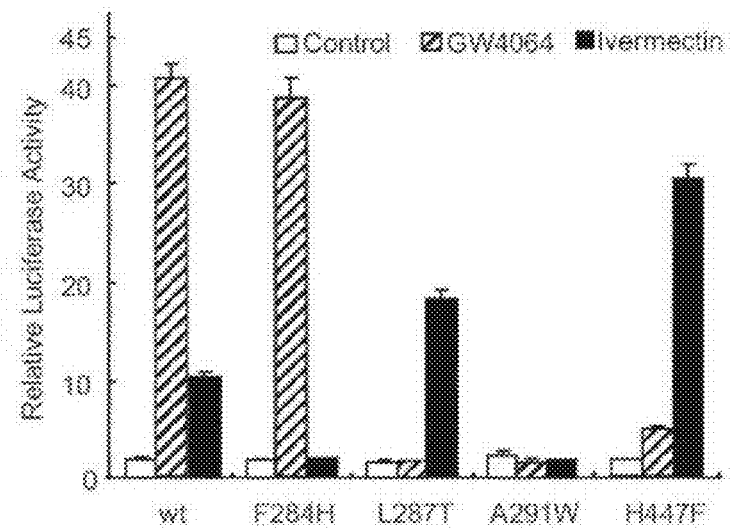
FIG. 5 shows that the activation of transcriptional activity of FXR by ivermectin and GW4064 is affected by the mutations of key amino acids of FXR which interact with ivermectin. COS-7 cells are cotransfected with the expression plasmid expressing full-length FXR (wt) or with mutations at the corresponding sites and EcRE reporter gene, treated with ivermectin and GW4064, and examined for the transcriptional activity 24 hours later. The abscissa indicates wild-type FXR (wt) and FXR mutant with mutations at 4 amino acid sites.
Figure 6:
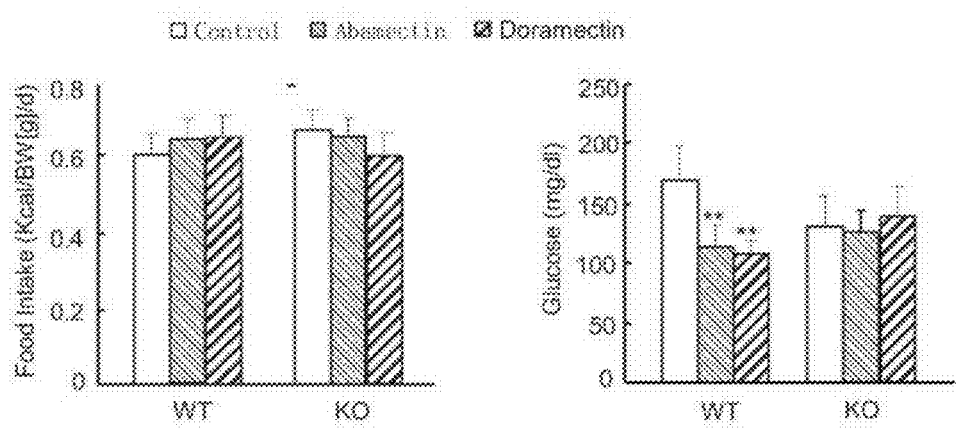
FIG. 6 shows that the treatment with abamectin and doramectin does not produce any effect on the food intake of the wild-type and FXR knockout mice, but decreases the serum glucose level in the wild-type mice. ** means that $p<0.01$.
Figure 7:
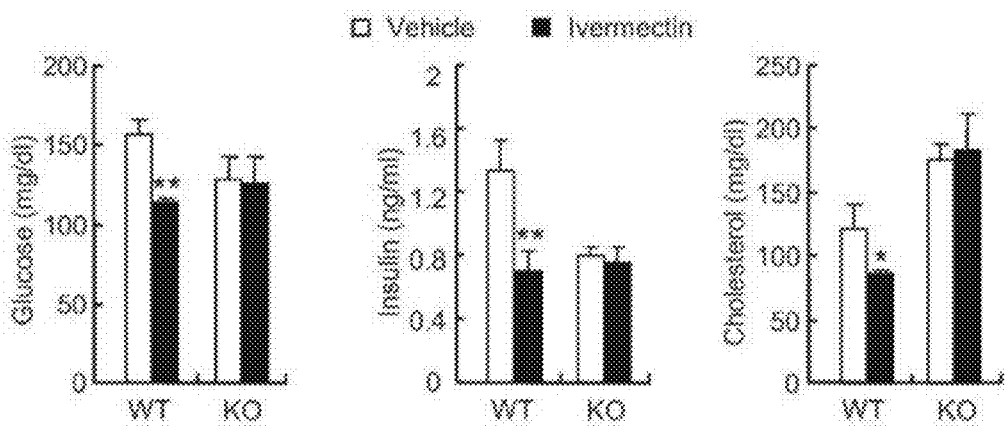
FIG. 7 shows that after the treatment with ivermectin, the levels of saccharides, insulin, and cholesterol in sera in the wild-type mice (WT) fed with high-fat diet are decreased respectively. In the FXR knockout mice (KO), these indices are not affected by the drug treatment. * means that $p<0.05$, and ** means that $p<0.01$.
Figure 8:
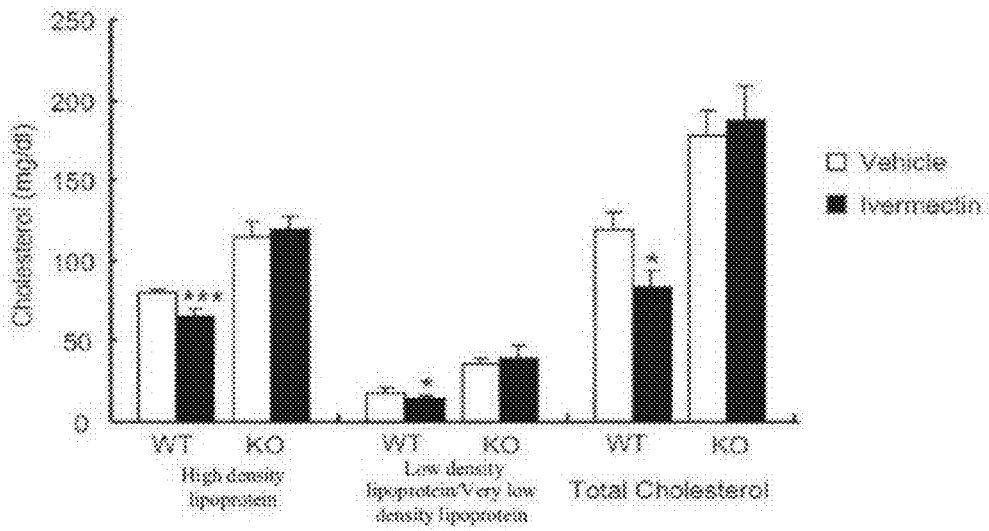
FIG. 8 shows that after the treatment with ivermectin, the levels of cholesterol in the mouse body are down-regulated, comprising cholesterol in high density lipoprotein and low density/very low density lipoprotein. In the FXR knockout mice (KO), these indices are not affected by the drug treatment. * means that $p<0.05$,  means that $p<0.01$, and * means that $p<0.001$.
Figure 9:
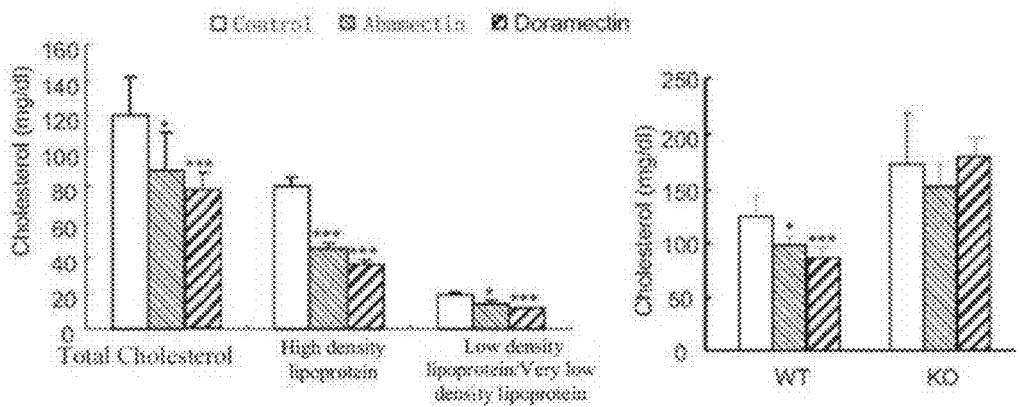
FIG. 9 shows that after the treatment with abamectin and doramectin, the levels of serum cholesterol in the wild-type mice fed with high-fat diet are decreased, comprising cholesterol in high density lipoprotein and low density/very low density lipoprotein. * means that $p<0.05$, and *** means that $p<0.001$.
Figure 10:
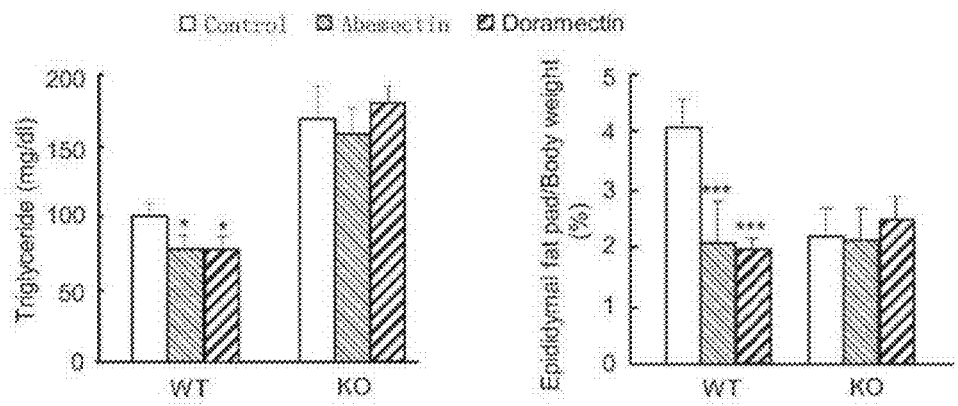
FIG. 10 shows that after the treatment with abamectin and doramectin, the levels of serum triglycerides and epididymal fat pad/body weight ratio in the wild-type mice fed with high-fat diet are decreased. * means that $p<0.05$, and *** means that $p<0.001$.
Figure 11:
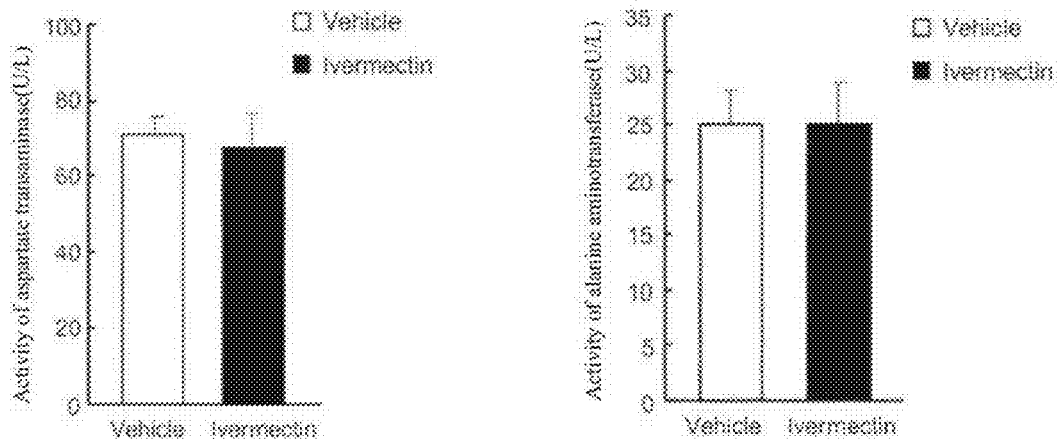
FIG. 11 shows that the activity of aspartate aminotransferase and alanine aminotransferase in the wild-type mice treated with ivermectin is not affected.
Figure 12:
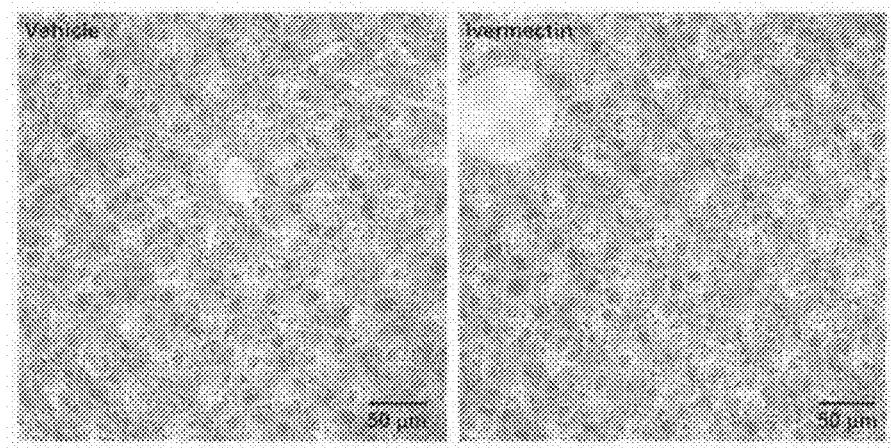
FIG. 12 shows that after the treatment with ivermectin, a liver tissue section, stained with hematoxylin and eosin, of a wild-type mouse indicates that ivermectin produces no liver injury. Vehicle indicates the blank control which is injected without the medicament.
Figure 13:
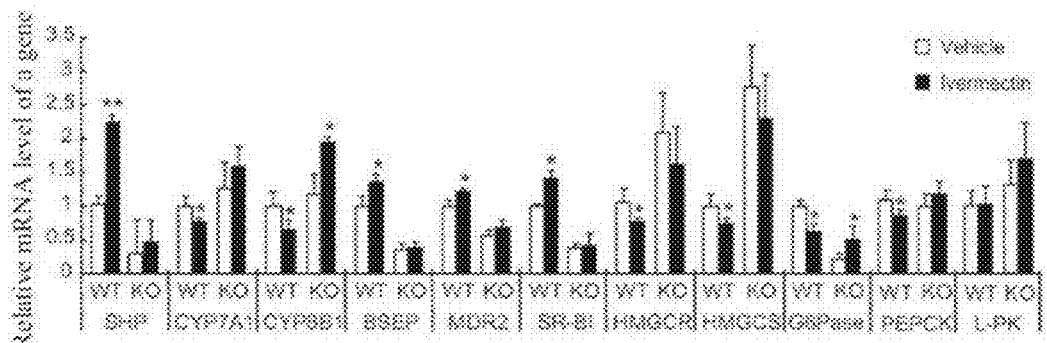
FIG. 13 shows that the real-time fluorescent quantitative PCR method is used to detect the expression of FXR targeting genes and genes associated with the saccharide, triglyceride and cholesterol metabolism in the liver of a wild-type mouse treated with ivermectin. * means that p<0.05, and ** means that p<0.01.

In order to reveal the molecular mechanism of recognition and binding between ivermectin and FXR at the molecular level, we resolve the crystal structure of the complex formed by FXR/ivermectin and corepressors NCoR nuclear receptor binding motif with a resolution of 2.8 Å (Appendix 1, and FIG. 3). The structure shows that the binding of ivermectin with FXR ligand binding domain conforms to the classical "sandwich" conformation. It can be seen from the electron cloud diagram that ivermectin is clearly present in the ligand binding pocket of FXR (FIG. 4). It can be seen from the structure that the binding of ivermectin results in the classical helical structure of FXR carboxy-terminus AF-2 being changed (FIG. 3), which indicates that ivermectin has a different functioning manner from synthetic FXR ligand GW4064 in the aspect of inducing FXR to recruit and bind to coactivators and corepressors, and ivermectin can regulate the function of FXR in a unique binding manner. Reference of the specific information regarding the binding pattern of FXR to ivermectin can be made to Appendix 1.

EXAMPLE 3

Unique Binding Site of Ivermectin in FXR Ligand Binding Pocket

Figure 14:
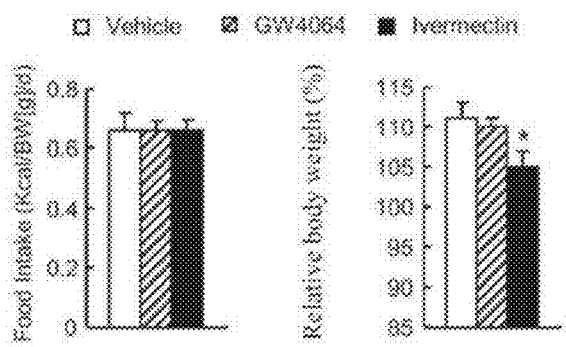
FIG. 14 shows that the treatment with ivermectin does not affect the food intake of the KK-Ay diabetes model mice but decreases the body weights thereof. * means that p<0.05.
Figure 15:
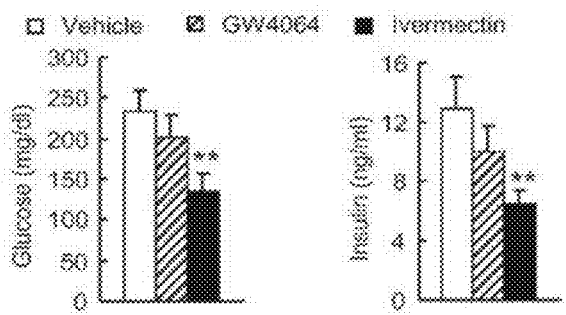
FIG. 15 shows that after the treatment with ivermectin, the levels of glucose and insulin in sera in KK-Ay mice are decreased. ** means that p<0.01.
Figure 16:
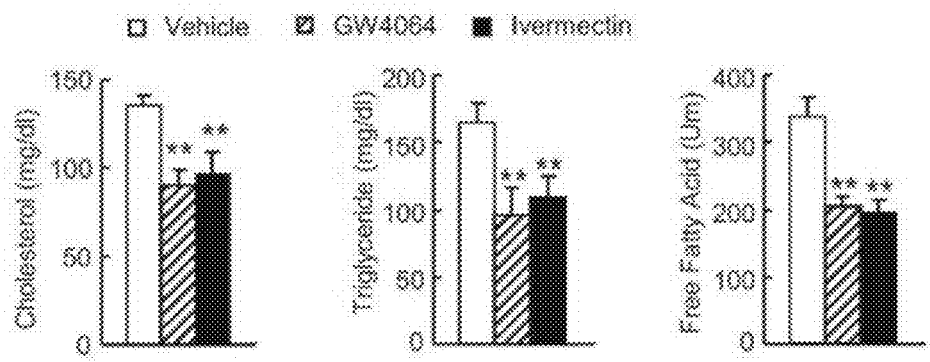
FIG. 16 shows that after the treatment with ivermectin, the levels of cholesterol, triglycerides and free fatty acids in sera in KK-Ay mice are decreased. ** means that p<0.01.

In order to verify the amino acid sites in FXR ligand binding pocket to which ivermectin can bind directly, we perform point mutations on the key sites for the binding of FXR to ivermectin according to the structure of FXR-ivermectin complex, and detect the change in the transcriptional activity of mutated FXR regulated by the ligand so as to determine the importance of these binding sites for the binding of ivermectin to FXR.

Alanine (A) at position 291 plays an important role in regulating the size of FXR ligand binding domain. When A291 is mutated to tryptophane (W), the side chain group of tryptophane which is much larger than that of alanine occupies the space of the ligand binding pocket, thereby resulting in FXR ligand binding pocket becoming small so as to affect the binding of FXR ligand. Consistent with what is expected, the reporter gene analysis experiment results indicate that the mutation of A291W results in GW4064 and ivermectin being incapable of activating the transcriptional activity of FXR (FIG. 5). This indicates that the alanine residue at position 291 of FXR is very important for the binding of GW4064 or ivermectin and activating FXR transcriptional activity.

Phenylalanine (F) at position 284 at the hydrophobic chain can form hydrophobic interaction with GW4064 and ivermectin respectively so as to stabilize the binding of the ligand and the receptor. When F284 is mutated to histidine (H), these two types of hydrophobic interaction disappear. However, in the other aspect, as for GW4064, after the mutation to histidine, the side chain groups of histidine may form chlorine bond interaction with GW4064, and therefore the disappearance of hydrophobic interaction will result in ivermectin being incapable of activating the transcriptional activity of FXR, while the activation ability of GW4064 is not affected (FIG. 5). This indicates that the binding pattern of ivermectin to FXR ligand binding pocket is unique and different from that of GW4064.

In addition, the mutations of L287T and H447F significantly decrease the GW4064 mediated transcriptional activity of FXR, while significantly increasing the activation of FXR transcriptional activity by ivermectin (FIG. 5). This also indicates that the binding manners of GW4064 and ivermectin to FXR are greatly different, and the regulation of FXR function is also significantly different.

EXAMPLE 4

Ivermectin can Effectively Regulate the Metabolism of Saccharides and Lipids of a Mammal FXR, as an important nuclear receptor, is firstly used as a receptor of bile acid to regulate the circulation and equilibrium of bile acid in the liver and small intestine. Recently, it has been found that FXR can regulate the metabolism of saccharides and lipids in an organism. Synthetic FXR ligand GW4064 can decrease the levels of blood lipid and cholesterol through FXR, but the cytotoxicity and efficacy limit of GW4064 result in that it cannot be used clinically; furthermore, there is a report suggesting that GW4064 can relieve hyperglycemia and obesity, but at the same time some articles also propose that GW4064 has no significant effect on blood glucose in the body, and there is even a report suggesting long-term taking of GW4064 would render mice obese. Therefore, there are some controversies in the regulation of blood glucose by GW4064. It would be more important and meaningful to find new ligand medicaments for FXR.

In order to detect the physiological regulation function of a mouse model by ivermectin, we use wild-type and FXR knockout mice to perform the trial. After the mice fed with high-fat diet are subjected to intraperitoneal injection, as described in the particular embodiments, with the control agent, ivermectin or the derivatives thereof for two weeks, it is found that in the case that the medicaments do not produce any effect on the food intake of mice (FIG. 6), the treatment with abamectin/avermectin, ivermectin, and the derivative doramectin significantly decreases the levels of glucose (FIGS. 6 and 7) and cholesterol (FIGS. 7, 8 and 9) in sera in wild-type mice, while not producing any significant change in FXR knockout mice. The treatment with ivermectin significantly decreases the level of serum insulin in wild-type mice (FIG. 7), which indicates that ivermectin may achieve the effect of decreasing blood glucose through increasing the sensitivity of insulin. However, in FXR knockout mice, the medicament treatment does not produce any significant change in the levels of blood glucose, insulin and cholesterol, which indicates that abamectin/avermectin, ivermectin, and the derivative doramectin regulate the blood glucose, insulin and cholesterol in sera through FXR. Abamectin/avermectin, ivermectin, and the derivative doramectin downregulate the serum cholesterol levels in mice, comprising not only the significantly downregulated cholesterol level in high density lipoprotein, but also the downregulated cholesterol levels in low density and very low density lipoprotein (FIGS. 8 and 9). In addition, abamectin/avermectin, ivermectin, and the derivative doramectin also significantly decrease the serum triglyceride (Tg) level in wild-type mice (FIG. 10). Importantly, the specific weight of the epididymal fat pad in a mouse body treated with abamectin/avermectin and doramectin is also significantly reduced (FIG. 10), which indicates their therapeutical effect on obesity. The detection of activity of serum alanine aminotransferase and aspartate aminotransferase (FIG. 11) indicates that ivermectin does not affect the transaminase activity. The mouse liver treated with ivermectin is embedded with paraffin, sectioned, and stained with hematoxylin and eosin (FIG. 12), which shows that ivermectin produces no injury to liver cells.

The expression of genes associated with saccharides, lipids, and cholesterol metabolism in mouse liver treated with ligand medicaments is detected by fluorescent quantitative real-time PCR. The results indicate that consistent with the expression regulation of genes associated with saccharides, lipids, and cholesterol metabolism, ivermectin can achieve the physiological function of decreasing blood glucose, blood lipid, and cholesterol (FIG. 13), which indicates that ivermectin can regulate the expression of genes associated with metabolism through FXR so as to achieve the regulation of physiological function. These results indicate that ivermectin is a specific ligand of FXR, and also demonstrate that the regulation of physiological function by ivermectin in vivo is achieved through FXR.

EXAMPLE 5

The Effect of Abamectin/Avermectin, Ivermectin and the Derivative Doramectin in Diabetes Mouse Model Abamectin/avermectin, ivermectin and the derivative doramectin, as ligands of FXR, can play an important role in metabolic regulation in a normal mouse body, the problem is then whether they can have an improved therapeutic effect in a pathological mouse. In order to detect the efficacy of abamectin/avermectin, ivermectin and the derivative doramectin in the body of a diabetes and obesity mouse model, we choose diabetes and obesity mouse model mice, KK-Ay mice, as the experimental subject. Such mice can exhibit significant hyperglycemia and obesity symptoms at about 8-12 weeks. In the experiment, KK-Ay mice of 9-10 weeks old are used, fed with high-fat diet and subjected to intraperitoneal injection of medicaments for 14 days, and in the case that the food intake of mice is not affected (FIG. 14), both ivermectin and GW4064 significantly decrease the contents of serum cholesterol, triglycerides and free fatty acids (FIG. 16); while in the blood glucose aspect, ivermectin significantly decreases the levels of serum saccharides and insulin, which indicates that ivermectin may achieve the effect of decreasing blood glucose through increasing the sensitivity of insulin, and in this aspect, ivermectin is significantly superior over GW4064 in the function as the ligand of FXR (FIG. 15). Furthermore, the treatment with ivermectin significantly decreases the body weights of KK-Ay mice, which also shows obvious superiority over GW4064 (FIG. 14). These results indicate that ivermectin has good effects in equilibrating blood glucose, blood lipid, and cholesterol and in inhibiting body weight gain in diabetes and obesity model mice, and has superior function and therapeutic effect over the synthetic ligand GW4064.

Figure 17:
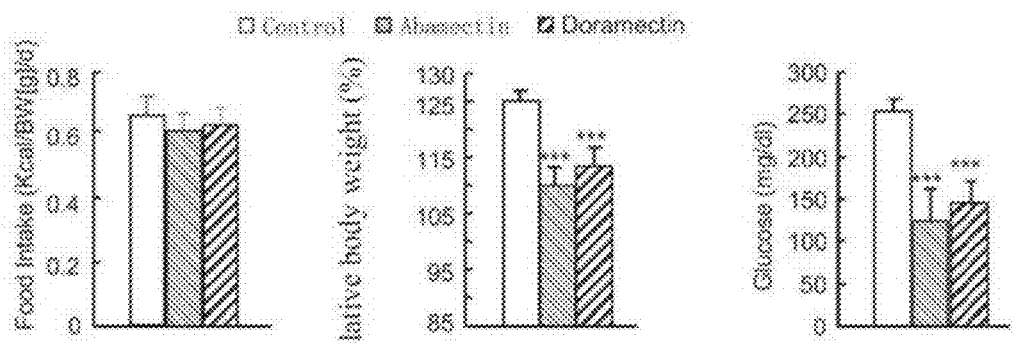
FIG. 17 shows that after the treatment with abamectin and doramectin, the food intake of KK-Ay mice is not affected, and the relative body weights and serum glucose levels of KK-Ay fed with high-fat diet are decreased. *** means that p<0.001.
Figure 18:
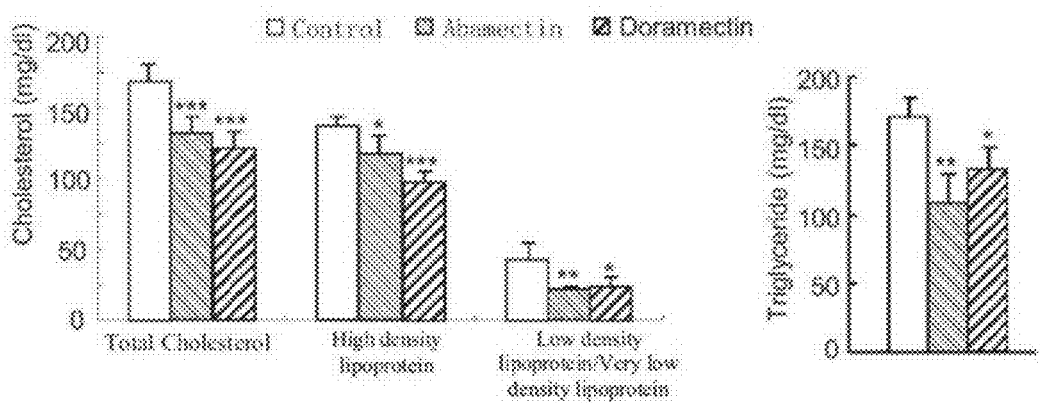
FIG. 18 shows that after the treatment with abamectin and doramectin, the levels of serum cholesterol (comprising cholesterol in high density lipoprotein and low density/very low density lipoprotein) and serum triglycerides in KK-Ay mice fed with high-fat diet are decreased. * means that p<0.05,  means that p<0.01, and * means that p<0.001.

The same trial of abamectin/avermectin and doramectin is performed in KK-Ay mice, and it is found that in the case that the food intake of mice is not affected (FIG. 17), abamectin/avermectin and doramectin can also significantly decrease the levels of glucose (FIG. 17), cholesterol in high density lipoprotein and low density/very low density lipoprotein, and triglycerides (FIG. 18) in sera in KK-Ay mice, and can also significantly decrease the relative body weights of mice with obesity (FIG. 17). These data indicate that ivermectin and the derivatives thereof have good therapeutic effect for diabetes and obesity.

EXAMPLE 6

Ivermectin Inhibits LPS Induced Inflammation Response Through Mediation of FXR

Figure 19:
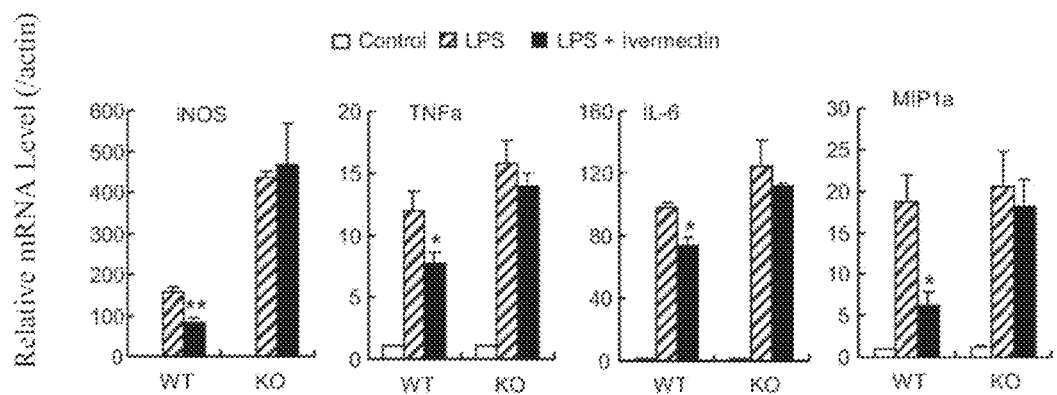
FIG. 19 shows that ivermectin can inhibit the expression of the genes (comprising iNOS, TNFa, IL-6 and MIP-1a) associated with inflammatory response induced by LPS. * means that p<0.05, and ** means that p<0.01.

Recently, some reports indicated that ivermectin can inhibit LPS induced inflammation response and reduce the death of mice induced by excessive LPS. Meanwhile, ivermectin has significant therapeutic effect for treating allergic asthma, but the specific mechanism of action is not clear. Ivermectin and LPS are used to treat wild-type and FXR knockout mouse liver cells. In wild-type mouse liver cells, ivermectin can clearly inhibit the expression of inflammatory factors, for example, iNOS, TNFa, IL-6 and MIP-1a (FIG. 19), but no clear change is observed in FXR knockout mouse liver cells. The result indicates that the inhibition of the LPS induced inflammation response by ivermectin is achieved through FXR.

EXAMPLE 7

Medicament Design of Ivermectin Derivatives Based on the Structure of the FXR/Ivermectin Complex It can be found from the above examples that ivermectin has a function completely different from that of an antiparasitic agent and has a new use for treating metabolism associated diseases in a mammal, such as hyperglycemia, insulin resistance, hypertriglyceridemia, hypercholesterolemia, diabetes and obesity, and Farnesoid X receptor mediated diseases, such as cholestasia, gallstones, non-alcoholic fatty liver, atherosclerosis, inflammation and cancer. Further according to the resolved three-dimensional crystal structural pattern where FXR binds to ivermectin (Appendix 1), using ivermectin as a safe leading compound, the molecular structure of ivermectin as a medicament design template, with the binding sites of ivermectin and FXR, and structure-function relationship thereof as the support, some groups of ivermectin are appropriately modified, thereby possibly improving the affinity and specificity of binding between the ligand and receptor, and achieving optimal efficacy, so as to achieve an optimal pharmaceutical therapeutic effect with a minimum ligand medicament amount, and reduce the toxicity of the medicament to cells and organism bodies. The structural formula of ivermectin is as follows:

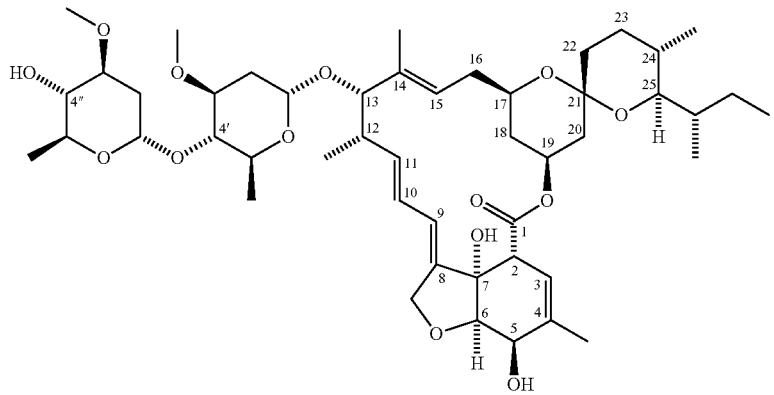

The structural formula is used as the structural basis, carbon-carbon double bonds of C3-C4, C8-C9, C10-C11, and C14-C15 in the structural formula are modified; hydroxyl groups at positions C5, C7 and C4" are modified; side chains at positions C4, C12, C14, C24 and C25 are modified; and the glycosyl at position C13 is hydrolyzed and other groups are modified such as through substitution. Any single modification and a combination of various modifications mentioned above can have application value in treating metabolism associated diseases in a mammal, such as hyperglycemia, insulin resistance, hypertriglyceridemia, hypercholesterolemia, diabetes and obesity, and Farnesoid X receptor mediated diseases, such as cholestasia, gallstones, non-alcoholic fatty liver, atherosclerosis, inflammation and cancer. According to the above design principles, abamectin/ avermectin, doramectin, etc. are also derivatives in conformity with the principles, and the mouse trials demonstrate that these compounds also have good regulation function and therapeutic effect in saccharide and lipid metabolism in a mammal.

INDUSTRIAL APPLICABILITY

The present invention provides the use of abamectin/avermectin, ivermectin, doramectin and other derivatives or a composition containing any one among them in preparing a medicament for treating metabolism associated diseases in a mammal, such as hyperglycemia, insulin resistance, hypertriglyceridemia, hypercholesterolemia, diabetes and obesity, and Farnesoid X receptor mediated diseases, such as cholestasia, gallstones, non-alcoholic fatty liver, atherosclerosis, inflammation and cancer.

THE REFERENCE MATERIALS RELATED TO THE PRESENT INVENTION PRIOR TO THE APPLICATION DATE

1. Chinese patent CN 1933856.
2. Chinese patent CN 1777433.

APPENDIX 1

```
REMARK  3   PROGRAM :                               REFMAC 5.6.0117
REMARK  3   RESOLUTION RANGE HIGH (ANGSTROMS) :     2.90
REMARK  3   COMPLETENESS FOR RANGE (%) :            98.21
REMARK  3   R VALUE (WORKING + TEST SET) :          0.25558
REMARK  3   R VALUE (WORKING SET) :                 0.25331
REMARK  3   FREE R VALUE :                          0.29623
CRYST1   53.008 161.759 169.018  90.00 90.00 90.00 I 21 21 21

ATOM     1  N    ASN  C  742   29.535 -19.999 -42.932  1.00  146.14  N
ATOM     2  CA   ASN  C  742   29.694 -20.610 -41.573  1.00  131.37  C
ATOM     3  CB   ASN  C  742   31.189 -20.765 -41.193  1.00  140.09  C
ATOM     4  CG   ASN  C  742   32.012 -19.494 -41.424  1.00  148.16  C
ATOM     5  OD1  ASN  C  742   32.283 -18.739 -40.488  1.00  148.99  O
ATOM     6  ND2  ASN  C  742   32.433 -19.268 -42.670  1.00  148.21  N
ATOM     7  C    ASN  C  742   28.901 -19.879 -40.479  1.00  128.91  C
ATOM     8  O    ASN  C  742   29.420 -19.630 -39.383  1.00  124.17  O
ATOM     9  N    LEU  C  743   27.641 -19.544 -40.780  1.00  127.89  N
ATOM    10  CA   LEU  C  743   26.788 -18.788 -39.840  1.00  119.00  C
ATOM    11  CB   LEU  C  743   25.670 -17.989 -40.541  1.00  104.27  C
ATOM    12  CG   LEU  C  743   26.017 -16.532 -40.868  1.00   92.01  C
ATOM    13  CD1  LEU  C  743   26.731 -16.448 -42.215  1.00   81.21  C
ATOM    14  CD2  LEU  C  743   24.780 -15.644 -40.831  1.00   77.51  C
ATOM    15  C    LEU  C  743   26.291 -19.566 -38.605  1.00  122.75  C
ATOM    16  O    LEU  C  743   26.863 -19.369 -37.533  1.00  136.39  O
ATOM    17  N    GLY  C  744   25.261 -20.424 -38.691  1.00  109.40  N
ATOM    18  CA   GLY  C  744   24.417 -20.677 -39.861  1.00   97.04  C
ATOM    19  C    GLY  C  744   22.997 -20.248 -39.534  1.00   96.15  C
ATOM    20  O    GLY  C  744   22.715 -19.052 -39.532  1.00  106.23  O
ATOM    21  N    LEU  C  745   22.101 -21.197 -39.236  1.00   87.05  N
ATOM    22  CA   LEU  C  745   20.731 -20.836 -38.840  1.00   75.33  C
ATOM    23  CB   LEU  C  745   19.778 -22.012 -38.889  1.00   72.34  C
ATOM    24  CG   LEU  C  745   18.316 -21.608 -39.152  1.00   78.31  C
ATOM    25  CD1  LEU  C  745   17.380 -22.815 -39.181  1.00   76.85  C
ATOM    26  CD2  LEU  C  745   17.787 -20.571 -38.168  1.00   77.61  C
ATOM    27  C    LEU  C  745   20.600 -20.175 -37.472  1.00   87.57  C
ATOM    28  O    LEU  C  745   20.215 -19.010 -37.409  1.00   99.57  O
ATOM    29  N    GLU  C  746   20.901 -20.899 -36.385  1.00   82.18  N
ATOM    30  CA   GLU  C  746   20.643 -20.390 -35.010  1.00   72.64  C
ATOM    31  CB   GLU  C  746   21.361 -21.234 -33.948  1.00   66.27  C
ATOM    32  C    GLU  C  746   20.909 -18.885 -34.765  1.00   71.89  C
ATOM    33  O    GLU  C  746   20.262 -18.267 -33.907  1.00   63.66  O
ATOM    34  N    ASP  C  747   21.847 -18.295 -35.513  1.00   69.15  N
ATOM    35  CA   ASP  C  747   22.173 -16.876 -35.356  1.00   69.63  C
ATOM    36  CB   ASP  C  747   23.457 -16.567 -36.090  1.00   76.03  C
ATOM    37  CG   ASP  C  747   24.197 -17.828 -36.523  1.00   91.80  C
ATOM    38  OD1  ASP  C  747   24.443 -18.720 -35.682  1.00   99.45  O
ATOM    39  OD2  ASP  C  747   24.534 -17.930 -37.716  1.00   98.70  O
ATOM    40  C    ASP  C  747   21.019 -16.029 -35.894  1.00   70.43  C
ATOM    41  O    ASP  C  747   20.446 -15.173 -35.191  1.00   62.28  O
ATOM    42  N    ILE  C  748   20.667 -16.316 -37.141  1.00   68.09  N
ATOM    43  CA   ILE  C  748   19.453 -15.812 -37.776  1.00   68.30  C
ATOM    44  CB   ILE  C  748   19.079 -16.715 -38.984  1.00   70.48  C
ATOM    45  CG1  ILE  C  748   20.233 -16.767 -40.008  1.00   74.94  C
ATOM    46  CD1  ILE  C  748   20.024 -17.740 -41.161  1.00   87.18  C
ATOM    47  CG2  ILE  C  748   17.748 -16.303 -39.598  1.00   63.22  C
ATOM    48  C    ILE  C  748   18.286 -15.726 -36.778  1.00   69.76  C
ATOM    49  O    ILE  C  748   17.694 -14.675 -36.592  1.00   69.70  O
ATOM    50  N    ILE  C  749   17.965 -16.829 -36.114  1.00   77.01  N
ATOM    51  CA   ILE  C  749   16.871 -16.820 -35.140  1.00   71.15  C
ATOM    52  CB   ILE  C  749   16.530 -18.250 -34.683  1.00   75.56  C
ATOM    53  CG1  ILE  C  749   15.622 -18.885 -35.730  1.00   73.54  C
ATOM    54  CD1  ILE  C  749   15.410 -20.362 -35.526  1.00   78.13  C
ATOM    55  CG2  ILE  C  749   15.868 -18.265 -33.307  1.00   74.37  C
ATOM    56  C    ILE  C  749   17.136 -15.900 -33.960  1.00   64.02  C
```

APPENDIX 1-continued

| ATOM | 57 | O | ILE | C | 749 | 16.232 | −15.196 | −33.534 | 1.00 | 53.41 | O |
|---|---|---|---|---|---|---|---|---|---|---|---|
| ATOM | 58 | N | ARG | C | 750 | 18.382 | −15.913 | −33.463 | 1.00 | 72.34 | N |
| ATOM | 59 | CA | ARG | C | 750 | 18.858 | −15.014 | −32.400 | 1.00 | 72.35 | C |
| ATOM | 60 | CB | ARG | C | 750 | 20.357 | −15.163 | −32.217 | 1.00 | 77.09 | C |
| ATOM | 61 | CG | ARG | C | 750 | 20.752 | −16.104 | −31.106 | 1.00 | 85.77 | C |
| ATOM | 62 | CD | ARG | C | 750 | 22.121 | −16.701 | −31.339 | 1.00 | 79.21 | C |
| ATOM | 63 | NE | ARG | C | 750 | 22.046 | −18.149 | −31.170 | 1.00 | 86.81 | N |
| ATOM | 64 | CZ | ARG | C | 750 | 23.093 | −18.962 | −31.035 | 1.00 | 91.04 | C |
| ATOM | 65 | NH1 | ARG | C | 750 | 24.326 | −18.472 | −31.041 | 1.00 | 109.64 | N |
| ATOM | 66 | NH2 | ARG | C | 750 | 22.914 | −20.272 | −30.903 | 1.00 | 83.60 | N |
| ATOM | 67 | C | ARG | C | 750 | 18.565 | −13.576 | −32.764 | 1.00 | 74.44 | C |
| ATOM | 68 | O | ARG | C | 750 | 17.906 | −12.846 | −32.002 | 1.00 | 75.97 | O |
| ATOM | 69 | N | LYS | C | 751 | 19.035 | −13.185 | −33.951 | 1.00 | 66.12 | N |
| ATOM | 70 | CA | LYS | C | 751 | 18.756 | −11.847 | −34.470 | 1.00 | 61.01 | C |
| ATOM | 71 | CB | LYS | C | 751 | 19.497 | −11.571 | −35.801 | 1.00 | 51.19 | C |
| ATOM | 72 | C | LYS | C | 751 | 17.229 | −11.653 | −34.540 | 1.00 | 62.27 | C |
| ATOM | 73 | O | LYS | C | 751 | 16.679 | −10.834 | −33.794 | 1.00 | 61.37 | O |
| ATOM | 74 | N | ALA | C | 752 | 16.553 | −12.470 | −35.355 | 1.00 | 62.36 | N |
| ATOM | 75 | CA | ALA | C | 752 | 15.099 | −12.366 | −35.582 | 1.00 | 58.29 | C |
| ATOM | 76 | CB | ALA | C | 752 | 14.586 | −13.528 | −36.388 | 1.00 | 58.51 | C |
| ATOM | 77 | C | ALA | C | 752 | 14.305 | −12.287 | −34.329 | 1.00 | 57.74 | C |
| ATOM | 78 | O | ALA | C | 752 | 13.249 | −11.680 | −34.335 | 1.00 | 57.26 | O |
| ATOM | 79 | N | LEU | C | 753 | 14.809 | −12.884 | −33.252 | 1.00 | 58.72 | N |
| ATOM | 80 | CA | LEU | C | 753 | 14.177 | −12.708 | −31.959 | 1.00 | 64.81 | C |
| ATOM | 81 | CB | LEU | C | 753 | 14.858 | −13.543 | −30.903 | 1.00 | 63.92 | C |
| ATOM | 82 | CG | LEU | C | 753 | 14.133 | −14.882 | −30.757 | 1.00 | 64.45 | C |
| ATOM | 83 | CD1 | LEU | C | 753 | 14.938 | −15.892 | −29.938 | 1.00 | 60.54 | C |
| ATOM | 84 | CD2 | LEU | C | 753 | 12.734 | −14.687 | −30.190 | 1.00 | 58.51 | C |
| ATOM | 85 | C | LEU | C | 753 | 14.009 | −11.249 | −31.503 | 1.00 | 77.30 | C |
| ATOM | 86 | O | LEU | C | 753 | 13.056 | −10.946 | −30.796 | 1.00 | 71.00 | O |
| ATOM | 87 | N | MET | C | 754 | 14.910 | −10.348 | −31.908 | 1.00 | 89.88 | N |
| ATOM | 88 | CA | MET | C | 754 | 14.580 | −8.909 | −31.913 | 1.00 | 96.47 | C |
| ATOM | 89 | CB | MET | C | 754 | 14.871 | −8.222 | −30.574 | 1.00 | 105.54 | C |
| ATOM | 90 | CG | MET | C | 754 | 16.333 | −8.170 | −30.186 | 1.00 | 118.35 | C |
| ATOM | 91 | SD | MET | C | 754 | 16.916 | −9.746 | −29.548 | 1.00 | 127.08 | S |
| ATOM | 92 | CE | MET | C | 754 | 16.384 | −9.571 | −27.846 | 1.00 | 126.50 | C |
| ATOM | 93 | C | MET | C | 754 | 15.202 | −8.127 | −33.062 | 1.00 | 104.49 | C |
| ATOM | 94 | O | MET | C | 754 | 14.493 | −7.710 | −33.979 | 1.00 | 106.03 | O |
| ATOM | 95 | N | GLY | C | 755 | 16.524 | −7.949 | −32.997 | 1.00 | 121.99 | N |
| ATOM | 96 | CA | GLY | C | 755 | 17.307 | −7.116 | −33.927 | 1.00 | 118.97 | C |
| ATOM | 97 | C | GLY | C | 755 | 16.762 | −7.010 | −35.340 | 1.00 | 116.77 | C |
| ATOM | 98 | O | GLY | C | 755 | 16.031 | −6.069 | −35.661 | 1.00 | 116.42 | O |
| ATOM | 99 | N | SER | C | 756 | 17.105 | −7.986 | −36.174 | 1.00 | 106.56 | N |
| ATOM | 100 | CA | SER | C | 756 | 16.639 | −8.040 | −37.559 | 1.00 | 110.81 | C |
| ATOM | 101 | CB | SER | C | 756 | 17.092 | −9.356 | −38.202 | 1.00 | 114.09 | C |
| ATOM | 102 | OG | SER | C | 756 | 16.528 | −9.514 | −39.494 | 1.00 | 117.80 | O |
| ATOM | 103 | C | SER | C | 756 | 15.115 | −7.827 | −37.770 | 1.00 | 117.97 | C |
| ATOM | 104 | O | SER | C | 756 | 14.586 | −8.164 | −38.839 | 1.00 | 123.88 | O |
| ATOM | 105 | N | PHE | C | 757 | 14.425 | −7.282 | −36.761 | 1.00 | 116.00 | N |
| ATOM | 106 | CA | PHE | C | 757 | 12.999 | −6.883 | −36.857 | 1.00 | 120.77 | C |
| ATOM | 107 | CB | PHE | C | 757 | 12.868 | −5.458 | −37.434 | 1.00 | 130.68 | C |
| ATOM | 108 | CG | PHE | C | 757 | 11.510 | −4.817 | −37.223 | 1.00 | 134.39 | C |
| ATOM | 109 | CD1 | PHE | C | 757 | 10.491 | −4.956 | −38.177 | 1.00 | 138.03 | C |
| ATOM | 110 | CE1 | PHE | C | 757 | 9.248 | −4.362 | −37.990 | 1.00 | 133.12 | C |
| ATOM | 111 | CZ | PHE | C | 757 | 9.011 | −3.610 | −36.846 | 1.00 | 137.06 | C |
| ATOM | 112 | CE2 | PHE | C | 757 | 10.014 | −3.454 | −35.894 | 1.00 | 132.83 | C |
| ATOM | 113 | CD2 | PHE | C | 757 | 11.256 | −4.048 | −36.086 | 1.00 | 131.69 | C |
| ATOM | 114 | C | PHE | C | 757 | 12.130 | −7.862 | −37.651 | 1.00 | 107.91 | C |
| ATOM | 115 | O | PHE | C | 757 | 10.930 | −7.987 | −37.395 | 1.00 | 106.12 | O |
| ATOM | 116 | N | GLU | A | 244 | −18.325 | −25.540 | −26.704 | 1.00 | 95.16 | N |
| ATOM | 117 | CA | GLU | A | 244 | −18.073 | −26.244 | −25.400 | 1.00 | 101.28 | C |
| ATOM | 118 | CB | GLU | A | 244 | −18.336 | −27.763 | −25.573 | 1.00 | 99.29 | C |
| ATOM | 119 | CG | GLU | A | 244 | −17.696 | −28.716 | −24.565 | 1.00 | 100.52 | C |
| ATOM | 120 | CD | GLU | A | 244 | −18.378 | −28.717 | −23.208 | 1.00 | 100.97 | C |
| ATOM | 121 | OE1 | GLU | A | 244 | −19.216 | −27.823 | −22.947 | 1.00 | 106.04 | O |
| ATOM | 122 | OE2 | GLU | A | 244 | −18.070 | −29.617 | −22.395 | 1.00 | 95.65 | O |
| ATOM | 123 | C | GLU | A | 244 | −16.698 | −25.915 | −24.733 | 1.00 | 96.26 | C |
| ATOM | 124 | O | GLU | A | 244 | −16.376 | −26.425 | −23.654 | 1.00 | 91.42 | O |
| ATOM | 125 | N | LEU | A | 245 | −15.902 | −25.053 | −25.367 | 1.00 | 86.02 | N |
| ATOM | 126 | CA | LEU | A | 245 | −14.650 | −24.578 | −24.766 | 1.00 | 79.26 | C |
| ATOM | 127 | CB | LEU | A | 245 | −13.912 | −23.608 | −25.697 | 1.00 | 72.49 | C |
| ATOM | 128 | CG | LEU | A | 245 | −13.676 | −24.003 | −27.156 | 1.00 | 65.58 | C |
| ATOM | 129 | CD1 | LEU | A | 245 | −13.116 | −22.821 | −27.923 | 1.00 | 63.46 | C |
| ATOM | 130 | CD2 | LEU | A | 245 | −12.725 | −25.174 | −27.243 | 1.00 | 66.62 | C |
| ATOM | 131 | C | LEU | A | 245 | −14.915 | −23.858 | −23.453 | 1.00 | 85.34 | C |
| ATOM | 132 | O | LEU | A | 245 | −16.017 | −23.352 | −23.211 | 1.00 | 97.34 | O |
| ATOM | 133 | N | THR | A | 246 | −13.895 | −23.806 | −22.610 | 1.00 | 80.64 | N |
| ATOM | 134 | CA | THR | A | 246 | −13.954 | −23.015 | −21.405 | 1.00 | 71.62 | C |
| ATOM | 135 | CB | THR | A | 246 | −13.166 | −23.660 | −20.268 | 1.00 | 68.45 | C |
| ATOM | 136 | OG1 | THR | A | 246 | −11.815 | −23.194 | −20.318 | 1.00 | 71.61 | O |

APPENDIX 1-continued

| | | | | | | | | | | |
|---|---|---|---|---|---|---|---|---|---|---|
| ATOM | 137 | CG2 | THR | A | 246 | −13.194 | −25.166 | −20.379 | 1.00 | 66.14 C |
| ATOM | 138 | C | THR | A | 246 | −13.313 | −21.657 | −21.687 | 1.00 | 77.31 C |
| ATOM | 139 | O | THR | A | 246 | −12.360 | −21.573 | −22.461 | 1.00 | 71.90 O |
| ATOM | 155 | N | GLN | A | 249 | −9.922 | −21.529 | −22.706 | 1.00 | 70.74 N |
| ATOM | 156 | CA | GLN | A | 249 | −9.787 | −22.016 | −24.066 | 1.00 | 72.02 C |
| ATOM | 157 | CB | GLN | A | 249 | −10.566 | −23.323 | −24.241 | 1.00 | 70.29 C |
| ATOM | 158 | CG | GLN | A | 249 | −10.366 | −24.294 | −23.083 | 1.00 | 67.41 C |
| ATOM | 159 | CD | GLN | A | 249 | −10.995 | −25.663 | −23.314 | 1.00 | 73.99 C |
| ATOM | 160 | OE1 | GLN | A | 249 | −11.815 | −25.866 | −24.217 | 1.00 | 80.54 O |
| ATOM | 161 | NE2 | GLN | A | 249 | −10.606 | −26.612 | −22.496 | 1.00 | 70.10 N |
| ATOM | 162 | C | GLN | A | 249 | −10.201 | −20.962 | −25.100 | 1.00 | 68.00 C |
| ATOM | 163 | O | GLN | A | 249 | −9.379 | −20.577 | −25.918 | 1.00 | 66.11 O |
| ATOM | 164 | N | GLN | A | 250 | −11.455 | −20.490 | −25.047 | 1.00 | 70.12 N |
| ATOM | 165 | CA | GLN | A | 250 | −11.955 | −19.507 | −26.027 | 1.00 | 68.86 C |
| ATOM | 166 | CB | GLN | A | 250 | −13.415 | −19.106 | −25.789 | 1.00 | 63.79 C |
| ATOM | 167 | CG | GLN | A | 250 | −13.694 | −18.507 | −24.426 | 1.00 | 79.63 C |
| ATOM | 168 | CD | GLN | A | 250 | −14.867 | −17.520 | −24.406 | 1.00 | 85.93 C |
| ATOM | 169 | OE1 | GLN | A | 250 | −16.017 | −17.868 | −24.709 | 1.00 | 77.91 O |
| ATOM | 170 | NE2 | GLN | A | 250 | −14.572 | −16.274 | −24.026 | 1.00 | 89.83 N |
| ATOM | 171 | C | GLN | A | 250 | −11.050 | −18.285 | −26.135 | 1.00 | 68.81 C |
| ATOM | 172 | O | GLN | A | 250 | −10.808 | −17.754 | −27.242 | 1.00 | 69.99 O |
| ATOM | 173 | N | THR | A | 251 | −10.522 | −17.871 | −24.986 | 1.00 | 63.77 N |
| ATOM | 174 | CA | THR | A | 251 | −9.563 | −16.783 | −24.930 | 1.00 | 58.96 C |
| ATOM | 175 | CB | THR | A | 251 | −9.225 | −16.440 | −23.485 | 1.00 | 63.49 C |
| ATOM | 176 | OG1 | THR | A | 251 | −10.429 | −16.098 | −22.788 | 1.00 | 66.97 O |
| ATOM | 177 | CG2 | THR | A | 251 | −8.242 | −15.284 | −23.439 | 1.00 | 61.32 C |
| ATOM | 178 | C | THR | A | 251 | −8.283 | −17.139 | −25.655 | 1.00 | 59.05 C |
| ATOM | 179 | O | THR | A | 251 | −7.866 | −16.409 | −26.540 | 1.00 | 57.34 O |
| ATOM | 180 | N | LEU | A | 252 | −7.666 | −18.264 | −25.269 | 1.00 | 61.91 N |
| ATOM | 181 | CA | LEU | A | 252 | −6.488 | −18.792 | −25.958 | 1.00 | 56.00 C |
| ATOM | 182 | CB | LEU | A | 252 | −6.068 | −20.138 | −25.374 | 1.00 | 52.70 C |
| ATOM | 183 | CG | LEU | A | 252 | −4.775 | −20.857 | −25.817 | 1.00 | 54.52 C |
| ATOM | 184 | CD1 | LEU | A | 252 | −3.528 | −19.974 | −25.862 | 1.00 | 52.01 C |
| ATOM | 185 | CD2 | LEU | A | 252 | −4.499 | −22.045 | −24.907 | 1.00 | 52.94 C |
| ATOM | 186 | C | LEU | A | 252 | −6.736 | −18.932 | −27.465 | 1.00 | 60.72 C |
| ATOM | 187 | O | LEU | A | 252 | −5.851 | −18.608 | −28.264 | 1.00 | 61.91 O |
| ATOM | 188 | N | LEU | A | 253 | −7.933 | −19.381 | −27.850 | 1.00 | 56.02 N |
| ATOM | 189 | CA | LEU | A | 253 | −8.187 | −19.656 | −29.240 | 1.00 | 59.39 C |
| ATOM | 190 | CB | LEU | A | 253 | −9.485 | −20.449 | −29.472 | 1.00 | 64.88 C |
| ATOM | 191 | CG | LEU | A | 253 | −9.899 | −20.878 | −30.910 | 1.00 | 57.78 C |
| ATOM | 192 | CD1 | LEU | A | 253 | −8.724 | −21.139 | −31.849 | 1.00 | 48.72 C |
| ATOM | 193 | CD2 | LEU | A | 253 | −10.863 | −22.067 | −30.889 | 1.00 | 50.34 C |
| ATOM | 194 | C | LEU | A | 253 | −8.139 | −18.371 | −30.026 | 1.00 | 62.44 C |
| ATOM | 195 | O | LEU | A | 253 | −7.288 | −18.232 | −30.904 | 1.00 | 73.67 O |
| ATOM | 196 | N | HIS | A | 254 | −9.012 | −17.428 | −29.686 | 1.00 | 66.91 N |
| ATOM | 197 | CA | HIS | A | 254 | −8.997 | −16.065 | −30.256 | 1.00 | 60.28 C |
| ATOM | 198 | CB | HIS | A | 254 | −9.904 | −15.163 | −29.423 | 1.00 | 67.43 C |
| ATOM | 199 | CG | HIS | A | 254 | −10.138 | −13.804 | −30.030 | 1.00 | 85.22 C |
| ATOM | 200 | ND1 | HIS | A | 254 | −11.356 | −13.390 | −30.423 | 1.00 | 95.51 N |
| ATOM | 201 | CE1 | HIS | A | 254 | −11.259 | −12.136 | −30.924 | 1.00 | 108.55 C |
| ATOM | 202 | NE2 | HIS | A | 254 | −9.966 | −11.752 | −30.856 | 1.00 | 100.11 N |
| ATOM | 203 | CD2 | HIS | A | 254 | −9.250 | −12.751 | −30.308 | 1.00 | 92.23 C |
| ATOM | 204 | C | HIS | A | 254 | −7.610 | −15.455 | −30.386 | 1.00 | 55.25 C |
| ATOM | 205 | O | HIS | A | 254 | −7.232 | −14.945 | −31.443 | 1.00 | 50.40 O |
| ATOM | 206 | N | PHE | A | 255 | −6.823 | −15.506 | −29.322 | 1.00 | 54.31 N |
| ATOM | 207 | CA | PHE | A | 255 | −5.484 | −14.970 | −29.386 | 1.00 | 63.11 C |
| ATOM | 208 | CB | PHE | A | 255 | −4.757 | −15.177 | −28.053 | 1.00 | 70.70 C |
| ATOM | 209 | CG | PHE | A | 255 | −3.557 | −14.283 | −27.881 | 1.00 | 75.50 C |
| ATOM | 210 | CD1 | PHE | A | 255 | −3.681 | −13.033 | −27.286 | 1.00 | 77.17 C |
| ATOM | 211 | CE1 | PHE | A | 255 | −2.584 | −12.192 | −27.149 | 1.00 | 82.65 C |
| ATOM | 212 | CZ | PHE | A | 255 | −1.345 | −12.600 | −27.608 | 1.00 | 87.31 C |
| ATOM | 213 | CE2 | PHE | A | 255 | −1.208 | −13.848 | −28.197 | 1.00 | 87.35 C |
| ATOM | 214 | CD2 | PHE | A | 255 | −2.309 | −14.682 | −28.333 | 1.00 | 81.81 C |
| ATOM | 215 | C | PHE | A | 255 | −4.698 | −15.592 | −30.545 | 1.00 | 67.99 C |
| ATOM | 216 | O | PHE | A | 255 | −4.097 | −14.896 | −31.360 | 1.00 | 69.92 O |
| ATOM | 217 | N | ILE | A | 256 | −4.736 | −16.918 | −30.624 | 1.00 | 76.76 N |
| ATOM | 218 | CA | ILE | A | 256 | −3.997 | −17.650 | −31.642 | 1.00 | 66.02 C |
| ATOM | 219 | CB | ILE | A | 256 | −4.103 | −19.180 | −31.465 | 1.00 | 62.35 C |
| ATOM | 220 | CG1 | ILE | A | 256 | −3.790 | −19.608 | −30.018 | 1.00 | 57.61 C |
| ATOM | 221 | CD1 | ILE | A | 256 | −2.455 | −19.134 | −29.485 | 1.00 | 54.28 C |
| ATOM | 222 | CG2 | ILE | A | 256 | −3.146 | −19.869 | −32.432 | 1.00 | 68.80 C |
| ATOM | 223 | C | ILE | A | 256 | −4.451 | −17.237 | −33.033 | 1.00 | 63.36 C |
| ATOM | 224 | O | ILE | A | 256 | −3.632 | −16.795 | −33.842 | 1.00 | 65.01 O |
| ATOM | 225 | N | MET | A | 257 | −5.753 | −17.368 | −33.295 | 1.00 | 58.44 N |
| ATOM | 226 | CA | MET | A | 257 | −6.351 | −16.964 | −34.571 | 1.00 | 59.19 C |
| ATOM | 227 | CB | MET | A | 257 | −7.866 | −16.961 | −34.458 | 1.00 | 60.01 C |
| ATOM | 228 | CG | MET | A | 257 | −8.512 | −18.308 | −34.750 | 1.00 | 71.78 C |
| ATOM | 229 | SD | MET | A | 257 | −7.679 | −19.356 | −35.974 | 1.00 | 79.41 S |
| ATOM | 230 | CE | MET | A | 257 | −7.641 | −18.326 | −37.462 | 1.00 | 66.46 C |
| ATOM | 231 | C | MET | A | 257 | −5.884 | −15.597 | −35.067 | 1.00 | 68.24 C |

APPENDIX 1-continued

| | | | | | | | | | | |
|---|---|---|---|---|---|---|---|---|---|---|
| ATOM | 232 | O | MET | A | 257 | −5.263 | −15.483 | −36.139 | 1.00 | 67.00 O |
| ATOM | 233 | N | ASP | A | 258 | −6.219 | −14.577 | −34.269 | 1.00 | 70.44 N |
| ATOM | 234 | CA | ASP | A | 258 | −5.693 | −13.221 | −34.348 | 1.00 | 63.65 C |
| ATOM | 235 | CB | ASP | A | 258 | −5.765 | −12.619 | −32.946 | 1.00 | 72.46 C |
| ATOM | 236 | CG | ASP | A | 258 | −6.322 | −11.179 | −32.923 | 1.00 | 83.30 C |
| ATOM | 237 | OD1 | ASP | A | 258 | −7.393 | −10.904 | −33.558 | 1.00 | 74.31 O |
| ATOM | 238 | OD2 | ASP | A | 258 | −5.684 | −10.345 | −32.219 | 1.00 | 74.91 O |
| ATOM | 239 | C | ASP | A | 258 | −4.247 | −13.175 | −34.833 | 1.00 | 64.43 C |
| ATOM | 240 | O | ASP | A | 258 | −3.915 | −12.466 | −35.825 | 1.00 | 62.93 O |
| ATOM | 241 | N | SER | A | 259 | −3.392 | −13.936 | −34.141 | 1.00 | 58.22 N |
| ATOM | 242 | CA | SER | A | 259 | −1.959 | −13.889 | −34.403 | 1.00 | 61.61 C |
| ATOM | 243 | CB | SER | A | 259 | −1.171 | −14.453 | −33.242 | 1.00 | 60.41 C |
| ATOM | 244 | OG | SER | A | 259 | −1.833 | −14.177 | −32.038 | 1.00 | 65.05 O |
| ATOM | 245 | C | SER | A | 259 | −1.593 | −14.640 | −35.649 | 1.00 | 67.47 C |
| ATOM | 246 | O | SER | A | 259 | −0.703 | −14.218 | −36.382 | 1.00 | 87.04 O |
| ATOM | 247 | N | TYR | A | 260 | −2.282 | −15.751 | −35.891 | 1.00 | 66.41 N |
| ATOM | 248 | CA | TYR | A | 260 | −2.053 | −16.556 | −37.075 | 1.00 | 65.84 C |
| ATOM | 249 | CB | TYR | A | 260 | −2.831 | −17.875 | −36.986 | 1.00 | 66.79 C |
| ATOM | 250 | CG | TYR | A | 260 | −2.453 | −18.880 | −38.044 | 1.00 | 61.65 C |
| ATOM | 251 | CD1 | TYR | A | 260 | −1.137 | −19.322 | −38.162 | 1.00 | 66.20 C |
| ATOM | 252 | CE1 | TYR | A | 260 | −0.764 | −20.228 | −39.144 | 1.00 | 69.32 C |
| ATOM | 253 | CZ | TYR | A | 260 | −1.721 | −20.702 | −40.013 | 1.00 | 72.88 C |
| ATOM | 254 | OH | TYR | A | 260 | −1.315 | −21.606 | −40.964 | 1.00 | 88.07 O |
| ATOM | 255 | CE2 | TYR | A | 260 | −3.045 | −20.282 | −39.924 | 1.00 | 62.54 C |
| ATOM | 256 | CD2 | TYR | A | 260 | −3.404 | −19.384 | −38.934 | 1.00 | 58.02 C |
| ATOM | 257 | C | TYR | A | 260 | −2.455 | −15.778 | −38.301 | 1.00 | 72.22 C |
| ATOM | 258 | O | TYR | A | 260 | −1.938 | −16.011 | −39.380 | 1.00 | 84.34 O |
| ATOM | 259 | N | ASN | A | 261 | −3.355 | −14.818 | −38.121 | 1.00 | 84.01 N |
| ATOM | 260 | CA | ASN | A | 261 | −3.862 | −14.003 | −39.222 | 1.00 | 84.78 C |
| ATOM | 261 | CB | ASN | A | 261 | −5.254 | −13.491 | −38.883 | I.00 | 78.70 C |
| ATOM | 262 | CG | ASN | A | 261 | −6.327 | −14.540 | −39.109 | 1.00 | 89.69 C |
| ATOM | 263 | OD1 | ASN | A | 261 | −7.489 | −14.206 | −39.353 | 1.00 | 95.40 O |
| ATOM | 264 | ND2 | ASN | A | 261 | −5.944 | −15.816 | −39.061 | 1.00 | 89.29 N |
| ATOM | 265 | C | ASN | A | 261 | −2.989 | −12.856 | −39.723 | 1.00 | 90.69 C |
| ATOM | 266 | O | ASN | A | 261 | −2.962 | −12.600 | −40.925 | 1.00 | 97.65 O |
| ATOM | 267 | N | LYS | A | 262 | −2.292 | −12.164 | −38.819 | 1.00 | 99.07 N |
| ATOM | 268 | CA | LYS | A | 262 | −1.544 | −10.938 | −39.174 | 1.00 | 115.04 C |
| ATOM | 269 | CB | LYS | A | 262 | −0.854 | −10.327 | −37.938 | 1.00 | 127.18 C |
| ATOM | 270 | CG | LYS | A | 262 | −1.764 | −9.527 | −37.004 | 1.00 | 123.16 C |
| ATOM | 271 | CD | LYS | A | 262 | −0.986 | −8.972 | −35.809 | 1.00 | 109.97 C |
| ATOM | 272 | CE | LYS | A | 262 | −1.905 | −8.608 | −34.646 | 1.00 | 104.09 C |
| ATOM | 273 | NZ | LYS | A | 262 | −2.355 | −7.184 | −34.641 | 1.00 | 101.50 N |
| ATOM | 274 | C | LYS | A | 262 | −0.516 | −11.133 | −40.292 | 1.00 | 122.59 C |
| ATOM | 275 | O | LYS | A | 262 | 0.115 | −10.174 | −40.739 | 1.00 | 127.12 O |
| ATOM | 276 | N | GLN | A | 263 | −0.356 | −12.381 | −40.730 | 1.00 | 132.27 N |
| ATOM | 277 | CA | GLN | A | 263 | 0.559 | −12.749 | −41.814 | 1.00 | 123.34 C |
| ATOM | 278 | CB | GLN | A | 263 | 1.392 | −13.970 | −41.396 | 1.00 | 125.96 C |
| ATOM | 279 | CG | GLN | A | 263 | 0.611 | −15.072 | −40.677 | 1.00 | 130.55 C |
| ATOM | 280 | CD | GLN | A | 263 | 1.177 | −15.439 | −39.305 | 1.00 | 129.11 C |
| ATOM | 281 | OE1 | GLN | A | 263 | 1.676 | −16.555 | −39.094 | 1.00 | 117.78 O |
| ATOM | 282 | NE2 | GLN | A | 263 | 1.094 | −14.500 | −38.363 | 1.00 | 124.45 N |
| ATOM | 283 | C | GLN | A | 263 | −0.192 | −12.979 | −43.140 | 1.00 | 124.40 C |
| ATOM | 284 | O | GLN | A | 263 | −0.897 | −13.984 | −43.310 | 1.00 | 115.00 O |
| ATOM | 285 | N | ARG | A | 264 | −0.038 | −12.023 | −44.063 | 1.00 | 132.30 N |
| ATOM | 286 | CA | ARG | A | 264 | −0.781 | −11.978 | −45.343 | 1.00 | 129.94 C |
| ATOM | 287 | CB | ARG | A | 264 | −1.708 | −10.737 | −45.403 | 1.00 | 127.72 C |
| ATOM | 288 | CG | ARG | A | 264 | −2.281 | −10.214 | −44.079 | 1.00 | 119.54 C |
| ATOM | 289 | CD | ARG | A | 264 | −1.470 | −9.012 | −43.608 | 1.00 | 118.18 C |
| ATOM | 290 | NE | ARG | A | 264 | −1.869 | −8.480 | −42.307 | 1.00 | 116.51 N |
| ATOM | 291 | CZ | ARG | A | 264 | −1.100 | −7.689 | −41.556 | 1.00 | 117.13 C |
| ATOM | 292 | NH1 | ARG | A | 264 | 0.123 | −7.354 | −41.963 | 1.00 | 104.97 N |
| ATOM | 293 | NH2 | ARG | A | 264 | −1.542 | −7.246 | −40.383 | 1.00 | 113.28 N |
| ATOM | 294 | C | ARG | A | 264 | 0.188 | −12.123 | −46.571 | 1.00 | 127.91 C |
| ATOM | 295 | O | ARG | A | 264 | 1.012 | −13.046 | −46.557 | 1.00 | 115.47 O |
| ATOM | 296 | N | ALA | A | 265 | 0.118 | −11.311 | −47.640 | 1.00 | 127.10 N |
| ATOM | 297 | CA | ALA | A | 265 | −0.948 | −10.368 | −47.997 | 1.00 | 129.76 C |
| ATOM | 298 | CB | ALA | A | 265 | −0.353 | −9.008 | −48.347 | 1.00 | 117.15 C |
| ATOM | 299 | C | ALA | A | 265 | −1.676 | −10.955 | −49.206 | 1.00 | 134.71 C |
| ATOM | 300 | O | ALA | A | 265 | −1.384 | −10.566 | −50.344 | 1.00 | 119.71 O |
| ATOM | 301 | N | PRO | A | 266 | −2.650 | −11.870 | −48.959 | 1.00 | 150.65 N |
| ATOM | 302 | CA | PRO | A | 266 | −3.128 | −12.910 | −49.900 | 1.00 | 152.52 C |
| ATOM | 303 | CB | PRO | A | 266 | −4.425 | −13.414 | −49.249 | 1.00 | 160.97 C |
| ATOM | 304 | CG | PRO | A | 266 | −4.864 | −12.301 | −48.359 | 1.00 | 163.35 C |
| ATOM | 305 | CD | PRO | A | 266 | −3.587 | −11.712 | −47.831 | 1.00 | 155.40 C |
| ATOM | 306 | C | PRO | A | 266 | −3.411 | −12.396 | −51.303 | 1.00 | 149.59 C |
| ATOM | 307 | O | PRO | A | 266 | −3.525 | −13.184 | −52.248 | 1.00 | 146.68 O |
| ATOM | 308 | N | GLN | A | 267 | −3.538 | −11.078 | −51.409 | 1.00 | 138.45 N |
| ATOM | 309 | CA | GLN | A | 267 | −3.607 | −10.396 | −52.678 | 1.00 | 131.68 C |
| ATOM | 310 | CB | GLN | A | 267 | −3.642 | −8.878 | −52.438 | 1.00 | 140.27 C |
| ATOM | 311 | CG | GLN | A | 267 | −4.150 | −8.038 | −53.601 | 1.00 | 138.05 C |

APPENDIX 1-continued

| | | | | | | | | | | |
|---|---|---|---|---|---|---|---|---|---|---|
| ATOM | 312 | CD | GLN | A | 267 | −3.036 | −7.618 | −54.546 | 1.00 | 145.63 C |
| ATOM | 313 | OE1 | GLN | A | 267 | −2.003 | −7.089 | −54.120 | 1.00 | 140.46 O |
| ATOM | 314 | NE2 | GLN | A | 267 | −3.244 | −7.848 | −55.839 | 1.00 | 152.12 N |
| ATOM | 315 | C | GLN | A | 267 | −2.415 | −10.830 | −53.539 | 1.00 | 121.93 C |
| ATOM | 316 | O | GLN | A | 267 | −2.587 | −11.638 | −54.452 | 1.00 | 116.81 O |
| ATOM | 317 | N | GLU | A | 268 | −1.208 | −10.351 | −53.231 | 1.00 | 119.78 N |
| ATOM | 318 | CA | GLU | A | 268 | −0.061 | −10.593 | −54.129 | 1.00 | 125.48 C |
| ATOM | 319 | CB | GLU | A | 268 | 0.928 | −9.392 | −54.144 | 1.00 | 112.97 C |
| ATOM | 320 | CG | GLU | A | 268 | 2.219 | −9.514 | −53.339 | 1.00 | 106.41 C |
| ATOM | 321 | CD | GLU | A | 268 | 2.087 | −10.412 | −52.126 | 1.00 | 104.30 C |
| ATOM | 322 | OE1 | GLU | A | 268 | 0.975 | −10.450 | −51.531 | 1.00 | 98.89 O |
| ATOM | 323 | OE2 | GLU | A | 268 | 3.095 | −11.088 | −51.790 | 1.00 | 93.62 O |
| ATOM | 324 | C | GLU | A | 268 | 0.590 | −11.983 | −53.911 | 1.00 | 124.23 C |
| ATOM | 325 | O | GLU | A | 268 | 1.667 | −12.297 | −54.433 | 1.00 | 125.70 O |
| ATOM | 326 | N | ALA | A | 269 | −0.094 | −12.809 | −53.129 | 1.00 | 115.97 N |
| ATOM | 327 | CA | ALA | A | 269 | 0.129 | −14.235 | −53.165 | 1.00 | 108.38 C |
| ATOM | 328 | CB | ALA | A | 269 | −0.625 | −14.907 | −52.030 | 1.00 | 110.59 C |
| ATOM | 329 | C | ALA | A | 269 | −0.345 | −14.750 | −54.534 | 1.00 | 107.90 C |
| ATOM | 330 | O | ALA | A | 269 | −0.140 | −15.921 | −54.883 | 1.00 | 99.12 O |
| ATOM | 331 | N | ALA | A | 270 | −0.983 | −13.856 | −55.298 | 1.00 | 109.25 N |
| ATOM | 332 | CA | ALA | A | 270 | −1.369 | −14.127 | −56.681 | 1.00 | 107.03 C |
| ATOM | 333 | CB | ALA | A | 270 | −2.531 | −13.247 | −57.105 | 1.00 | 100.51 C |
| ATOM | 334 | C | ALA | A | 270 | −0.170 | −13.920 | −57.596 | 1.00 | 109.39 C |
| ATOM | 335 | O | ALA | A | 270 | −0.025 | −14.615 | −58.606 | 1.00 | 107.46 O |
| ATOM | 336 | N | ASN | A | 271 | 0.689 | −12.966 | −57.234 | 1.00 | 114.24 N |
| ATOM | 337 | CA | ASN | A | 271 | 1.976 | −12.763 | −57.920 | 1.00 | 112.80 C |
| ATOM | 338 | CB | ASN | A | 271 | 2.775 | −11.606 | −57.271 | 1.00 | 112.16 C |
| ATOM | 339 | CG | ASN | A | 271 | 4.195 | −11.463 | −57.830 | 1.00 | 119.82 C |
| ATOM | 340 | OD1 | ASN | A | 271 | 4.402 | −11.324 | −59.046 | 1.00 | 114.47 O |
| ATOM | 341 | ND2 | ASN | A | 271 | 5.183 | −11.483 | −56.933 | 1.00 | 115.46 N |
| ATOM | 342 | C | ASN | A | 271 | 2.796 | −14.061 | −57.969 | 1.00 | 98.58 C |
| ATOM | 343 | O | ASN | A | 271 | 3.546 | −14.291 | −58.926 | 1.00 | 97.96 O |
| ATOM | 344 | N | ALA | A | 272 | 2.635 | −14.898 | −56.938 | 1.00 | 88.05 N |
| ATOM | 345 | CA | ALA | A | 272 | 3.300 | −16.199 | −56.862 | 1.00 | 85.04 C |
| ATOM | 346 | CB | ALA | A | 272 | 3.707 | −16.516 | −55.436 | 1.00 | 77.63 C |
| ATOM | 347 | C | ALA | A | 272 | 2.432 | −17.313 | −57.435 | 1.00 | 87.63 C |
| ATOM | 348 | O | ALA | A | 272 | 2.950 | −18.332 | −57.903 | 1.00 | 95.95 O |
| ATOM | 349 | N | ALA | A | 273 | 1.116 | −17.112 | −57.396 | 1.00 | 93.09 N |
| ATOM | 350 | CA | ALA | A | 273 | 0.167 | −18.060 | −57.970 | 1.00 | 100.97 C |
| ATOM | 351 | CB | ALA | A | 273 | −1.247 | −17.771 | −57.482 | 1.00 | 108.89 C |
| ATOM | 352 | C | ALA | A | 273 | 0.241 | −18.050 | −59.500 | 1.00 | 106.49 C |
| ATOM | 353 | O | ALA | A | 273 | 0.993 | −18.834 | −60.089 | 1.00 | 115.25 O |
| ATOM | 354 | N | ALA | A | 274 | −0.527 | −17.164 | −60.142 | 1.00 | 118.27 N |
| ATOM | 355 | CA | ALA | A | 274 | −0.486 | −17.048 | −61.604 | 1.00 | 111.38 C |
| ATOM | 356 | CB | ALA | A | 274 | −1.829 | −16.595 | −62.165 | 1.00 | 103.45 C |
| ATOM | 357 | C | ALA | A | 274 | 0.651 | −16.148 | −62.093 | 1.00 | 105.32 C |
| ATOM | 358 | O | ALA | A | 274 | 1.300 | −15.446 | −61.308 | 1.00 | 96.60 O |
| ATOM | 359 | N | LYS | A | 275 | 0.866 | −16.183 | −63.404 | 1.00 | 105.29 N |
| ATOM | 360 | CA | LYS | A | 275 | 2.003 | −15.558 | −64.061 | 1.00 | 105.91 C |
| ATOM | 361 | CB | LYS | A | 275 | 1.806 | −14.048 | −64.228 | 1.00 | 117.63 C |
| ATOM | 362 | CG | LYS | A | 275 | 2.729 | −13.393 | −65.252 | 1.00 | 118.40 C |
| ATOM | 363 | CD | LYS | A | 275 | 2.768 | −11.889 | −65.029 | 1.00 | 115.55 C |
| ATOM | 364 | CE | LYS | A | 275 | 3.557 | −11.173 | −66.107 | 1.00 | 112.60 C |
| ATOM | 365 | NZ | LYS | A | 275 | 3.762 | −9.754 | −65.709 | 1.00 | 108.50 N |
| ATOM | 366 | C | LYS | A | 275 | 3.297 | −15.889 | −63.332 | 1.00 | 103.87 C |
| ATOM | 367 | O | LYS | A | 275 | 3.823 | −15.092 | −62.554 | 1.00 | 100.28 O |
| ATOM | 368 | N | GLU | A | 276 | 3.760 | −17.110 | −63.561 | 1.00 | 108.80 N |
| ATOM | 369 | CA | GLU | A | 276 | 5.133 | −17.509 | −63.273 | 1.00 | 111.99 C |
| ATOM | 370 | CB | GLU | A | 276 | 5.278 | −18.162 | −61.885 | 1.00 | 112.59 C |
| ATOM | 371 | CG | GLU | A | 276 | 5.269 | −17.185 | −60.704 | 1.00 | 98.17 C |
| ATOM | 372 | CD | GLU | A | 276 | 6.420 | −16.180 | −60.719 | 1.00 | 94.70 C |
| ATOM | 373 | OE1 | GLU | A | 276 | 7.516 | −16.507 | −61.253 | 1.00 | 77.13 O |
| ATOM | 374 | OE2 | GLU | A | 276 | 6.221 | −15.061 | −60.183 | 1.00 | 86.67 O |
| ATOM | 375 | C | GLU | A | 276 | 5.550 | −18.463 | −64.375 | 1.00 | 104.30 C |
| ATOM | 376 | O | GLU | A | 276 | 4.955 | −18.460 | −65.454 | 1.00 | 104.04 O |
| ATOM | 377 | N | PHE | A | 278 | 7.055 | −15.266 | −64.815 | 1.00 | 140.26 N |
| ATOM | 378 | CA | PHE | A | 278 | 8.510 | −15.178 | −64.733 | 1.00 | 141.37 C |
| ATOM | 379 | CB | PHF | A | 278 | 8.954 | −13.933 | −63.941 | 1.00 | 144.78 C |
| ATOM | 380 | CG | PHE | A | 278 | 8.144 | −12.683 | −64.193 | 1.00 | 154.75 C |
| ATOM | 381 | CD1 | PHE | A | 278 | 7.601 | −12.396 | −65.450 | 1.00 | 155.25 C |
| ATOM | 382 | CE1 | PHE | A | 278 | 6.871 | −11.233 | −65.646 | 1.00 | 154.54 C |
| ATOM | 383 | CZ | PHE | A | 278 | 6.693 | −10.330 | −64.594 | 1.00 | 147.84 C |
| ATOM | 384 | CE2 | PHE | A | 278 | 7.242 | −10.592 | −63.346 | 1.00 | 151.53 C |
| ATOM | 385 | CD2 | PHE | A | 278 | 7.968 | −11.757 | −63.153 | 1.00 | 158.31 C |
| ATOM | 386 | C | PHE | A | 278 | 9.094 | −16.420 | −64.044 | 1.00 | 134.30 C |
| ATOM | 387 | O | PHE | A | 278 | 9.234 | −16.431 | −62.818 | 1.00 | 139.39 O |
| ATOM | 388 | N | SER | A | 279 | 9.466 | −17.443 | −64.820 | 1.00 | 121.35 N |
| ATOM | 389 | CA | SER | A | 279 | 9.854 | −18.748 | −64.245 | 1.00 | 112.11 C |
| ATOM | 390 | CB | SER | A | 279 | 8.917 | −19.840 | −64.763 | 1.00 | 113.62 C |
| ATOM | 391 | OG | SER | A | 279 | 7.579 | −19.527 | −64.427 | 1.00 | 113.92 O |

APPENDIX 1-continued

| | | | | | | | | | | |
|---|---|---|---|---|---|---|---|---|---|---|
| ATOM | 392 | C | SER | A | 279 | 11.329 | −19.183 | −64.388 | 1.00 | 102.09 C |
| ATOM | 393 | O | SER | A | 279 | 12.165 | −18.422 | −64.887 | 1.00 | 101.57 O |
| ATOM | 394 | N | ALA | A | 280 | 11.611 | −20.417 | −63.950 | 1.00 | 92.83 N |
| ATOM | 395 | CA | ALA | A | 280 | 12.963 | −20.987 | −63.824 | 1.00 | 84.34 C |
| ATOM | 396 | CB | ALA | A | 280 | 13.676 | −21.026 | −65.161 | 1.00 | 96.16 C |
| ATOM | 397 | C | ALA | A | 280 | 13.793 | −20.253 | −62.779 | 1.00 | 85.65 C |
| ATOM | 398 | O | ALA | A | 280 | 13.285 | −19.927 | −61.717 | 1.00 | 90.92 O |
| ATOM | 399 | N | GLU | A | 281 | 15.066 | −19.998 | −63.067 | 1.00 | 90.94 N |
| ATOM | 400 | CA | GLU | A | 281 | 15.972 | −19.302 | −62.128 | 1.00 | 89.85 C |
| ATOM | 401 | CB | GLU | A | 281 | 17.341 | −18.999 | −62.766 | 1.00 | 85.75 C |
| ATOM | 402 | CG | GLU | A | 281 | 17.772 | −19.897 | −63.923 | 1.00 | 91.98 C |
| ATOM | 403 | CD | GLU | A | 281 | 17.132 | −19.539 | −65.269 | 1.00 | 97.70 C |
| ATOM | 404 | OE1 | GLU | A | 281 | 16.410 | −18.515 | −65.365 | 1.00 | 96.11 O |
| ATOM | 405 | OE2 | GLU | A | 281 | 17.340 | −20.301 | −66.247 | 1.00 | 99.07 O |
| ATOM | 406 | C | GLU | A | 281 | 15.370 | −17.993 | −61.575 | 1.00 | 88.23 C |
| ATOM | 407 | O | GLU | A | 281 | 15.892 | −17.411 | −60.620 | 1.00 | 86.47 O |
| ATOM | 408 | N | GLU | A | 282 | 14.288 | −17.520 | −62.189 | 1.00 | 87.96 N |
| ATOM | 409 | CA | GLU | A | 282 | 13.575 | −16.365 | −61.663 | 1.00 | 87.97 C |
| ATOM | 410 | CB | GLU | A | 282 | 12.500 | −15.890 | −62.635 | 1.00 | 91.23 C |
| ATOM | 411 | CG | GLU | A | 282 | 13.048 | −15.308 | −63.928 | 1.00 | 105.43 C |
| ATOM | 412 | CD | GLU | A | 282 | 12.089 | −14.314 | −64.566 | 1.00 | 118.44 C |
| ATOM | 413 | OE1 | GLU | A | 282 | 11.763 | −13.296 | −63.915 | 1.00 | 118.34 O |
| ATOM | 414 | OE2 | GLU | A | 282 | 11.659 | −14.539 | −65.721 | 1.00 | 124.25 O |
| ATOM | 415 | C | GLU | A | 282 | 12.953 | −16.826 | −60.376 | 1.00 | 78.42 C |
| ATOM | 416 | O | GLU | A | 282 | 13.403 | −16.472 | −59.297 | 1.00 | 72.59 O |
| ATOM | 417 | N | ASN | A | 283 | 11.918 | −17.640 | −60.543 | 1.00 | 84.63 N |
| ATOM | 418 | CA | ASN | A | 283 | 11.330 | −18.527 | −59.536 | 1.00 | 79.24 C |
| ATOM | 419 | CB | ASN | A | 283 | 10.810 | −19.770 | −60.265 | 1.00 | 77.40 C |
| ATOM | 420 | CG | ASN | A | 283 | 10.048 | −20.715 | −59.369 | 1.00 | 78.83 C |
| ATOM | 421 | OD1 | ASN | A | 283 | 8.993 | −20.369 | −58.838 | 1.00 | 82.39 O |
| ATOM | 422 | ND2 | ASN | A | 283 | 10.559 | −21.936 | −59.232 | 1.00 | 71.64 N |
| ATOM | 423 | C | ASN | A | 283 | 12.210 | −18.928 | −58.339 | 1.00 | 79.44 C |
| ATOM | 424 | O | ASN | A | 283 | 11.727 | −18.876 | −57.210 | 1.00 | 89.20 O |
| ATOM | 425 | N | PHE | A | 284 | 13.470 | −19.326 | −58.567 | 1.00 | 71.11 N |
| ATOM | 426 | CA | PHE | A | 284 | 14.427 | −19.546 | −57.465 | 1.00 | 72.23 C |
| ATOM | 427 | CB | PHE | A | 284 | 15.833 | −19.774 | −58.035 | 1.00 | 77.60 C |
| ATOM | 428 | CG | PHE | A | 284 | 16.854 | −20.257 | −57.032 | 1.00 | 76.28 C |
| ATOM | 429 | CD1 | PHE | A | 284 | 17.001 | −19.662 | −55.801 | 1.00 | 72.00 C |
| ATOM | 430 | CE1 | PHE | A | 284 | 17.954 | −20.116 | −54.895 | 1.00 | 74.65 C |
| ATOM | 431 | CZ | PHE | A | 284 | 18.791 | −21.163 | −55.217 | 1.00 | 72.20 C |
| ATOM | 432 | CE2 | PHE | A | 284 | 18.671 | −21.762 | −56.453 | 1.00 | 84.26 C |
| ATOM | 433 | CD2 | PHE | A | 284 | 17.712 | −21.304 | −57.358 | 1.00 | 87.48 C |
| ATOM | 434 | C | PHE | A | 284 | 14.444 | −18.315 | −56.549 | 1.00 | 81.18 C |
| ATOM | 435 | O | PHE | A | 284 | 14.144 | −18.402 | −55.356 | 1.00 | 78.49 O |
| ATOM | 436 | N | LEU | A | 285 | 14.769 | −17.170 | −57.154 | 1.00 | 93.53 N |
| ATOM | 437 | CA | LEU | A | 285 | 15.046 | −15.915 | −56.469 | 1.00 | 85.95 C |
| ATOM | 438 | CB | LEU | A | 285 | 15.429 | −14.822 | −57.487 | 1.00 | 88.31 C |
| ATOM | 439 | CG | LEU | A | 285 | 16.613 | −13.921 | −57.087 | 1.00 | 96.45 C |
| ATOM | 440 | CD1 | LEU | A | 285 | 17.708 | −14.737 | −56.417 | 1.00 | 98.87 C |
| ATOM | 441 | CD2 | LEU | A | 285 | 17.211 | −13.145 | −58.257 | 1.00 | 102.19 C |
| ATOM | 442 | C | LEU | A | 285 | 13.864 | −15.475 | −55.642 | 1.00 | 85.35 C |
| ATOM | 443 | O | LEU | A | 285 | 14.025 | −14.886 | −54.571 | 1.00 | 95.25 O |
| ATOM | 444 | N | ILE | A | 286 | 12.670 | −15.765 | −56.132 | 1.00 | 80.06 N |
| ATOM | 445 | CA | ILE | A | 286 | 11.473 | −15.407 | −55.386 | 1.00 | 90.54 C |
| ATOM | 446 | CB | ILE | A | 286 | 10.216 | −15.334 | −56.286 | 1.00 | 91.89 C |
| ATOM | 447 | CG1 | ILE | A | 286 | 10.165 | −13.950 | −56.964 | 1.00 | 81.12 C |
| ATOM | 448 | CD1 | ILE | A | 286 | 8.850 | −13.626 | −57.640 | 1.00 | 85.33 C |
| ATOM | 449 | CG2 | ILE | A | 286 | 8.951 | −15.657 | −55.491 | 1.00 | 84.91 C |
| ATOM | 450 | C | ILE | A | 286 | 11.283 | −16.271 | −54.131 | 1.00 | 93.99 C |
| ATOM | 451 | O | ILE | A | 286 | 11.092 | −15.730 | −53.038 | 1.00 | 100.04 O |
| ATOM | 452 | N | LEU | A | 287 | 11.366 | −17.595 | −54.285 | 1.00 | 85.53 N |
| ATOM | 453 | CA | LEU | A | 287 | 11.288 | −18.513 | −53.151 | 1.00 | 71.91 C |
| ATOM | 454 | CB | LEU | A | 287 | 11.526 | −19.931 | −53.603 | 1.00 | 67.48 C |
| ATOM | 455 | CG | LEU | A | 287 | 10.463 | −20.454 | −54.538 | 1.00 | 65.28 C |
| ATOM | 456 | CD1 | LEU | A | 287 | 11.056 | −21.651 | −55.272 | 1.00 | 69.35 C |
| ATOM | 457 | CD2 | LEU | A | 287 | 9.213 | −20.798 | −53.744 | 1.00 | 57.94 C |
| ATOM | 458 | C | LEU | A | 287 | 12.307 | −18.162 | −52.099 | 1.00 | 72.99 C |
| ATOM | 459 | O | LEU | A | 287 | 11.935 | −17.834 | −50.982 | 1.00 | 76.16 O |
| ATOM | 460 | N | THR | A | 288 | 13.591 | −18.214 | −52.454 | 1.00 | 71.57 N |
| ATOM | 461 | CA | THR | A | 288 | 14.642 | −17.810 | −51.517 | 1.00 | 72.32 C |
| ATOM | 462 | CB | THR | A | 288 | 15.979 | −17.502 | −52.207 | 1.00 | 69.94 C |
| ATOM | 463 | OG1 | THR | A | 288 | 15.773 | −17.477 | −53.619 | 1.00 | 77.96 O |
| ATOM | 464 | CG2 | THR | A | 288 | 16.996 | −18.580 | −51.898 | 1.00 | 64.56 C |
| ATOM | 465 | C | THR | A | 288 | 14.193 | −16.629 | −50.676 | 1.00 | 69.95 C |
| ATOM | 466 | O | THR | A | 288 | 14.423 | −16.614 | −49.469 | 1.00 | 71.59 O |
| ATOM | 467 | N | ALA | A | 289 | 13.518 | −15.665 | −51.300 | 1.00 | 70.83 N |
| ATOM | 468 | CA | ALA | A | 289 | 12.961 | −14.536 | −50.554 | 1.00 | 73.78 C |
| ATOM | 469 | CB | ALA | A | 289 | 12.466 | −13.445 | −51.488 | 1.00 | 76.74 C |
| ATOM | 470 | C | ALA | A | 289 | 11.841 | −15.018 | −49.650 | 1.00 | 68.56 C |
| ATOM | 471 | O | ALA | A | 289 | 11.990 | −15.019 | −48.443 | 1.00 | 66.45 O |

APPENDIX 1-continued

| | | | | | | | | | | |
|---|---|---|---|---|---|---|---|---|---|---|
| ATOM | 472 | N | MET | A | 290 | 10.728 | −15.414 | −50.260 | 1.00 | 72.99 N |
| ATOM | 473 | CA | MET | A | 290 | 9.598 | −16.084 | −49.607 | 1.00 | 74.60 C |
| ATOM | 474 | CB | MET | A | 290 | 8.920 | −16.983 | −50.628 | 1.00 | 81.05 C |
| ATOM | 475 | CG | MET | A | 290 | 8.256 | −16.225 | −51.759 | 1.00 | 84.99 C |
| ATOM | 476 | SD | MET | A | 290 | 6.476 | −16.162 | −51.496 | 1.00 | 83.30 S |
| ATOM | 477 | CE | MET | A | 290 | 6.045 | −17.836 | −52.002 | 1.00 | 94.29 C |
| ATOM | 478 | C | MET | A | 290 | 9.975 | −16.937 | −48.398 | 1.00 | 72.53 C |
| ATOM | 479 | O | MET | A | 290 | 9.335 | −16.846 | −47.367 | 1.00 | 82.38 O |
| ATOM | 480 | N | ALA | A | 291 | 11.000 | −17.770 | −48.543 | 1.00 | 64.19 N |
| ATOM | 481 | CA | ALA | A | 291 | 11.496 | −18.617 | −47.475 | 1.00 | 58.96 C |
| ATOM | 482 | CB | ALA | A | 291 | 12.705 | −19.420 | −47.959 | 1.00 | 57.05 C |
| ATOM | 483 | C | ALA | A | 291 | 11.861 | −17.764 | −46.272 | 1.00 | 61.23 C |
| ATOM | 484 | O | ALA | A | 291 | 11.101 | −17.672 | −45.301 | 1.00 | 62.79 O |
| ATOM | 485 | N | THR | A | 292 | 13.059 | −17.192 | −46.327 | 1.00 | 65.17 N |
| ATOM | 486 | CA | THR | A | 292 | 13.448 | −15.999 | −45.568 | 1.00 | 64.26 C |
| ATOM | 487 | CB | THR | A | 292 | 14.110 | −15.007 | −46.532 | 1.00 | 69.50 C |
| ATOM | 488 | OG1 | THR | A | 292 | 15.323 | −15.587 | −47.059 | 1.00 | 71.55 O |
| ATOM | 489 | CG2 | THE | A | 292 | 14.347 | −13.671 | −45.844 | 1.00 | 62.95 C |
| ATOM | 490 | C | THR | A | 292 | 12.298 | −15.218 | −44.986 | 1.00 | 58.22 C |
| ATOM | 491 | O | THR | A | 292 | 12.337 | −14.791 | −43.850 | 1.00 | 64.54 O |
| ATOM | 492 | N | ASN | A | 293 | 11.265 | −15.020 | −45.784 | 1.00 | 59.03 N |
| ATOM | 493 | CA | ASN | A | 293 | 10.222 | −14.127 | −45.389 | 1.00 | 61.00 C |
| ATOM | 494 | CB | ASN | A | 293 | 9.642 | −13.395 | −46.603 | 1.00 | 71.01 C |
| ATOM | 495 | CG | ASN | A | 293 | 8.787 | −12.202 | −46.208 | 1.00 | 71.83 C |
| ATOM | 496 | OD1 | ASN | A | 293 | 9.194 | −11.355 | −45.384 | 1.00 | 61.50 O |
| ATOM | 497 | ND2 | ASN | A | 293 | 7.578 | −12.139 | −46.780 | 1.00 | 77.71 N |
| ATOM | 498 | C | ASN | A | 293 | 9.173 | −14.883 | −44.683 | 1.00 | 58.68 C |
| ATOM | 499 | O | ASN | A | 293 | 8.038 | −14.429 | −44.595 | 1.00 | 70.28 O |
| ATOM | 500 | N | HIS | A | 294 | 9.556 | −16.059 | −44.197 | 1.00 | 64.32 N |
| ATOM | 501 | CA | HIS | A | 294 | 8.653 | −17.004 | −43.542 | 1.00 | 55.39 C |
| ATOM | 502 | CB | HIS | A | 294 | 8.692 | −18.308 | −44.289 | 1.00 | 53.93 C |
| ATOM | 503 | CG | HIS | A | 294 | 8.443 | −19.526 | −43.437 | 1.00 | 56.62 C |
| ATOM | 504 | ND1 | HIS | A | 294 | 7.207 | −19.896 | −43.015 | 1.00 | 48.22 N |
| ATOM | 505 | CE1 | HIS | A | 294 | 7.317 | −21.012 | −42.306 | 1.00 | 44.18 C |
| ATOM | 506 | NE2 | HIS | A | 294 | 8.602 | −21.380 | −42.292 | 1.00 | 45.06 N |
| ATOM | 507 | CD2 | HIS | A | 294 | 9.316 | −20.498 | −42.989 | 1.00 | 51.36 C |
| ATOM | 508 | C | HIS | A | 294 | 9.087 | −17.160 | −42.137 | 1.00 | 55.50 C |
| ATOM | 509 | O | HIS | A | 294 | 8.249 | −17.221 | −41.223 | 1.00 | 51.52 O |
| ATOM | 510 | N | VAL | A | 295 | 10.416 | −17.199 | −41.973 | 1.00 | 56.73 N |
| ATOM | 511 | CA | VAL | A | 295 | 11.112 | −17.067 | −40.683 | 1.00 | 53.77 C |
| ATOM | 512 | CB | VAL | A | 295 | 12.630 | −17.160 | −40.875 | 1.00 | 48.81 C |
| ATOM | 513 | CG1 | VAL | A | 295 | 13.364 | −16.725 | −39.627 | 1.00 | 53.50 C |
| ATOM | 514 | CG2 | VAL | A | 295 | 13.019 | −18.574 | −41.232 | 1.00 | 45.35 C |
| ATOM | 515 | C | VAL | A | 295 | 10.752 | −15.791 | −39.895 | 1.00 | 58.82 C |
| ATOM | 516 | O | VAL | A | 295 | 10.439 | −15.864 | −38.701 | 1.00 | 61.37 O |
| ATOM | 517 | N | GLN | A | 296 | 10.763 | −14.625 | −40.529 | 1.00 | 61.41 N |
| ATOM | 518 | CA | GLN | A | 296 | 10.319 | −13.436 | −39.769 | 1.00 | 74.30 C |
| ATOM | 519 | CB | GLN | A | 296 | 10.510 | −12.121 | −40.562 | 1.00 | 86.54 C |
| ATOM | 520 | CG | GLN | A | 296 | 11.920 | −11.517 | −40.469 | 1.00 | 102.26 C |
| ATOM | 521 | CD | GLN | A | 296 | 13.045 | −12.465 | −40.929 | 1.00 | 112.04 C |
| ATOM | 522 | OE1 | GLN | A | 296 | 12.848 | −13.287 | −41.829 | 1.00 | 116.70 O |
| ATOM | 523 | NE2 | GLN | A | 296 | 14.230 | −12.352 | −40.303 | 1.00 | 95.06 N |
| ATOM | 524 | C | GLN | A | 296 | 8.877 | −13.596 | −39.240 | 1.00 | 69.72 C |
| ATOM | 525 | O | GLN | A | 296 | 8.551 | −13.145 | −38.140 | 1.00 | 60.95 O |
| ATOM | 526 | N | VAL | A | 297 | 8.028 | −14.262 | −40.029 | 1.00 | 73.16 N |
| ATOM | 527 | CA | VAL | A | 297 | 6.624 | −14.475 | −39.649 | 1.00 | 66.44 C |
| ATOM | 528 | CB | VAL | A | 297 | 5.763 | −14.949 | −40.817 | 1.00 | 60.71 C |
| ATOM | 529 | CG1 | VAL | A | 297 | 4.329 | −15.126 | −40.357 | 1.00 | 58.39 C |
| ATOM | 530 | CG2 | VA1 | A | 297 | 5.819 | −13.961 | −41.956 | 1.00 | 65.33 C |
| ATOM | 531 | C | VAL | A | 297 | 6.513 | −15.526 | −38.572 | 1.00 | 61.83 C |
| ATOM | 532 | O | VAL | A | 297 | 5.738 | −15.384 | −37.619 | 1.00 | 57.20 O |
| ATOM | 533 | N | LEU | A | 298 | 7.290 | −16.589 | −38.740 | 1.00 | 61.66 N |
| ATOM | 534 | CA | LEU | A | 298 | 7.267 | −17.664 | −37.781 | 1.00 | 57.85 C |
| ATOM | 535 | CB | LEU | A | 298 | 8.180 | −18.814 | −38.198 | 1.00 | 49.61 C |
| ATOM | 536 | CG | LEU | A | 298 | 8.151 | −19.949 | −37.167 | 1.00 | 48.36 C |
| ATOM | 537 | CD1 | LEU | A | 298 | 6.720 | −20.452 | −36.968 | 1.00 | 47.54 C |
| ATOM | 538 | CD2 | LEU | A | 298 | 9.118 | −21.084 | −37.531 | 1.00 | 47.32 C |
| ATOM | 539 | C | LEU | A | 298 | 7.632 | −17.104 | −36.414 | 1.00 | 55.51 C |
| ATOM | 540 | O | LEU | A | 298 | 6.858 | −17.269 | −35.462 | 1.00 | 54.73 O |
| ATOM | 541 | N | VAL | A | 299 | 8.772 | −16.407 | −36.353 | 1.00 | 53.02 N |
| ATOM | 542 | CA | VAL | A | 299 | 9.273 | −15.813 | −35.110 | 1.00 | 57.28 C |
| ATOM | 543 | CB | VAL | A | 299 | 10.656 | −15.151 | −35.252 | 1.00 | 57.91 C |
| ATOM | 544 | CG1 | VAL | A | 299 | 11.101 | −14.594 | −33.912 | 1.00 | 52.51 C |
| ATOM | 545 | CG2 | VAL | A | 299 | 11.694 | −16.145 | −35.776 | 1.00 | 59.83 C |
| ATOM | 546 | C | VAL | A | 299 | 8.321 | −14.804 | −34.485 | 1.00 | 58.79 C |
| ATOM | 547 | O | VAL | A | 299 | 8.205 | −14.783 | −33.279 | 1.00 | 65.64 O |
| ATOM | 548 | N | GLU | A | 300 | 7.643 | −13.989 | −35.293 | 1.00 | 60.03 N |
| ATOM | 549 | CA | GLU | A | 300 | 6.649 | −13.042 | −34.798 | 1.00 | 60.63 C |
| ATOM | 550 | CB | GLU | A | 300 | 6.157 | −12.104 | −35.927 | 1.00 | 80.96 C |
| ATOM | 551 | CG | GLU | A | 300 | 4.777 | −11.416 | −35.735 | 1.00 | 88.19 C |

APPENDIX 1-continued

| | | | | | | | | | | |
|---|---|---|---|---|---|---|---|---|---|---|
| ATOM | 552 | CD | GLU | A | 300 | 3.581 | −12.193 | −36.339 | 1.00 | 95.22 C |
| ATOM | 553 | OE1 | GLU | A | 300 | 3.762 | −12.923 | −37.345 | 1.00 | 94.41 O |
| ATOM | 554 | OE2 | GLU | A | 300 | 2.442 | −12.078 | −35.815 | 1.00 | 96.81 O |
| ATOM | 555 | C | GLU | A | 300 | 5.483 | −13.770 | −34.177 | 1.00 | 59.89 C |
| ATOM | 556 | O | GLU | A | 300 | 4.957 | −13.343 | −33.140 | 1.00 | 66.98 O |
| ATOM | 557 | N | PHE | A | 301 | 5.054 | −14.848 | −34.833 | 1.00 | 61.04 N |
| ATOM | 558 | CA | PHE | A | 301 | 3.930 | −15.673 | −34.360 | 1.00 | 56.15 C |
| ATOM | 559 | CB | PHE | A | 301 | 3.575 | −16.727 | −35.407 | 1.00 | 47.18 C |
| ATOM | 560 | CG | PHE | A | 301 | 2.497 | −17.671 | −34.977 | 1.00 | 44.94 C |
| ATOM | 561 | CD1 | PHE | A | 301 | 1.215 | −17.218 | −34.730 | 1.00 | 47.68 C |
| ATOM | 562 | CE1 | PHE | A | 301 | 0.226 | −18.089 | −34.325 | 1.00 | 45.74 C |
| ATOM | 563 | CZ | PHE | A | 301 | 0.525 | −19.426 | −34.173 | 1.00 | 48.04 C |
| ATOM | 564 | CE2 | PHE | A | 301 | 1.789 | −19.892 | −34.433 | 1.00 | 42.87 C |
| ATOM | 565 | CD2 | PHE | A | 301 | 2.765 | −19.015 | −34.824 | 1.00 | 45.13 C |
| ATOM | 566 | C | PHE | A | 301 | 4.293 | −16.338 | −33.034 | 1.00 | 61.65 C |
| ATOM | 567 | O | PHE | A | 301 | 3.469 | −16.442 | −32.114 | 1.00 | 62.89 O |
| ATOM | 568 | N | THR | A | 302 | 5.548 | −16.755 | −32.942 | 1.00 | 61.58 N |
| ATOM | 569 | CA | THR | A | 302 | 6.015 | −17.495 | −31.819 | 1.00 | 68.91 C |
| ATOM | 570 | CB | THR | A | 302 | 7.312 | −18.226 | −32.191 | 1.00 | 73.55 C |
| ATOM | 571 | OG1 | THR | A | 302 | 7.101 | −18.931 | −33.421 | 1.00 | 77.09 O |
| ATOM | 572 | CG2 | THR | A | 302 | 7.701 | −19.228 | −31.124 | 1.00 | 69.21 C |
| ATOM | 573 | C | THR | A | 302 | 6.125 | −16.629 | −30.558 | 1.00 | 74.14 C |
| ATOM | 574 | O | THR | A | 302 | 5.550 | −16.971 | −29.532 | 1.00 | 79.79 O |
| ATOM | 575 | N | LYS | A | 303 | 6.827 | −15.503 | −30.642 | 1.00 | 74.35 N |
| ATOM | 576 | CA | LYS | A | 303 | 6.922 | −14.540 | −29.525 | 1.00 | 74.29 C |
| ATOM | 577 | CB | LYS | A | 303 | 7.520 | −13.217 | −29.998 | 1.00 | 75.35 C |
| ATOM | 578 | CG | LYS | A | 303 | 9.027 | −13.125 | −29.874 | 1.00 | 79.85 C |
| ATOM | 579 | CD | LYS | A | 303 | 9.519 | −11.856 | −30.533 | 1.00 | 91.13 C |
| ATOM | 580 | CE | LYS | A | 303 | 10.364 | −11.039 | −29.575 | 1.00 | 104.04 C |
| ATOM | 581 | NZ | LYS | A | 303 | 10.659 | −9.712 | −30.190 | 1.00 | 124.50 N |
| ATOM | 582 | C | LYS | A | 303 | 5.593 | −14.235 | −28.844 | 1.00 | 72.45 C |
| ATOM | 583 | O | LYS | A | 303 | 5.542 | −14.097 | −27.619 | 1.00 | 75.10 O |
| ATOM | 584 | N | LYS | A | 304 | 4.533 | −14.114 | −29.642 | 1.00 | 63.63 N |
| ATOM | 585 | CA | LYS | A | 304 | 3.200 | −13.852 | −29.113 | 1.00 | 61.93 C |
| ATOM | 586 | CB | LYS | A | 304 | 2.375 | −13.023 | −30.115 | 1.00 | 49.28 C |
| ATOM | 587 | C | LYS | A | 304 | 2.440 | −15.130 | −28.651 | 1.00 | 66.56 C |
| ATOM | 588 | O | LYS | A | 304 | 1.241 | −15.067 | −28.373 | 1.00 | 71.71 O |
| ATOM | 589 | N | LEU | A | 305 | 3.119 | −16.277 | −28.569 | 1.00 | 61.25 N |
| ATOM | 590 | CA | LEU | A | 305 | 2.480 | −17.479 | −28.033 | 1.00 | 60.69 C |
| ATOM | 591 | CB | LEU | A | 305 | 3.126 | −18.784 | −28.550 | 1.00 | 65.44 C |
| ATOM | 592 | CG | LEU | A | 305 | 2.806 | −19.404 | −29.943 | 1.00 | 62.71 C |
| ATOM | 593 | CD1 | LEU | A | 305 | 2.513 | −20.888 | −29.814 | 1.00 | 59.26 C |
| ATOM | 594 | CD2 | LEU | A | 305 | 1.620 | −18.739 | −30.627 | 1.00 | 61.96 C |
| ATOM | 595 | C | LEU | A | 305 | 2.512 | −17.433 | −26.517 | 1.00 | 60.98 C |
| ATOM | 596 | O | LEU | A | 305 | 3.576 | −17.233 | −25.922 | 1.00 | 64.73 O |
| ATOM | 597 | N | PRO | A | 306 | 1.339 | −17.605 | −25.880 | 1.00 | 60.84 N |
| ATOM | 598 | CA | PRO | A | 306 | 1.170 | −17.555 | −24.428 | 1.00 | 54.57 C |
| ATOM | 599 | CB | PRO | A | 306 | −0.160 | −18.253 | −24.215 | 1.00 | 53.41 C |
| ATOM | 600 | CG | PRO | A | 306 | −0.951 | −17.928 | −25.451 | 1.00 | 58.61 C |
| ATOM | 601 | CD | PRO | A | 306 | 0.041 | −17.727 | −26.575 | 1.00 | 62.98 C |
| ATOM | 602 | C | PRO | A | 306 | 2.215 | −18.349 | −23.738 | 1.00 | 61.37 C |
| ATOM | 603 | O | PRO | A | 306 | 2.059 | −19.566 | −23.641 | 1.00 | 73.69 O |
| ATOM | 604 | N | GLY | A | 307 | 3.283 | −17.679 | −23.294 | 1.00 | 64.42 N |
| ATOM | 605 | CA | GLY | A | 307 | 4.299 | −18.275 | −22.410 | 1.00 | 61.23 C |
| ATOM | 606 | C | GLY | A | 307 | 5.670 | −18.332 | −23.030 | 1.00 | 65.02 C |
| ATOM | 607 | O | GLY | A | 307 | 6.655 | −18.705 | −22.361 | 1.00 | 58.20 O |
| ATOM | 608 | N | PHE | A | 308 | 5.749 | −17.955 | −24.309 | 1.00 | 65.58 N |
| ATOM | 609 | CA | PHE | A | 308 | 6.999 | −18.148 | −25.039 | 1.00 | 68.30 C |
| ATOM | 610 | CB | PHE | A | 308 | 6.923 | −17.822 | −26.523 | 1.00 | 67.39 C |
| ATOM | 611 | CG | PHE | A | 308 | 8.024 | −18.481 | −27.318 | 1.00 | 65.20 C |
| ATOM | 612 | CD1 | PHE | A | 308 | 7.941 | −19.835 | −27.658 | 1.00 | 60.02 C |
| ATOM | 613 | CE1 | PHE | A | 308 | 8.948 | −20.452 | −28.361 | 1.00 | 57.45 C |
| ATOM | 614 | CZ | PHE | A | 308 | 10.073 | −19.735 | −28.732 | 1.00 | 65.44 C |
| ATOM | 615 | CE2 | PHE | A | 308 | 10.180 | −18.399 | −28.381 | 1.00 | 69.70 C |
| ATOM | 616 | CD2 | PHE | A | 308 | 9.158 | −17.781 | −27.668 | 1.00 | 64.72 C |
| ATOM | 617 | C | PHE | A | 308 | 8.188 | −17.423 | −24.483 | 1.00 | 70.98 C |
| ATOM | 618 | O | PHE | A | 308 | 9.241 | −18.028 | −24.327 | 1.00 | 78.86 O |
| ATOM | 619 | N | GLN | A | 309 | 8.029 | −16.128 | −24.229 | 1.00 | 75.46 N |
| ATOM | 620 | CA | GLN | A | 309 | 9.131 | −15.292 | −23.760 | 1.00 | 73.33 C |
| ATOM | 621 | CB | GLN | A | 309 | 8.718 | −13.822 | −23.738 | 1.00 | 72.57 C |
| ATOM | 622 | CG | GLN | A | 309 | 7.690 | −13.486 | −24.812 | 1.00 | 83.43 C |
| ATOM | 623 | CD | GLN | A | 309 | 8.129 | −12.398 | −25.777 | 1.00 | 82.55 C |
| ATOM | 624 | OE1 | GLN | A | 309 | 9.308 | −12.279 | −26.102 | 1.00 | 93.67 O |
| ATOM | 625 | NE2 | GLN | A | 309 | 7.171 | −11.611 | −26.263 | 1.00 | 79.68 N |
| ATOM | 626 | C | GLN | A | 309 | 9.575 | −15.790 | −22.386 | 1.00 | 76.61 C |
| ATOM | 627 | O | GLN | A | 309 | 10.769 | −15.777 | −22.055 | 1.00 | 74.14 O |
| ATOM | 628 | N | THR | A | 310 | 8.603 | −16.295 | −21.624 | 1.00 | 77.23 N |
| ATOM | 629 | CA | THR | A | 310 | 8.838 | −16.864 | −20.293 | 1.00 | 70.75 C |
| ATOM | 630 | CB | THR | A | 310 | 7.504 | −17.109 | −19.534 | 1.00 | 67.36 C |
| ATOM | 631 | OG1 | THR | A | 310 | 7.128 | −18.487 | −19.608 | 1.00 | 74.51 O |

APPENDIX 1-continued

| ATOM | 632 | CG2 | THR | A | 310 | 6.380 | −16.249 | −20.114 | 1.00 | 67.47 | C |
|---|---|---|---|---|---|---|---|---|---|---|---|
| ATOM | 633 | C | THR | A | 310 | 9.752 | −18.114 | −20.301 | 1.00 | 65.70 | C |
| ATOM | 634 | O | THR | A | 310 | 10.323 | −18.474 | −19.283 | 1.00 | 67.90 | O |
| ATOM | 635 | N | LEU | A | 311 | 9.918 | −18.759 | −21.445 | 1.00 | 66.28 | N |
| ATOM | 636 | CA | LEU | A | 311 | 10.856 | −19.875 | −21.528 | 1.00 | 73.71 | C |
| ATOM | 637 | CB | LEU | A | 311 | 10.674 | −20.648 | −22.830 | 1.00 | 77.09 | C |
| ATOM | 638 | CG | LEU | A | 311 | 9.391 | −21.473 | −22.965 | 1.00 | 85.59 | C |
| ATOM | 639 | CD1 | LEU | A | 311 | 9.540 | −22.322 | −24.221 | 1.00 | 96.45 | C |
| ATOM | 640 | CD2 | LEU | A | 311 | 9.053 | −22.356 | −21.764 | 1.00 | 65.05 | C |
| ATOM | 641 | C | LEU | A | 311 | 12.291 | −19.414 | −21.423 | 1.00 | 75.89 | C |
| ATOM | 642 | O | LEU | A | 311 | 12.551 | −18.215 | −21.379 | 1.00 | 87.18 | O |
| ATOM | 643 | N | ASP | A | 312 | 13.223 | −20.365 | −21.401 | 1.00 | 80.65 | N |
| ATOM | 644 | CA | ASP | A | 312 | 14.653 | −20.054 | −21.361 | 1.00 | 84.19 | C |
| ATOM | 645 | CB | ASP | A | 312 | 15.488 | −21.343 | −21.386 | 1.00 | 91.90 | C |
| ATOM | 646 | CG | ASP | A | 312 | 16.722 | −21.282 | −20.475 | 1.00 | 99.46 | C |
| ATOM | 647 | OD1 | ASP | A | 312 | 16.624 | −20.734 | −19.352 | 1.00 | 111.81 | O |
| ATOM | 648 | OD2 | ASP | A | 312 | 17.787 | −21.809 | −20.873 | 1.00 | 95.02 | O |
| ATOM | 649 | C | ASP | A | 312 | 14.977 | −19.178 | −22.558 | 1.00 | 83.46 | C |
| ATOM | 650 | O | ASP | A | 312 | 14.104 | −18.489 | −23.065 | 1.00 | 82.51 | O |
| ATOM | 651 | N | HIS | A | 313 | 16.224 | −19.194 | −23.011 | 1.00 | 87.88 | N |
| ATOM | 652 | CA | HIS | A | 313 | 16.629 | −18.383 | −24.154 | 1.00 | 86.21 | C |
| ATOM | 653 | CB | HIS | A | 313 | 17.734 | −17.400 | −23.759 | 1.00 | 86.64 | C |
| ATOM | 654 | CG | HIS | A | 313 | 18.578 | −16.924 | −24.924 | 1.00 | 102.61 | C |
| ATOM | 655 | ND1 | HIS | A | 313 | 18.093 | −16.121 | −25.897 | 1.00 | 107.37 | N |
| ATOM | 656 | CE1 | HIS | A | 313 | 19.068 | −15.862 | −26.794 | 1.00 | 108.17 | C |
| ATOM | 657 | NE2 | HIS | A | 313 | 20.183 | −16.508 | −26.398 | 1.00 | 109.77 | N |
| ATOM | 658 | CD2 | HIS | A | 313 | 19.917 | −17.171 | −25.248 | 1.00 | 105.73 | C |
| ATOM | 659 | C | HIS | A | 313 | 17.074 | −19.294 | −25.247 | 1.00 | 81.94 | C |
| ATOM | 660 | O | HIS | A | 313 | 16.713 | −19.131 | −26.410 | 1.00 | 74.47 | O |
| ATOM | 661 | N | GLU | A | 314 | 17.872 | −20.277 | −24.871 | 1.00 | 84.93 | N |
| ATOM | 662 | CA | GLU | A | 314 | 18.319 | −21.277 | −25.818 | 1.00 | 92.99 | C |
| ATOM | 663 | CB | GLU | A | 314 | 19.602 | −21.910 | −25.309 | 1.00 | 97.74 | C |
| ATOM | 664 | CG | GLU | A | 314 | 20.756 | −20.928 | −25.395 | 1.00 | 104.21 | C |
| ATOM | 665 | CD | GLU | A | 314 | 21.936 | −21.345 | −24.559 | 1.00 | 117.42 | C |
| ATOM | 666 | OE1 | GLU | A | 314 | 22.139 | −20.729 | −23.487 | 1.00 | 135.67 | O |
| ATOM | 667 | OE2 | GLU | A | 314 | 22.651 | −22.286 | −24.971 | 1.00 | 115.15 | O |
| ATOM | 668 | C | GLU | A | 314 | 17.218 | −22.302 | −26.116 | 1.00 | 91.59 | C |
| ATOM | 669 | O | GLU | A | 314 | 17.133 | −22.837 | −27.220 | 1.00 | 86.97 | O |
| ATOM | 670 | N | ASP | A | 315 | 16.367 | −22.550 | −25.123 | 1.00 | 91.37 | N |
| ATOM | 671 | CA | ASP | A | 315 | 15.148 | −23.296 | −25.334 | 1.00 | 79.39 | C |
| ATOM | 672 | CB | ASP | A | 315 | 14.327 | −23.372 | −24.042 | 1.00 | 77.31 | C |
| ATOM | 673 | CG | ASP | A | 315 | 14.754 | −24.557 | −23.119 | 1.00 | 86.47 | C |
| ATOM | 674 | OD1 | ASP | A | 315 | 15.774 | −25.241 | −23.406 | 1.00 | 85.05 | O |
| ATOM | 675 | OD2 | ASP | A | 315 | 14.060 | −24.808 | −22.096 | 1.00 | 82.62 | O |
| ATOM | 676 | C | ASP | A | 315 | 14.376 | −22.626 | −26.468 | 1.00 | 80.29 | C |
| ATOM | 677 | O | ASP | A | 315 | 14.005 | −23.277 | −27.451 | 1.00 | 87.76 | O |
| ATOM | 678 | N | GLN | A | 316 | 14.188 | −21.317 | −26.361 | 1.00 | 68.47 | N |
| ATOM | 679 | CA | GLN | A | 316 | 13.529 | −20.570 | −27.415 | 1.00 | 58.86 | C |
| ATOM | 680 | CB | GLN | A | 316 | 13.459 | −19.099 | −27.073 | 1.00 | 57.75 | C |
| ATOM | 681 | CG | GLN | A | 316 | 12.668 | −18.837 | −25.819 | 1.00 | 62.68 | C |
| ATOM | 682 | CD | GLN | A | 316 | 12.523 | −17.374 | −25.543 | 1.00 | 61.67 | C |
| ATOM | 683 | OE1 | GLN | A | 316 | 12.790 | −16.558 | −26.425 | 1.00 | 61.14 | O |
| ATOM | 684 | NE2 | GLN | A | 316 | 12.090 | −17.020 | −24.317 | 1.00 | 58.67 | N |
| ATOM | 685 | C | GLN | A | 316 | 14.217 | −20.747 | −28.746 | 1.00 | 60.12 | C |
| ATOM | 686 | O | GLN | A | 316 | 13.546 | −20.926 | −29.761 | 1.00 | 71.58 | O |
| ATOM | 687 | N | ILE | A | 317 | 15.543 | −20.716 | −28.766 | 1.00 | 52.73 | N |
| ATOM | 688 | CA | ILE | A | 317 | 16.218 | −20.880 | −30.044 | 1.00 | 53.71 | C |
| ATOM | 689 | CB | ILE | A | 317 | 17.712 | −20.537 | −29.986 | 1.00 | 52.18 | C |
| ATOM | 690 | CG1 | ILE | A | 317 | 17.951 | −19.250 | −29.203 | 1.00 | 60.47 | C |
| ATOM | 691 | CD1 | ILE | A | 317 | 17.144 | −18.084 | −29.714 | 1.00 | 73.43 | C |
| ATOM | 692 | CG2 | ILE | A | 317 | 18.264 | −20.361 | −31.374 | 1.00 | 46.56 | C |
| ATOM | 693 | C | ILE | A | 317 | 15.993 | −22.279 | −30.630 | 1.00 | 52.73 | C |
| ATOM | 694 | O | ILE | A | 317 | 15.635 | −22.408 | −31.798 | 1.00 | 49.64 | O |
| ATOM | 695 | N | ALA | A | 318 | 16.166 | −23.302 | −29.796 | 1.00 | 55.99 | N |
| ATOM | 696 | CA | ALA | A | 318 | 16.036 | −24.701 | −30.205 | 1.00 | 58.60 | C |
| ATOM | 697 | CB | ALA | A | 318 | 16.460 | −25.629 | −29.089 | 1.00 | 60.99 | C |
| ATOM | 698 | C | ALA | A | 318 | 14.634 | −25.074 | −30.712 | 1.00 | 60.06 | C |
| ATOM | 699 | O | ALA | A | 318 | 14.515 | −25.807 | −31.716 | 1.00 | 52.87 | O |
| ATOM | 700 | N | LEU | A | 319 | 13.599 | −24.560 | −30.040 | 1.00 | 52.58 | N |
| ATOM | 701 | CA | LEU | A | 319 | 12.224 | −24.658 | −30.548 | 1.00 | 53.33 | C |
| ATOM | 702 | CB | LEU | A | 319 | 11.245 | −23.762 | −29.773 | 1.00 | 46.69 | C |
| ATOM | 703 | CG | LEU | A | 319 | 11.044 | −24.241 | −28.350 | 1.00 | 47.08 | C |
| ATOM | 704 | CD1 | LEU | A | 319 | 10.111 | −23.275 | −27.674 | 1.00 | 55.32 | C |
| ATOM | 705 | CD2 | LEU | A | 319 | 10.469 | −25.653 | −28.288 | 1.00 | 44.56 | C |
| ATOM | 706 | C | LEU | A | 319 | 12.201 | −24.288 | −32.010 | 1.00 | 55.40 | C |
| ATOM | 707 | O | LEU | A | 319 | 12.082 | −25.175 | −32.857 | 1.00 | 53.56 | O |
| ATOM | 708 | N | LEU | A | 320 | 12.351 | −22.982 | −32.275 | 1.00 | 59.00 | N |
| ATOM | 709 | CA | LEU | A | 320 | 12.311 | −22.372 | −33.613 | 1.00 | 55.52 | C |
| ATOM | 710 | CB | LEU | A | 320 | 12.664 | −20.893 | −33.481 | 1.00 | 59.19 | C |
| ATOM | 711 | CG | LEU | A | 320 | 11.676 | −19.713 | −33.524 | 1.00 | 62.42 | C |

APPENDIX 1-continued

| | | | | | | | | | | |
|---|---|---|---|---|---|---|---|---|---|---|
| ATOM | 712 | CD1 | LEU | A | 320 | 10.262 | −20.088 | −33.129 | 1.00 | 61.77 C |
| ATOM | 713 | CD2 | LEU | A | 320 | 12.180 | −18.546 | −32.673 | 1.00 | 62.36 C |
| ATOM | 714 | C | LEU | A | 320 | 13.226 | −23.049 | −34.664 | 1.00 | 56.61 C |
| ATOM | 715 | O | LEU | A | 320 | 12.822 | −23.265 | −35.794 | 1.00 | 52.97 O |
| ATOM | 716 | N | LYS | A | 321 | 14.455 | −23.392 | −34.300 | 1.00 | 59.91 N |
| ATOM | 717 | CA | LYS | A | 321 | 15.317 | −24.133 | −35.214 | 1.00 | 64.97 C |
| ATOM | 718 | CB | LYS | A | 321 | 16.718 | −24.370 | −34.612 | 1.00 | 80.34 C |
| ATOM | 719 | CG | LYS | A | 321 | 17.607 | −25.332 | −35.405 | 1.00 | 75.85 C |
| ATOM | 720 | CD | LYS | A | 321 | 18.992 | −25.466 | −34.790 | 1.00 | 90.17 C |
| ATOM | 721 | CE | LYS | A | 321 | 19.656 | −26.769 | −35.243 | 1.00 | 109.74 C |
| ATOM | 722 | NZ | LYS | A | 321 | 20.940 | −27.111 | −34.545 | 1.00 | 110.75 N |
| ATOM | 723 | C | LYS | A | 321 | 14.662 | −25.455 | −35.556 | 1.00 | 62.81 C |
| ATOM | 724 | O | LYS | A | 321 | 14.874 | −25.968 | −36.645 | 1.00 | 68.21 O |
| ATOM | 725 | N | GLY | A | 322 | 13.869 | −25.991 | −34.621 | 1.00 | 60.22 N |
| ATOM | 726 | CA | GLY | A | 322 | 13.135 | −27.255 | −34.812 | 1.00 | 52.21 C |
| ATOM | 727 | C | GLY | A | 322 | 11.868 | −27.108 | −35.622 | 1.00 | 50.83 C |
| ATOM | 728 | O | GLY | A | 322 | 11.531 | −27.988 | −36.429 | 1.00 | 55.11 O |
| ATOM | 729 | N | SER | A | 323 | 11.187 | −25.977 | −35.451 | 1.00 | 48.32 N |
| ATOM | 730 | CA | SER | A | 323 | 9.925 | −25.725 | −36.150 | 1.00 | 47.38 C |
| ATOM | 731 | CB | SER | A | 323 | 9.050 | −24.764 | −35.375 | 1.00 | 47.62 C |
| ATOM | 732 | OG | SER | A | 323 | 9.558 | −24.504 | −34.092 | 1.00 | 61.38 O |
| ATOM | 733 | C | SER | A | 323 | 10.053 | −25.189 | −37.581 | 1.00 | 49.65 C |
| ATOM | 734 | O | SER | A | 323 | 9.205 | −25.521 | −38.420 | 1.00 | 51.45 O |
| ATOM | 735 | N | ALA | A | 324 | 11.073 | −24.370 | −37.872 | 1.00 | 46.07 N |
| ATOM | 736 | CA | ALA | A | 324 | 11.127 | −23.634 | −39.166 | 1.00 | 46.31 C |
| ATOM | 737 | CB | ALA | A | 324 | 12.506 | −23.010 | −39.405 | 1.00 | 42.02 C |
| ATOM | 738 | C | ALA | A | 324 | 10.677 | −24.441 | −40.405 | 1.00 | 44.46 C |
| ATOM | 739 | O | ALA | A | 324 | 9.881 | −23.995 | −41.227 | 1.00 | 42.56 O |
| ATOM | 740 | N | VAL | A | 325 | 11.205 | −25.636 | −40.556 | 1.00 | 47.80 N |
| ATOM | 741 | CA | VAL | A | 325 | 10.810 | −26.419 | −41.698 | 1.00 | 48.87 C |
| ATOM | 742 | CB | VAL | A | 325 | 11.911 | −27.400 | −42.095 | 1.00 | 47.56 C |
| ATOM | 743 | CG1 | VAL | A | 325 | 11.345 | −28.592 | −42.833 | 1.00 | 61.86 C |
| ATOM | 744 | CG2 | VAL | A | 325 | 12.913 | −26.684 | −42.984 | 1.00 | 50.22 C |
| ATOM | 745 | C | VAL | A | 325 | 9.412 | −27.009 | −41.493 | 1.00 | 50.85 C |
| ATOM | 746 | O | VAL | A | 325 | 8.488 | −26.682 | −42.205 | 1.00 | 53.67 O |
| ATOM | 747 | N | GLU | A | 326 | 9.229 | −27.853 | −40.496 | 1.00 | 56.64 N |
| ATOM | 748 | CA | GLU | A | 326 | 7.878 | −28.339 | −40.237 | 1.00 | 53.58 C |
| ATOM | 749 | CB | GLU | A | 326 | 7.733 | −28.904 | −38.809 | 1.00 | 50.94 C |
| ATOM | 750 | CG | GLU | A | 326 | 8.804 | −29.939 | −38.467 | 1.00 | 55.81 C |
| ATOM | 751 | CD | GLU | A | 326 | 8.540 | −30.778 | −37.207 | 1.00 | 61.68 C |
| ATOM | 752 | OE1 | GLU | A | 326 | 7.453 | −30.657 | −36.600 | 1.00 | 71.26 O |
| ATOM | 753 | OE2 | GLU | A | 326 | 9.425 | −31.583 | −36.821 | 1.00 | 54.78 O |
| ATOM | 754 | C | GLU | A | 326 | 6.850 | −27.243 | −40.558 | 1.00 | 47.09 C |
| ATOM | 755 | O | GLU | A | 326 | 6.023 | −27.425 | −41.446 | 1.00 | 41.35 O |
| ATOM | 756 | N | ALA | A | 327 | 6.938 | −26.098 | −39.885 | 1.00 | 48.19 N |
| ATOM | 757 | CA | ALA | A | 327 | 5.874 | −25.061 | −39.968 | 1.00 | 52.80 C |
| ATOM | 758 | CB | ALA | A | 327 | 6.054 | −24.019 | −38.866 | 1.00 | 51.08 C |
| ATOM | 759 | C | ALA | A | 327 | 5.690 | −24.382 | −41.358 | 1.00 | 48.67 C |
| ATOM | 760 | O | ALA | A | 327 | 4.658 | −23.800 | −41.667 | 1.00 | 49.66 O |
| ATOM | 761 | N | MET | A | 328 | 6.706 | −24.447 | −42.183 | 1.00 | 47.36 N |
| ATOM | 762 | CA | MET | A | 328 | 6.573 | −24.026 | −43.554 | 1.00 | 50.68 C |
| ATOM | 763 | CB | MET | A | 328 | 7.967 | −23.787 | −44.146 | 1.00 | 54.59 C |
| ATOM | 764 | CG | MET | A | 328 | 8.074 | −23.785 | −45.660 | 1.00 | 59.86 C |
| ATOM | 765 | SD | MET | A | 328 | 9.781 | −23.343 | −46.062 | 1.00 | 77.23 S |
| ATOM | 766 | CE | MET | A | 328 | 10.432 | −24.944 | −46.515 | 1.00 | 64.46 C |
| ATOM | 767 | C | MET | A | 328 | 5.780 | −25.064 | −44.344 | 1.00 | 51.40 C |
| ATOM | 768 | O | MET | A | 328 | 4.924 | −24.689 | −45.125 | 1.00 | 55.19 O |
| ATOM | 769 | N | PHE | A | 329 | 6.049 | −26.358 | −44.136 | 1.00 | 54.63 N |
| ATOM | 770 | CA | PHE | A | 329 | 5.265 | −27.446 | −44.770 | 1.00 | 56.60 C |
| ATOM | 771 | CB | PHE | A | 329 | 5.824 | −28.807 | −44.399 | 1.00 | 52.94 C |
| ATOM | 772 | CG | PHE | A | 329 | 6.943 | −29.217 | −45.274 | 1.00 | 59.50 C |
| ATOM | 773 | CD1 | PHE | A | 329 | 6.842 | −30.346 | −46.060 | 1.00 | 59.15 C |
| ATOM | 774 | CE1 | PHE | A | 329 | 7.871 | −30.694 | −46.903 | 1.00 | 71.77 C |
| ATOM | 775 | CZ | PHE | A | 329 | 9.017 | −29.893 | −46.991 | 1.00 | 75.62 C |
| ATOM | 776 | CE2 | PHE | A | 329 | 9.125 | −28.755 | −46.225 | 1.00 | 67.35 C |
| ATOM | 777 | CD2 | PHE | A | 329 | 8.085 | −28.417 | −45.372 | 1.00 | 65.39 C |
| ATOM | 778 | C | PHE | A | 329 | 3.789 | −27.370 | −44.442 | 1.00 | 59.10 C |
| ATOM | 779 | O | PHE | A | 329 | 2.932 | −27.664 | −45.264 | 1.00 | 63.93 O |
| ATOM | 780 | N | LEU | A | 330 | 3.510 | −26.926 | −43.235 | 1.00 | 56.91 N |
| ATOM | 781 | CA | LEU | A | 330 | 2.171 | −26.765 | −42.788 | 1.00 | 56.48 C |
| ATOM | 782 | CB | LEU | A | 330 | 2.227 | −26.638 | −41.276 | 1.00 | 56.95 C |
| ATOM | 783 | CG | LEU | A | 330 | 1.002 | −27.135 | −40.546 | 1.00 | 56.77 C |
| ATOM | 784 | CD1 | LEU | A | 330 | 0.548 | −28.475 | −41.126 | 1.00 | 51.23 C |
| ATOM | 785 | CD2 | LEU | A | 330 | 1.394 | −27.209 | −39.078 | 1.00 | 56.46 C |
| ATOM | 786 | C | LEU | A | 330 | 1.479 | −25.549 | −43.434 | 1.00 | 54.93 C |
| ATOM | 787 | O | LEU | A | 330 | 0.285 | −25.575 | −43.708 | 1.00 | 54.41 O |
| ATOM | 788 | N | ARG | A | 331 | 2.230 | −24.477 | −43.650 | 1.00 | 59.45 N |
| ATOM | 789 | CA | ARG | A | 331 | 1.710 | −23.299 | −44.316 | 1.00 | 59.74 C |
| ATOM | 790 | CB | ARG | A | 331 | 2.755 | −22.198 | −44.350 | 1.00 | 63.71 C |
| ATOM | 791 | CG | ARG | A | 331 | 2.153 | −20.821 | −44.556 | 1.00 | 71.31 C |

APPENDIX 1-continued

| | | | | | | | | | | |
|---|---|---|---|---|---|---|---|---|---|---|
| ATOM | 792 | CD | ARG | A | 331 | 2.078 | −20.077 | −43.229 | 1.00 | 71.87 C |
| ATOM | 793 | NE | ARG | A | 331 | 0.747 | −19.532 | −43.008 | 1.00 | 68.91 N |
| ATOM | 794 | CZ | ARG | A | 331 | 0.394 | −18.779 | −41.964 | 1.00 | 73.36 C |
| ATOM | 795 | NH1 | ARG | A | 331 | 1.278 | −18.465 | −41.022 | 1.00 | 67.47 N |
| ATOM | 796 | NH2 | ARG | A | 331 | −0.862 | −18.330 | −41.865 | 1.00 | 76.61 N |
| ATOM | 797 | C | ARG | A | 331 | 1.368 | −23.671 | −45.746 | 1.00 | 62.02 C |
| ATOM | 798 | O | ARG | A | 331 | 0.323 | −23.262 | −46.288 | 1.00 | 64.71 O |
| ATOM | 799 | N | SER | A | 332 | 2.254 | −24.444 | −46.361 | 1.00 | 53.41 N |
| ATOM | 800 | CA | SER | A | 332 | 2.112 | −24.713 | −47.764 | 1.00 | 59.33 C |
| ATOM | 801 | CB | SER | A | 332 | 3.216 | −25.630 | −48.250 | 1.00 | 65.17 C |
| ATOM | 802 | OG | SER | A | 332 | 4.452 | −25.278 | −47.679 | 1.00 | 69.68 O |
| ATOM | 803 | C | SER | A | 332 | 0.814 | −25.429 | −47.901 | 1.00 | 57.30 C |
| ATOM | 804 | O | SER | A | 332 | −0.005 | −25.111 | −48.747 | 1.00 | 54.74 O |
| ATOM | 805 | N | ALA | A | 333 | 0.638 | −26.399 | −47.020 | 1.00 | 63.13 N |
| ATOM | 806 | CA | ALA | A | 333 | −0.484 | −27.297 | −47.075 | 1.00 | 61.51 C |
| ATOM | 807 | CB | ALA | A | 333 | −0.357 | −28.335 | −45.969 | 1.00 | 62.00 C |
| ATOM | 808 | C | ALA | A | 333 | −1.806 | −26.514 | −47.002 | 1.00 | 60.01 C |
| ATOM | 809 | O | ALA | A | 333 | −2.690 | −26.756 | −47.802 | 1.00 | 60.51 O |
| ATOM | 810 | N | GLU | A | 334 | −1.921 | −25.562 | −46.075 | 1.00 | 62.61 N |
| ATOM | 811 | CA | GLU | A | 334 | −3.060 | −24.633 | −46.045 | 1.00 | 66.75 C |
| ATOM | 812 | CB | GLU | A | 334 | −2.861 | −23.574 | −44.949 | 1.00 | 66.73 C |
| ATOM | 813 | CG | GLU | A | 334 | −3.982 | −22.541 | −44.830 | 1.00 | 73.35 C |
| ATOM | 814 | CD | GLU | A | 334 | −3.878 | −21.695 | −43.567 | 1.00 | 84.01 C |
| ATOM | 815 | OE1 | GLU | A | 334 | −2.802 | −21.681 | −42.930 | 1.00 | 94.13 O |
| ATOM | 816 | OE2 | GLU | A | 334 | −4.866 | −21.036 | −43.194 | 1.00 | 82.24 O |
| ATOM | 817 | C | GLU | A | 334 | −3.274 | −23.968 | −47.430 | 1.00 | 69.28 C |
| ATOM | 818 | O | GLU | A | 334 | −4.357 | −24.081 | −48.021 | 1.00 | 59.62 O |
| ATOM | 819 | N | ILE | A | 335 | −2.248 | −23.293 | −47.952 | 1.00 | 62.70 N |
| ATOM | 820 | CA | ILE | A | 335 | −2.352 | −22.729 | −49.292 | 1.00 | 67.98 C |
| ATOM | 821 | CB | ILE | A | 335 | −1.025 | −22.056 | −49.744 | 1.00 | 74.77 C |
| ATOM | 822 | CG1 | ILE | A | 335 | −0.700 | −20.870 | −48.829 | 1.00 | 67.09 C |
| ATOM | 823 | CD1 | ILE | A | 335 | −1.919 | −20.039 | −48.504 | 1.00 | 58.03 C |
| ATOM | 824 | CG2 | ILE | A | 335 | −1.070 | −21.638 | −51.220 | 1.00 | 68.45 C |
| ATOM | 825 | C | ILE | A | 335 | −2.875 | −23.773 | −50.296 | 1.00 | 68.48 C |
| ATOM | 826 | O | ILE | A | 335 | −4.069 | −23.746 | −50.616 | 1.00 | 70.77 O |
| ATOM | 827 | N | PHE | A | 336 | −1.996 | −24.685 | −50.742 | 1.00 | 66.07 N |
| ATOM | 828 | CA | PHE | A | 336 | −2.296 | −25.856 | −51.636 | 1.00 | 70.37 C |
| ATOM | 829 | CB | PHE | A | 336 | −1.266 | −26.971 | −51.364 | 1.00 | 73.56 C |
| ATOM | 830 | CG | PHE | A | 336 | −1.267 | −28.133 | −52.347 | 1.00 | 83.32 C |
| ATOM | 831 | CD1 | PHE | A | 336 | −0.289 | −28.228 | −53.331 | 1.00 | 85.23 C |
| ATOM | 832 | CE1 | PHE | A | 336 | −0.260 | −29.325 | −54.202 | 1.00 | 86.89 C |
| ATOM | 833 | CZ | PHE | A | 336 | −1.188 | −30.358 | −54.075 | 1.00 | 85.97 C |
| ATOM | 834 | CE2 | PHE | A | 336 | −2.152 | −30.306 | −53.079 | 1.00 | 78.88 C |
| ATOM | 835 | CD2 | PHE | A | 336 | −2.177 | −29.210 | −52.212 | 1.00 | 93.50 C |
| ATOM | 836 | C | PHE | A | 336 | −3.742 | −26.403 | −51.661 | 1.00 | 73.69 C |
| ATOM | 837 | O | PHE | A | 336 | −4.162 | −26.922 | −52.692 | 1.00 | 82.48 O |
| ATOM | 838 | N | ASN | A | 337 | −4.498 | −26.286 | −50.567 | 1.00 | 72.78 N |
| ATOM | 839 | CA | ASN | A | 337 | −5.924 | −26.658 | −50.580 | 1.00 | 82.91 C |
| ATOM | 840 | CD | ASN | A | 337 | −6.135 | −28.099 | −50.089 | 1.00 | 85.87 C |
| ATOM | 841 | CG | ASN | A | 337 | −5.188 | −28.485 | −48.978 | 1.00 | 80.60 C |
| ATOM | 842 | OD1 | ASN | A | 337 | −4.661 | −29.593 | −48.960 | 1.00 | 85.60 O |
| ATOM | 843 | ND2 | ASN | A | 337 | −4.984 | −27.587 | −48.033 | 1.00 | 96.17 N |
| ATOM | 844 | C | ASN | A | 337 | −6.970 | −25.731 | −49.920 | 1.00 | 89.01 C |
| ATOM | 845 | O | ASN | A | 337 | −8.174 | −25.922 | −50.127 | 1.00 | 90.54 O |
| ATOM | 846 | N | LYS | A | 338 | −6.534 | −24.759 | −49.119 | 1.00 | 93.60 N |
| ATOM | 847 | CA | LYS | A | 338 | −7.475 | −23.778 | −48.562 | 1.00 | 91.06 C |
| ATOM | 848 | CB | LYS | A | 338 | −7.135 | −23.375 | −47.120 | 1.00 | 80.07 C |
| ATOM | 849 | C | LYS | A | 338 | −7.520 | −22.574 | −49.489 | 1.00 | 92.41 C |
| ATOM | 850 | O | LYS | A | 338 | −8.576 | −22.277 | −50.045 | 1.00 | 92.60 O |
| ATOM | 851 | N | LYS | A | 339 | −6.381 | −21.897 | −49.664 | 1.00 | 91.02 N |
| ATOM | 852 | CA | LYS | A | 339 | −6.241 | −20.891 | −50.713 | 1.00 | 100.48 C |
| ATOM | 853 | CB | LYS | A | 339 | −4.898 | −20.168 | −50.571 | 1.00 | 109.14 C |
| ATOM | 854 | CG | LYS | A | 339 | −4.796 | −18.797 | −51.247 | 1.00 | 120.94 C |
| ATOM | 855 | CD | LYS | A | 339 | −3.999 | −18.876 | −52.552 | 1.00 | 133.47 C |
| ATOM | 856 | CE | LYS | A | 339 | −3.153 | −17.622 | −52.813 | 1.00 | 139.65 C |
| ATOM | 857 | NZ | LYS | A | 339 | −2.052 | −17.804 | −53.819 | 1.00 | 126.30 N |
| ATOM | 858 | C | LYS | A | 339 | −6.370 | −21.650 | −52.047 | 1.00 | 96.18 C |
| ATOM | 859 | O | LYS | A | 339 | −6.694 | −22.843 | −52.026 | 1.00 | 96.13 O |
| ATOM | 860 | N | LEU | A | 340 | −6.155 | −20.980 | −53.183 | 1.00 | 83.77 N |
| ATOM | 861 | CA | LEU | A | 340 | −6.213 | −21.630 | −54.504 | 1.00 | 99.84 C |
| ATOM | 862 | CB | LEU | A | 340 | −5.086 | −22.673 | −54.630 | 1.00 | 95.45 C |
| ATOM | 863 | CG | LEU | A | 340 | −5.251 | −24.063 | −55.263 | 1.00 | 86.80 C |
| ATOM | 864 | CD1 | LEU | A | 340 | −3.878 | −24.682 | −55.445 | 1.00 | 74.75 C |
| ATOM | 865 | CD2 | LEU | A | 340 | −6.138 | −24.984 | −54.431 | 1.00 | 91.28 C |
| ATOM | 866 | C | LEU | A | 340 | −7.604 | −22.219 | −54.880 | 1.00 | 122.11 C |
| ATOM | 867 | O | LEU | A | 340 | −8.332 | −22.714 | −54.000 | 1.00 | 124.19 O |
| ATOM | 868 | N | PRO | A | 341 | −7.972 | −22.165 | −56.189 | 1.00 | 129.21 N |
| ATOM | 869 | CA | PRO | A | 341 | −9.256 | −22.681 | −56.699 | 1.00 | 123.39 C |
| ATOM | 870 | CB | PRO | A | 341 | −9.156 | −22.440 | −58.209 | 1.00 | 116.59 C |
| ATOM | 871 | CG | PRO | A | 341 | −8.243 | −21.277 | −58.334 | 1.00 | 120.32 C |

APPENDIX 1-continued

| | | | | | | | | | | |
|---|---|---|---|---|---|---|---|---|---|---|
| ATOM | 872 | CD | PRO | A | 341 | −7.223 | −21.459 | −57.249 | 1.00 | 122.04 C |
| ATOM | 873 | C | PRO | A | 341 | −9.490 | −24.164 | −56.402 | 1.00 | 126.17 C |
| ATOM | 874 | O | PRO | A | 341 | −9.887 | −24.505 | −55.285 | 1.00 | 119.75 O |
| ATOM | 875 | N | SER | A | 342 | −9.249 | −25.027 | −57.392 | 1.00 | 139.18 N |
| ATOM | 876 | CA | SER | A | 342 | −9.495 | −26.468 | −57.249 | 1.00 | 144.09 C |
| ATOM | 877 | CB | SER | A | 342 | −10.695 | −26.899 | −58.106 | 1.00 | 136.31 C |
| ATOM | 878 | OG | SER | A | 342 | −11.188 | −28.169 | −57.695 | 1.00 | 136.81 O |
| ATOM | 879 | C | SER | A | 342 | −8.264 | −27.361 | −57.523 | 1.00 | 144.85 C |
| ATOM | 880 | O | SER | A | 342 | −8.282 | −28.198 | −58.433 | 1.00 | 145.23 O |
| ATOM | 881 | N | GLY | A | 343 | −7.201 | −27.148 | −56.738 | 1.00 | 145.23 N |
| ATOM | 882 | CA | GLY | A | 343 | −6.060 | −28.077 | −56.605 | 1.00 | 138.81 C |
| ATOM | 883 | C | GLY | A | 343 | −5.120 | −28.315 | −57.778 | 1.00 | 142.49 C |
| ATOM | 884 | O | GLY | A | 343 | −4.456 | −27.391 | −58.258 | 1.00 | 142.71 O |
| ATOM | 885 | N | HIS | A | 344 | −5.075 | −29.575 | −58.216 | 1.00 | 143.40 N |
| ATOM | 886 | CA | HIS | A | 344 | −4.155 | −30.083 | −59.250 | 1.00 | 141.02 C |
| ATOM | 887 | CB | HIS | A | 344 | −4.699 | −31.379 | −59.866 | 1.00 | 133.69 C |
| ATOM | 888 | CG | HIS | A | 344 | −6.106 | −31.262 | −60.411 | 1.00 | 131.68 C |
| ATOM | 889 | ND1 | HIS | A | 344 | −6.364 | −31.153 | −61.729 | 1.00 | 130.33 N |
| ATOM | 890 | CE1 | HIS | A | 344 | −7.696 | −31.074 | −61.922 | 1.00 | 130.19 C |
| ATOM | 891 | NE2 | HIS | A | 344 | −8.295 | −31.134 | −60.721 | 1.00 | 137.10 N |
| ATOM | 892 | CD2 | HIS | A | 344 | −7.343 | −31.253 | −59.765 | 1.00 | 130.93 C |
| ATOM | 893 | C | HIS | A | 344 | −3.704 | −29.108 | −60.326 | 1.00 | 145.45 C |
| ATOM | 894 | O | HIS | A | 344 | −4.452 | −28.807 | −61.255 | 1.00 | 157.91 O |
| ATOM | 895 | N | SER | A | 345 | −2.472 | −28.604 | −60.221 | 1.00 | 134.15 N |
| ATOM | 896 | CA | SER | A | 345 | −1.552 | −28.895 | −59.112 | 1.00 | 137.25 C |
| ATOM | 897 | CB | SER | A | 345 | −1.286 | −30.411 | −58.957 | 1.00 | 141.52 C |
| ATOM | 898 | OG | SER | A | 345 | −0.741 | −30.969 | −60.144 | 1.00 | 144.70 O |
| ATOM | 899 | C | SER | A | 345 | −0.230 | −28.144 | −59.305 | 1.00 | 124.13 C |
| ATOM | 900 | O | SER | A | 345 | 0.857 | −28.719 | −59.142 | 1.00 | 101.11 O |
| ATOM | 901 | N | ASP | A | 346 | −0.328 | −26.864 | −59.663 | 1.00 | 106.09 N |
| ATOM | 902 | CA | ASP | A | 346 | 0.849 | −26.015 | −59.820 | 1.00 | 102.92 C |
| ATOM | 903 | CB | ASP | A | 346 | 1.392 | −25.598 | −58.447 | 1.00 | 97.96 C |
| ATOM | 904 | CG | ASP | A | 346 | 0.323 | −24.950 | −57.567 | 1.00 | 90.88 C |
| ATOM | 905 | OD1 | ASP | A | 346 | −0.730 | −24.581 | −58.112 | 1.00 | 92.13 O |
| ATOM | 906 | OD2 | ASP | A | 346 | 0.520 | −24.814 | −56.337 | 1.00 | 85.92 O |
| ATOM | 907 | C | ASP | A | 346 | 1.910 | −26.697 | −60.698 | 1.00 | 106.08 C |
| ATOM | 908 | O | ASP | A | 346 | 2.592 | −26.040 | −61.505 | 1.00 | 110.93 O |
| ATOM | 909 | N | LEU | A | 347 | 2.032 | −28.015 | −60.520 | 1.00 | 99.50 N |
| ATOM | 910 | CA | LEU | A | 347 | 2.561 | −28.940 | −61.537 | 1.00 | 107.46 C |
| ATOM | 911 | CB | LEU | A | 347 | 1.412 | −29.437 | −62.440 | 1.00 | 101.24 C |
| ATOM | 912 | CG | LEU | A | 347 | 0.243 | −28.482 | −62.750 | 1.00 | 104.48 C |
| ATOM | 913 | CD1 | LEU | A | 347 | 0.549 | −27.515 | −63.893 | 1.00 | 96.33 C |
| ATOM | 914 | CD2 | LEU | A | 347 | −1.032 | −29.267 | −63.021 | 1.00 | 107.17 C |
| ATOM | 915 | C | LEU | A | 347 | 3.713 | −28.396 | −62.379 | 1.00 | 107.53 C |
| ATOM | 916 | O | LEU | A | 347 | 3.880 | −28.773 | −63.542 | 1.00 | 91.70 O |
| ATOM | 917 | N | LEU | A | 348 | 4.502 | −27.513 | −61.772 | 1.00 | 108.64 N |
| ATOM | 918 | CA | LEU | A | 348 | 5.669 | −26.925 | −62.411 | 1.00 | 112.26 C |
| ATOM | 919 | CB | LEU | A | 348 | 6.278 | −25.869 | −61.486 | 1.00 | 110.90 C |
| ATOM | 920 | CG | LEU | A | 348 | 7.049 | −26.305 | −60.216 | 1.00 | 113.90 C |
| ATOM | 921 | CD1 | LEU | A | 348 | 6.334 | −27.364 | −59.361 | 1.00 | 103.95 C |
| ATOM | 922 | CD2 | LEU | A | 348 | 8.485 | −26.728 | −60.534 | 1.00 | 97.57 C |
| ATOM | 923 | C | LEU | A | 348 | 6.742 | −27.964 | −62.762 | 1.00 | 117.26 C |
| ATOM | 924 | O | LEU | A | 348 | 7.511 | −27.749 | −63.685 | 1.00 | 109.91 O |
| ATOM | 925 | N | GLU | A | 349 | 6.763 | −29.080 | −62.025 | 1.00 | 123.79 N |
| ATOM | 926 | CA | GLU | A | 349 | 7.914 | −30.007 | −61.921 | 1.00 | 119.63 C |
| ATOM | 927 | CB | GLU | A | 349 | 7.476 | −31.431 | −61.631 | 1.00 | 110.22 C |
| ATOM | 928 | CG | GLU | A | 349 | 6.190 | −31.552 | −60.859 | 1.00 | 104.40 C |
| ATOM | 929 | CD | GLU | A | 349 | 5.606 | −32.923 | −61.030 | 1.00 | 103.59 C |
| ATOM | 930 | OE1 | GLU | A | 349 | 4.365 | −33.029 | −61.109 | 1.00 | 100.55 O |
| ATOM | 931 | OE2 | GLU | A | 349 | 6.402 | −33.889 | −61.108 | 1.00 | 107.55 O |
| ATOM | 932 | C | GLU | A | 349 | 8.852 | −30.063 | −63.097 | 1.00 | 121.05 C |
| ATOM | 933 | O | GLU | A | 349 | 10.054 | −30.243 | −62.911 | 1.00 | 125.00 O |
| ATOM | 934 | N | GLU | A | 350 | 8.295 | −29.956 | −64.302 | 1.00 | 125.72 N |
| ATOM | 935 | CA | GLU | A | 350 | 9.092 | −29.788 | −65.523 | 1.00 | 130.12 C |
| ATOM | 936 | CB | GLU | A | 350 | 8.204 | −29.858 | −66.776 | 1.00 | 120.02 C |
| ATOM | 937 | CG | GLU | A | 350 | 6.892 | −29.092 | −66.676 | 1.00 | 116.65 C |
| ATOM | 938 | CD | GLU | A | 350 | 5.684 | −29.941 | −67.039 | 1.00 | 124.47 C |
| ATOM | 939 | OE1 | GLU | A | 350 | 5.538 | −31.068 | −66.491 | 1.00 | 122.57 O |
| ATOM | 940 | OE2 | GLU | A | 350 | 4.867 | −29.475 | −67.864 | 1.00 | 118.46 O |
| ATOM | 941 | C | GLU | A | 350 | 9.869 | −28.470 | −65.433 | 1.00 | 136.14 C |
| ATOM | 942 | O | GLU | A | 350 | 10.347 | −27.935 | −66.443 | 1.00 | 135.13 O |
| ATOM | 943 | N | ARG | A | 351 | 9.983 | −27.978 | −64.193 | 1.00 | 139.80 N |
| ATOM | 944 | CA | ARG | A | 351 | 10.716 | −26.767 | −63.848 | 1.00 | 133.48 C |
| ATOM | 945 | CB | ARG | A | 351 | 9.780 | −25.547 | −63.861 | 1.00 | 123.93 C |
| ATOM | 946 | C | ARG | A | 351 | 11.448 | −26.857 | −62.499 | 1.00 | 130.90 C |
| ATOM | 947 | O | ARG | A | 351 | 12.004 | −25.854 | −62.047 | 1.00 | 133.48 O |
| ATOM | 948 | N | ILE | A | 352 | 11.468 | −28.029 | −61.857 | 1.00 | 130.23 N |
| ATOM | 949 | CA | ILE | A | 352 | 12.181 | −28.143 | −60.563 | 1.00 | 140.25 C |
| ATOM | 950 | CB | ILE | A | 352 | 11.679 | −29.296 | −59.637 | 1.00 | 135.27 C |
| ATOM | 951 | CG1 | ILE | A | 352 | 12.534 | −30.579 | −59.735 | 1.00 | 133.63 C |

APPENDIX 1-continued

| | | | | | | | | | | |
|---|---|---|---|---|---|---|---|---|---|---|
| ATOM | 952 | CD1 | ILE | A | 352 | 12.260 | −31.484 | −60.922 | 1.00 | 145.05 C |
| ATOM | 953 | CG2 | ILE | A | 352 | 10.183 | −29.504 | −59.799 | 1.00 | 141.81 C |
| ATOM | 954 | C | ILE | A | 352 | 13.706 | −28.165 | −60.705 | 1.00 | 143.17 C |
| ATOM | 955 | O | ILE | A | 352 | 14.279 | −29.076 | −61.316 | 1.00 | 153.89 O |
| ATOM | 956 | N | ARG | A | 353 | 14.344 | −27.126 | −60.159 | 1.00 | 146.73 N |
| ATOM | 957 | CA | ARG | A | 353 | 15.803 | −27.023 | −60.126 | 1.00 | 150.03 C |
| ATOM | 958 | CB | ARG | A | 353 | 16.253 | −25.598 | −60.514 | 1.00 | 138.30 C |
| ATOM | 959 | CG | ARG | A | 353 | 17.697 | −25.438 | −61.001 | 1.00 | 125.87 C |
| ATOM | 960 | CD | ARG | A | 353 | 18.158 | −26.530 | −61.967 | 1.00 | 131.21 C |
| ATOM | 961 | NE | ARG | A | 353 | 19.071 | −27.495 | −61.337 | 1.00 | 127.85 N |
| ATOM | 962 | CZ | ARG | A | 353 | 19.719 | −28.473 | −61.976 | 1.00 | 122.02 C |
| ATOM | 963 | NH1 | ARG | A | 353 | 19.572 | −28.654 | −63.286 | 1.00 | 126.04 N |
| ATOM | 964 | NH2 | ARG | A | 353 | 20.526 | −29.276 | −61.301 | 1.00 | 110.49 N |
| ATOM | 965 | C | ARG | A | 353 | 16.271 | −27.421 | −58.721 | 1.00 | 152.03 C |
| ATOM | 966 | O | ARG | A | 353 | 15.433 | −27.803 | −57.871 | 1.00 | 154.63 O |
| ATOM | 967 | N | ASN | A | 354 | 17.594 | −27.367 | −58.490 | 1.00 | 152.81 N |
| ATOM | 968 | CA | ASN | A | 354 | 18.153 | −27.602 | −57.161 | 1.00 | 139.59 C |
| ATOM | 969 | CB | ASN | A | 354 | 19.581 | −28.167 | −57.236 | 1.00 | 142.59 C |
| ATOM | 970 | CG | ASN | A | 354 | 19.612 | −29.655 | −57.555 | 1.00 | 143.59 C |
| ATOM | 971 | OD1 | ASN | A | 354 | 18.909 | −30.127 | −58.452 | 1.00 | 135.70 O |
| ATOM | 972 | ND2 | ASN | A | 354 | 20.439 | −30.404 | −56.823 | 1.00 | 139.02 N |
| ATOM | 973 | C | ASN | A | 354 | 18.096 | −26.330 | −56.320 | 1.00 | 136.02 C |
| ATOM | 974 | O | ASN | A | 354 | 17.340 | −25.398 | −56.657 | 1.00 | 111.48 O |
| ATOM | 975 | N | SER | A | 355 | 18.900 | −26.313 | −55.244 | 1.00 | 132.96 N |
| ATOM | 976 | CA | SER | A | 355 | 18.945 | −25.235 | −54.229 | 1.00 | 123.60 C |
| ATOM | 977 | CB | SER | A | 355 | 17.589 | −25.082 | −53.528 | 1.00 | 114.25 C |
| ATOM | 978 | OG | SER | A | 355 | 17.746 | −24.450 | −52.270 | 1.00 | 106.25 O |
| ATOM | 979 | C | SER | A | 355 | 20.066 | −25.312 | −53.154 | 1.00 | 115.95 C |
| ATOM | 980 | O | SER | A | 355 | 20.366 | −24.297 | −52.519 | 1.00 | 110.19 O |
| ATOM | 981 | N | GLY | A | 356 | 20.665 | −26.478 | −52.905 | 1.00 | 113.67 N |
| ATOM | 982 | CA | GLY | A | 356 | 20.295 | −27.747 | −53.503 | 1.00 | 119.68 C |
| ATOM | 983 | C | GLY | A | 356 | 18.968 | −28.241 | −52.968 | 1.00 | 117.39 C |
| ATOM | 984 | O | GLY | A | 356 | 18.816 | −28.467 | −51.765 | 1.00 | 110.81 O |
| ATOM | 985 | N | ILE | A | 357 | 18.008 | −28.358 | −53.882 | 1.00 | 107.57 N |
| ATOM | 986 | CA | ILE | A | 357 | 16.685 | −28.898 | −53.628 | 1.00 | 117.36 C |
| ATOM | 987 | CB | ILE | A | 357 | 15.700 | −27.818 | −53.077 | 1.00 | 111.80 C |
| ATOM | 988 | CG1 | ILE | A | 357 | 15.872 | −27.645 | −51.552 | 1.00 | 107.36 C |
| ATOM | 989 | CD1 | ILE | A | 357 | 15.197 | −26.440 | −50.914 | 1.00 | 82.84 C |
| ATOM | 990 | CG2 | ILE | A | 357 | 14.251 | −28.169 | −53.400 | 1.00 | 112.35 C |
| ATOM | 991 | C | ILE | A | 357 | 16.247 | −29.483 | −54.977 | 1.00 | 129.31 C |
| ATOM | 992 | O | ILE | A | 357 | 16.179 | −28.750 | −55.955 | 1.00 | 35.23 O |
| ATOM | 993 | N | SER | A | 358 | 15.987 | −30.795 | −55.036 | 1.00 | 130.11 N |
| ATOM | 994 | CA | SER | A | 358 | 15.687 | −31.483 | −56.310 | 1.00 | 120.57 C |
| ATOM | 995 | CB | SER | A | 358 | 16.666 | −32.637 | −56.555 | 1.00 | 138.50 C |
| ATOM | 996 | OG | SER | A | 358 | 17.827 | −32.194 | −57.243 | 1.00 | 154.78 O |
| ATOM | 997 | C | SER | A | 358 | 14.232 | −31.932 | −56.520 | 1.00 | 110.13 C |
| ATOM | 998 | O | SER | A | 358 | 13.355 | −31.096 | −56.726 | 1.00 | 109.57 O |
| ATOM | 999 | N | ALA | A | 359 | 13.994 | −33.248 | −56.485 | 1.00 | 109.37 N |
| ATOM | 1000 | CA | ALA | A | 359 | 12.678 | −33.840 | −56.795 | 1.00 | 103.82 C |
| ATOM | 1001 | CB | ALA | A | 359 | 12.747 | −34.686 | −58.058 | 1.00 | 99.74 C |
| ATOM | 1002 | C | ALA | A | 359 | 12.122 | −34.667 | −55.648 | 1.00 | 104.08 C |
| ATOM | 1003 | O | ALA | A | 359 | 10.941 | −35.011 | −55.648 | 1.00 | 104.63 O |
| ATOM | 1004 | N | GLU | A | 360 | 12.981 | −34.992 | −54.682 | 1.00 | 109.76 N |
| ATOM | 1005 | CA | GLU | A | 360 | 12.566 | −35.650 | −53.434 | 1.00 | 108.21 C |
| ATOM | 1006 | CB | GLU | A | 360 | 13.681 | −36.543 | −52.871 | 1.00 | 127.93 C |
| ATOM | 1007 | CG | GLU | A | 360 | 15.040 | −35.869 | −52.732 | 1.00 | 135.98 C |
| ATOM | 1008 | CD | GLU | A | 360 | 15.837 | −35.907 | −54.024 | 1.00 | 152.50 C |
| ATOM | 1009 | OE1 | GLU | A | 360 | 16.214 | −34.812 | −54.518 | 1.00 | 155.98 O |
| ATOM | 1010 | OE2 | GLU | A | 360 | 16.074 | −37.031 | −54.555 | 1.00 | 168.11 O |
| ATOM | 1011 | C | GLU | A | 360 | 12.142 | −34.631 | −52.383 | 1.00 | 97.30 C |
| ATOM | 1012 | O | GLU | A | 360 | 12.044 | −34.947 | −51.204 | 1.00 | 91.08 O |
| ATOM | 1013 | N | TYR | A | 361 | 11.929 | −33.400 | −52.830 | 1.00 | 98.35 N |
| ATOM | 1014 | CA | TYR | A | 361 | 11.324 | −32.345 | −52.037 | 1.00 | 92.99 C |
| ATOM | 1015 | CB | TYR | A | 361 | 12.101 | −31.048 | −52.229 | 1.00 | 91.01 C |
| ATOM | 1016 | CG | TYR | A | 361 | 13.369 | −30.939 | −51.415 | 1.00 | 89.37 C |
| ATOM | 1017 | CD1 | TYR | A | 361 | 14.607 | −31.246 | −51.969 | 1.00 | 88.29 C |
| ATOM | 1018 | CE1 | TYR | A | 361 | 15.783 | −31.140 | −51.230 | 1.00 | 88.98 C |
| ATOM | 1019 | CZ | TYR | A | 361 | 15.726 | −30.710 | −49.916 | 1.00 | 94.54 C |
| ATOM | 1020 | OH | TYR | A | 361 | 16.880 | −30.610 | −49.171 | 1.00 | 93.87 O |
| ATOM | 1021 | CE2 | TYR | A | 361 | 14.505 | −30.388 | −49.345 | 1.00 | 98.67 C |
| ATOM | 1022 | CD2 | TYR | A | 361 | 13.336 | −30.502 | −50.093 | 1.00 | 97.22 C |
| ATOM | 1023 | C | TYR | A | 361 | 9.872 | −32.156 | −52.505 | 1.00 | 103.53 C |
| ATOM | 1024 | O | TYR | A | 361 | 8.973 | −31.804 | −51.706 | 1.00 | 95.81 O |
| ATOM | 1025 | N | ILE | A | 362 | 9.671 | −32.392 | −53.810 | 1.00 | 98.24 N |
| ATOM | 1026 | CA | ILE | A | 362 | 8.372 | −32.305 | −54.487 | 1.00 | 82.37 C |
| ATOM | 1027 | CB | ILE | A | 362 | 8.536 | −32.386 | −56.023 | 1.00 | 85.79 C |
| ATOM | 1028 | CG1 | ILE | A | 362 | 8.789 | −30.997 | −56.632 | 1.00 | 80.82 C |
| ATOM | 1029 | CD1 | ILE | A | 362 | 10.148 | −30.394 | −56.309 | 1.00 | 74.96 C |
| ATOM | 1030 | CG2 | ILE | A | 362 | 7.347 | −33.074 | −56.697 | 1.00 | 83.00 C |
| ATOM | 1031 | C | ILE | A | 362 | 7.421 | −33.389 | −54.011 | 1.00 | 82.56 C |

APPENDIX 1-continued

| | | | | | | | | | | |
|---|---|---|---|---|---|---|---|---|---|---|
| ATOM | 1032 | O | ILE | A | 362 | 6.339 | −33.083 | −53.491 | 1.00 | 80.16 O |
| ATOM | 1033 | N | THR | A | 363 | 7.841 | −34.644 | −54.170 | 1.00 | 76.76 N |
| ATOM | 1034 | CA | THR | A | 363 | 7.012 | −35.790 | −53.825 | 1.00 | 76.06 C |
| ATOM | 1035 | CB | THR | A | 363 | 7.732 | −37.100 | −54.160 | 1.00 | 77.55 C |
| ATOM | 1036 | OG1 | THR | A | 363 | 8.015 | −37.124 | −55.569 | 1.00 | 79.24 O |
| ATOM | 1037 | CG2 | THR | A | 363 | 6.872 | −38.313 | −53.769 | 1.00 | 80.03 C |
| ATOM | 1038 | C | THR | A | 363 | 6.466 | −35.772 | −52.379 | 1.00 | 81.70 C |
| ATOM | 1039 | O | THR | A | 363 | 5.247 | −35.854 | −52.199 | 1.00 | 91.74 O |
| ATOM | 1040 | N | PRO | A | 364 | 7.347 | −35.644 | −51.353 | 1.00 | 80.43 N |
| ATOM | 1041 | CA | PRO | A | 364 | 6.973 | −35.488 | −49.912 | 1.00 | 74.92 C |
| ATOM | 1042 | CB | PRO | A | 364 | 8.276 | −34.994 | −49.255 | 1.00 | 78.13 C |
| ATOM | 1043 | CG | PRO | A | 364 | 9.317 | −34.957 | −50.336 | 1.00 | 85.76 C |
| ATOM | 1044 | CD | PRO | A | 364 | 8.808 | −35.756 | −51.505 | 1.00 | 85.25 C |
| ATOM | 1045 | C | PRO | A | 364 | 5.850 | −34.487 | −49.617 | 1.00 | 73.29 C |
| ATOM | 1046 | O | PRO | A | 364 | 4.772 | −34.870 | −49.177 | 1.00 | 69.00 O |
| ATOM | 1047 | N | MET | A | 365 | 6.139 | −33.212 | −49.861 | 1.00 | 84.65 N |
| ATOM | 1048 | CA | MET | A | 365 | 5.175 | −32.104 | −49.909 | 1.00 | 88.39 C |
| ATOM | 1049 | CB | MET | A | 365 | 5.897 | −30.899 | −50.532 | 1.00 | 92.97 C |
| ATOM | 1050 | CG | MET | A | 365 | 5.034 | −29.751 | −51.037 | 1.00 | 93.89 C |
| ATOM | 1051 | SD | MET | A | 365 | 4.127 | −28.946 | −49.721 | 1.00 | 103.94 S |
| ATOM | 1052 | CE | MET | A | 365 | 5.482 | −28.425 | −48.662 | 1.00 | 97.87 C |
| ATOM | 1053 | C | MET | A | 365 | 3.833 | −32.397 | −50.633 | 1.00 | 89.73 C |
| ATOM | 1054 | O | MET | A | 365 | 2.819 | −31.709 | −50.395 | 1.00 | 85.51 O |
| ATOM | 1055 | N | PHE | A | 366 | 3.821 | −33.417 | −51.495 | 1.00 | 88.21 N |
| ATOM | 1056 | CA | PHE | A | 366 | 2.597 | −33.808 | −52.212 | 1.00 | 86.77 C |
| ATOM | 1057 | CB | PHE | A | 366 | 2.906 | −34.372 | −53.599 | 1.00 | 90.71 C |
| ATOM | 1058 | CG | PHE | A | 366 | 2.931 | −33.325 | −54.667 | 1.00 | 96.60 C |
| ATOM | 1059 | CD1 | PHE | A | 366 | 1.853 | −32.464 | −54.831 | 1.00 | 90.84 C |
| ATOM | 1060 | CE1 | PHE | A | 366 | 1.883 | −31.489 | −55.808 | 1.00 | 93.74 C |
| ATOM | 1061 | CZ | PHE | A | 366 | 2.987 | −31.366 | −56.640 | 1.00 | 92.51 C |
| ATOM | 1062 | CE2 | PHE | A | 366 | 4.063 | −32.217 | −56.492 | 1.00 | 88.85 C |
| ATOM | 1063 | CD2 | PHE | A | 366 | 4.036 | −33.187 | −55.504 | 1.00 | 97.23 C |
| ATOM | 1064 | C | PHE | A | 366 | 1.704 | −34.768 | −51.458 | 1.00 | 75.40 C |
| ATOM | 1065 | O | PHE | A | 366 | 0.526 | −34.485 | −51.230 | 1.00 | 64.93 O |
| ATOM | 1066 | N | SER | A | 367 | 2.262 | −35.917 | −51.107 | 1.00 | 73.43 N |
| ATOM | 1067 | CA | SER | A | 367 | 1.558 | −36.874 | −50.273 | 1.00 | 73.75 C |
| ATOM | 1068 | CB | SER | A | 367 | 2.481 | −38.002 | −49.827 | 1.00 | 72.74 C |
| ATOM | 1069 | OG | SER | A | 367 | 3.840 | −37.578 | −49.801 | 1.00 | 77.50 O |
| ATOM | 1070 | C | SER | A | 367 | 1.032 | −36.141 | −49.063 | 1.00 | 73.43 C |
| ATOM | 1071 | O | SER | A | 367 | −0.123 | −36.332 | −48.649 | 1.00 | 74.91 O |
| ATOM | 1072 | N | PHE | A | 368 | 1.866 | −35.262 | −48.522 | 1.00 | 66.23 N |
| ATOM | 1073 | CA | PHE | A | 368 | 1.486 | −34.583 | −47.319 | 1.00 | 65.18 C |
| ATOM | 1074 | CB | PHE | A | 368 | 2.628 | −33.757 | −46.767 | 1.00 | 62.36 C |
| ATOM | 1075 | CG | PHE | A | 368 | 2.285 | −33.087 | −45.482 | 1.00 | 58.53 C |
| ATOM | 1076 | CD1 | PHE | A | 368 | 1.981 | −33.844 | −44.354 | 1.00 | 56.95 C |
| ATOM | 1077 | CE1 | PHE | A | 368 | 1.635 | −33.225 | −43.159 | 1.00 | 55.86 C |
| ATOM | 1078 | CZ | PHE | A | 368 | 1.592 | −31.845 | −43.096 | 1.00 | 55.02 C |
| ATOM | 1079 | CE2 | PHE | A | 368 | 1.886 | −31.091 | −44.222 | 1.00 | 52.14 C |
| ATOM | 1080 | CD2 | PHE | A | 368 | 2.217 | −31.708 | −45.405 | 1.00 | 52.50 C |
| ATOM | 1081 | C | PHE | A | 368 | 0.250 | −33.716 | −47.535 | 1.00 | 71.37 C |
| ATOM | 1082 | O | PHE | A | 368 | −0.774 | −33.916 | −46.863 | 1.00 | 68.60 O |
| ATOM | 1083 | N | ALA | A | 369 | 0.347 | −32.774 | −48.479 | 1.00 | 70.98 N |
| ATOM | 1084 | CA | ALA | A | 369 | −0.763 | −31.874 | −48.805 | 1.00 | 70.24 C |
| ATOM | 1085 | CB | ALA | A | 369 | −0.412 | −31.050 | −50.028 | 1.00 | 72.65 C |
| ATOM | 1086 | C | ALA | A | 369 | −2.115 | −32.605 | −48.989 | 1.00 | 66.31 C |
| ATOM | 1087 | O | ALA | A | 369 | −3.079 | −32.359 | −48.254 | 1.00 | 63.23 O |
| ATOM | 1088 | N | LYS | A | 370 | −2.154 | −33.518 | −49.951 | 1.00 | 61.44 N |
| ATOM | 1089 | CA | LYS | A | 370 | −3.300 | −34.375 | −50.201 | 1.00 | 62.54 C |
| ATOM | 1090 | CB | LYS | A | 370 | −2.912 | −35.366 | −51.311 | 1.00 | 67.66 C |
| ATOM | 1091 | CG | LYS | A | 370 | −4.032 | −36.216 | −51.913 | 1.00 | 72.21 C |
| ATOM | 1092 | CD | LYS | A | 370 | −4.388 | −37.412 | −51.028 | 1.00 | 71.57 C |
| ATOM | 1093 | CE | LYS | A | 370 | −5.296 | −38.412 | −51.715 | 1.00 | 68.99 C |
| ATOM | 1094 | NZ | LYS | A | 370 | −6.683 | −37.902 | −51.895 | 1.00 | 71.58 N |
| ATOM | 1095 | C | LYS | A | 370 | −3.822 | −35.090 | −48.924 | 1.00 | 66.68 C |
| ATOM | 1096 | O | LYS | A | 370 | −5.030 | −35.308 | −48.779 | 1.00 | 59.74 O |
| ATOM | 1097 | N | SER | A | 371 | −2.930 | −35.454 | −47.999 | 1.00 | 69.86 N |
| ATOM | 1098 | CA | SER | A | 371 | −3.378 | −36.051 | −46.731 | 1.00 | 68.12 C |
| ATOM | 1099 | CB | SER | A | 371 | −2.270 | −36.840 | −46.054 | 1.00 | 71.30 C |
| ATOM | 1100 | OG | SER | A | 371 | −1.704 | −37.769 | −46.950 | 1.00 | 87.23 O |
| ATOM | 1101 | C | SER | A | 371 | −3.946 | −35.048 | −45.737 | 1.00 | 72.47 C |
| ATOM | 1102 | O | SER | A | 371 | −4.796 | −35.403 | −44.929 | 1.00 | 76.17 O |
| ATOM | 1103 | N | ILE | A | 372 | −3.453 | −33.812 | −45.763 | 1.00 | 73.44 N |
| ATOM | 1104 | CA | ILE | A | 372 | −3.971 | −32.775 | −44.880 | 1.00 | 67.91 C |
| ATOM | 1105 | CB | ILE | A | 372 | −2.946 | −31.618 | −44.674 | 1.00 | 68.64 C |
| ATOM | 1106 | CG1 | ILE | A | 372 | −2.754 | −31.305 | −43.191 | 1.00 | 64.31 C |
| ATOM | 1107 | CD1 | ILE | A | 372 | −1.917 | −32.328 | −42.464 | 1.00 | 63.49 C |
| ATOM | 1108 | CG2 | ILE | A | 372 | −3.352 | −30.344 | −45.414 | 1.00 | 70.98 C |
| ATOM | 1109 | C | ILE | A | 372 | −5.306 | −32.270 | −45.449 | 1.00 | 72.11 C |
| ATOM | 1110 | O | ILE | A | 372 | −6.242 | −31.964 | −44.696 | 1.00 | 71.84 O |
| ATOM | 1111 | N | GLY | A | 373 | −5.386 | −32.181 | −46.779 | 1.00 | 69.44 N |

APPENDIX 1-continued

| | | | | | | | | | |
|---|---|---|---|---|---|---|---|---|---|
| ATOM | 1112 | CA | GLY | A | 373 | −6.621 | −31.788 | −47.447 | 1.00 | 67.40 | C |
| ATOM | 1113 | C | GLY | A | 373 | −7.701 | −32.790 | −47.102 | 1.00 | 66.76 | C |
| ATOM | 1114 | O | GLY | A | 373 | −8.797 | −32.443 | −46.657 | 1.00 | 66.85 | O |
| ATOM | 1115 | N | GLU | A | 374 | −7.350 | −34.055 | −47.256 | 1.00 | 69.53 | N |
| ATOM | 1116 | CA | GLU | A | 374 | −8.238 | −35.146 | −46.928 | 1.00 | 73.06 | C |
| ATOM | 1117 | CB | GLU | A | 374 | −7.481 | −36.475 | −47.014 | 1.00 | 82.42 | C |
| ATOM | 1118 | CG | GLU | A | 374 | −8.356 | −37.689 | −47.287 | 1.00 | 100.77 | C |
| ATOM | 1119 | CD | GLU | A | 374 | −7.854 | −38.946 | −46.586 | 1.00 | 115.64 | C |
| ATOM | 1120 | OE1 | GLU | A | 374 | −8.628 | −39.540 | −45.791 | 1.00 | 111.23 | O |
| ATOM | 1121 | OE2 | GLU | A | 374 | −6.685 | −39.338 | −46.821 | 1.00 | 125.97 | O |
| ATOM | 1122 | C | GLU | A | 374 | −8.814 | −34.965 | −45.540 | 1.00 | 72.67 | C |
| ATOM | 1123 | O | GLU | A | 374 | −9.812 | −35.567 | −45.215 | 1.00 | 81.77 | O |
| ATOM | 1124 | N | LEU | A | 375 | −8.175 | −34.146 | −44.710 | 1.00 | 80.11 | N |
| ATOM | 1125 | CA | LEU | A | 375 | −8.648 | −33.936 | −43.351 | 1.00 | 72.20 | C |
| ATOM | 1126 | CB | LEU | A | 375 | −7.504 | −33.611 | −42.390 | 1.00 | 70.01 | C |
| ATOM | 1127 | CG | LEU | A | 375 | −6.680 | −34.773 | −41.813 | 1.00 | 70.41 | C |
| ATOM | 1128 | CD1 | LEU | A | 375 | −5.608 | −34.283 | −40.859 | 1.00 | 63.13 | C |
| ATOM | 1129 | CD2 | LEU | A | 375 | −7.554 | −35.777 | −41.087 | 1.00 | 69.19 | C |
| ATOM | 1130 | C | LEU | A | 375 | −9.676 | −32.841 | −43.305 | 1.00 | 75.31 | C |
| ATOM | 1131 | O | LEU | A | 375 | −10.358 | −32.694 | −42.303 | 1.00 | 83.28 | O |
| ATOM | 1132 | N | LYS | A | 376 | −9.802 | −32.065 | −44.373 | 1.00 | 70.79 | N |
| ATOM | 1133 | CA | LYS | A | 376 | −10.815 | −31.038 | −44.374 | 1.00 | 79.70 | C |
| ATOM | 1134 | CB | LYS | A | 376 | −12.202 | −31.668 | −44.602 | 1.00 | 87.06 | C |
| ATOM | 1135 | CG | LYS | A | 376 | −12.591 | −31.822 | −46.069 | 1.00 | 96.72 | C |
| ATOM | 1136 | CD | LYS | A | 376 | −13.487 | −33.035 | −46.292 | 1.00 | 100.56 | C |
| ATOM | 1137 | CE | LYS | A | 376 | −13.435 | −33.534 | −47.739 | 1.00 | 106.56 | C |
| ATOM | 1138 | NZ | LYS | A | 376 | −14.322 | −32.797 | −48.693 | 1.00 | 108.43 | N |
| ATOM | 1139 | C | LYS | A | 376 | −10.757 | −30.280 | −43.034 | 1.00 | 79.43 | C |
| ATOM | 1140 | O | LYS | A | 376 | −11.715 | −30.277 | −42.262 | 1.00 | 80.05 | O |
| ATOM | 1141 | N | MET | A | 377 | −9.617 | −29.655 | −42.751 | 1.00 | 80.32 | N |
| ATOM | 1142 | CA | MET | A | 377 | −9.434 | −28.965 | −41.477 | 1.00 | 79.71 | C |
| ATOM | 1143 | CB | MET | A | 377 | −8.079 | −29.320 | −40.826 | 1.00 | 81.73 | C |
| ATOM | 1144 | CG | MET | A | 377 | −6.864 | −29.376 | −41.741 | 1.00 | 88.56 | C |
| ATOM | 1145 | SD | MET | A | 377 | −5.353 | −29.926 | −40.888 | 1.00 | 85.37 | S |
| ATOM | 1146 | CE | MET | A | 377 | −5.157 | −28.629 | −39.663 | 1.00 | 79.81 | C |
| ATOM | 1147 | C | MET | A | 377 | −9.656 | −27.455 | −41.551 | 1.00 | 73.59 | C |
| ATOM | 1148 | O | MET | A | 377 | −9.228 | −26.821 | −42.500 | 1.00 | 79.36 | O |
| ATOM | 1149 | N | THR | A | 378 | −10.331 | −26.890 | −40.547 | 1.00 | 62.12 | N |
| ATOM | 1150 | CA | THR | A | 378 | −10.590 | −25.453 | −40.489 | 1.00 | 62.33 | C |
| ATOM | 1151 | CB | THR | A | 378 | −11.699 | −25.155 | −39.487 | 1.00 | 63.90 | C |
| ATOM | 1152 | OG1 | THR | A | 378 | −11.220 | −25.390 | −38.164 | 1.00 | 65.30 | O |
| ATOM | 1153 | CG2 | THR | A | 378 | −12.883 | −26.059 | −39.747 | 1.00 | 68.86 | C |
| ATOM | 1154 | C | THR | A | 378 | −9.351 | −24.625 | −40.126 | 1.00 | 65.47 | C |
| ATOM | 1155 | O | THR | A | 378 | −8.333 | −25.180 | −39.718 | 1.00 | 70.07 | O |
| ATOM | 1156 | N | GLN | A | 379 | −9.423 | −23.304 | −40.271 | 1.00 | 61.70 | N |
| ATOM | 1157 | CA | GLN | A | 379 | −8.246 | −22.463 | −40.015 | 1.00 | 67.70 | C |
| ATOM | 1158 | CB | GLN | A | 379 | −8.511 | −21.005 | −40.401 | 1.00 | 72.61 | C |
| ATOM | 1159 | CG | GLN | A | 379 | −7.722 | −20.508 | −41.619 | 1.00 | 82.67 | C |
| ATOM | 1160 | CD | GLN | A | 379 | −7.846 | −21.375 | −42.882 | 1.00 | 95.64 | C |
| ATOM | 1161 | OE1 | GLN | A | 379 | −7.177 | −21.108 | −43.885 | 1.00 | 102.19 | O |
| ATOM | 1162 | NE2 | GLN | A | 379 | −8.696 | −22.408 | −42.842 | 1.00 | 99.62 | N |
| ATOM | 1163 | C | GLN | A | 379 | −7.724 | −22.567 | −38.587 | 1.00 | 68.42 | C |
| ATOM | 1164 | O | GLN | A | 379 | −6.520 | −22.623 | −38.342 | 1.00 | 67.20 | O |
| ATOM | 1165 | N | GLU | A | 380 | −8.647 | −22.632 | −37.647 | 1.00 | 70.33 | N |
| ATOM | 1166 | CA | GLU | A | 380 | −8.316 | −22.773 | −36.251 | 1.00 | 69.04 | C |
| ATOM | 1167 | CB | GLU | A | 380 | −9.608 | −22.919 | −35.477 | 1.00 | 74.52 | C |
| ATOM | 1168 | CG | GLU | A | 380 | −10.809 | −22.509 | −36.316 | 1.00 | 88.66 | C |
| ATOM | 1169 | CD | GLU | A | 380 | −12.093 | −22.552 | −35.536 | 1.00 | 98.17 | C |
| ATOM | 1170 | OE1 | GLU | A | 380 | −12.034 | −22.286 | −34.305 | 1.00 | 96.75 | O |
| ATOM | 1171 | OE2 | GLU | A | 380 | −13.142 | −22.852 | −36.158 | 1.00 | 98.26 | O |
| ATOM | 1172 | C | GLU | A | 380 | −7.421 | −23.990 | −36.056 | 1.00 | 67.06 | C |
| ATOM | 1173 | O | GLU | A | 380 | −6.470 | −23.969 | −35.270 | 1.00 | 67.14 | O |
| ATOM | 1174 | N | GLU | A | 381 | −7.722 | −25.043 | −36.806 | 1.00 | 66.66 | N |
| ATOM | 1175 | CA | GLU | A | 381 | −6.959 | −26.278 | −36.765 | 1.00 | 57.00 | C |
| ATOM | 1176 | CB | GLU | A | 381 | −7.761 | −27.408 | −37.429 | 1.00 | 55.47 | C |
| ATOM | 1177 | CG | GLU | A | 381 | −9.098 | −27.651 | −36.722 | 1.00 | 61.50 | C |
| ATOM | 1178 | CD | GLU | A | 381 | −9.982 | −28.762 | −37.310 | 1.00 | 64.99 | C |
| ATOM | 1179 | OE1 | GLU | A | 381 | −9.924 | −29.026 | −38.519 | 1.00 | 69.41 | O |
| ATOM | 1180 | OE2 | GLU | A | 381 | −10.787 | −29.365 | −36.555 | 1.00 | 70.72 | O |
| ATOM | 1181 | C | GLU | A | 381 | −5.588 | −26.047 | −37.404 | 1.00 | 55.03 | C |
| ATOM | 1182 | O | GLU | A | 381 | −4.632 | −26.683 | −37.059 | 1.00 | 56.08 | O |
| ATOM | 1183 | N | TYR | A | 382 | −5.471 | −25.104 | −38.317 | 1.00 | 55.69 | N |
| ATOM | 1184 | CA | TYR | A | 382 | −4.163 | −24.842 | −38.882 | 1.00 | 57.76 | C |
| ATOM | 1185 | CB | TYR | A | 382 | −4.298 | −24.141 | −40.212 | 1.00 | 54.77 | C |
| ATOM | 1186 | CG | TYR | A | 382 | −4.451 | −25.107 | −41.341 | 1.00 | 61.55 | C |
| ATOM | 1187 | CD1 | TYR | A | 382 | −3.366 | −25.845 | −41.804 | 1.00 | 58.62 | C |
| ATOM | 1188 | CE1 | TYR | A | 382 | −3.510 | −26.723 | −42.856 | 1.00 | 61.61 | C |
| ATOM | 1189 | CZ | TYR | A | 382 | −4.749 | −26.877 | −43.455 | 1.00 | 63.50 | C |
| ATOM | 1190 | OH | TYR | A | 382 | −4.929 | −27.752 | −44.519 | 1.00 | 71.14 | O |
| ATOM | 1191 | CE2 | TYR | A | 382 | −5.830 | −26.163 | −43.000 | 1.00 | 60.38 | C |

APPENDIX 1-continued

| ATOM | 1192 | CD2 | TYR | A | 382 | −5.682 | −25.288 | −41.950 | 1.00 | 60.51 | C |
|---|---|---|---|---|---|---|---|---|---|---|---|
| ATOM | 1193 | C | TYR | A | 382 | −3.306 | −24.011 | −37.954 | 1.00 | 61.17 | C |
| ATOM | 1194 | O | TYR | A | 382 | −2.119 | −24.271 | −37.801 | 1.00 | 57.91 | O |
| ATOM | 1195 | N | ALA | A | 383 | −3.915 | −22.993 | −37.358 | 1.00 | 60.41 | N |
| ATOM | 1196 | CA | ALA | A | 383 | −3.258 | −22.222 | −36.335 | 1.00 | 61.02 | C |
| ATOM | 1197 | CB | ALA | A | 383 | −4.193 | −21.149 | −35.810 | 1.00 | 64.92 | C |
| ATOM | 1198 | C | ALA | A | 383 | −2.762 | −23.126 | −35.195 | 1.00 | 61.33 | C |
| ATOM | 1199 | O | ALA | A | 383 | −1.566 | −23.243 | −34.991 | 1.00 | 63.06 | O |
| ATOM | 1200 | N | LEU | A | 384 | −3.658 | −23.788 | −34.473 | 1.00 | 56.90 | N |
| ATOM | 1201 | CA | LEU | A | 384 | −3.233 | −24.535 | −33.291 | 1.00 | 61.52 | C |
| ATOM | 1202 | CB | LEU | A | 384 | −4.409 | −25.217 | −32.610 | 1.00 | 63.43 | C |
| ATOM | 1203 | CG | LEU | A | 384 | −5.701 | −24.453 | −32.390 | 1.00 | 61.80 | C |
| ATOM | 1204 | CD1 | LEU | A | 384 | −6.613 | −25.410 | −31.633 | 1.00 | 65.49 | C |
| ATOM | 1205 | CD2 | LEU | A | 384 | −5.443 | −23.168 | −31.623 | 1.00 | 58.06 | C |
| ATOM | 1206 | C | LEU | A | 384 | −2.190 | −25.592 | −33.602 | 1.00 | 63.01 | C |
| ATOM | 1207 | O | LEU | A | 384 | −1.136 | −25.691 | −32.946 | 1.00 | 67.06 | O |
| ATOM | 1208 | N | LEU | A | 385 | −2.499 | −26.389 | −34.611 | 1.00 | 58.63 | N |
| ATOM | 1209 | CA | LEU | A | 385 | −1.622 | −27.449 | −35.057 | 1.00 | 52.95 | C |
| ATOM | 1210 | CB | LEU | A | 385 | −2.154 | −28.002 | −36.353 | 1.00 | 56.62 | C |
| ATOM | 1211 | CG | LEU | A | 385 | −2.155 | −29.468 | −36.699 | 1.00 | 52.07 | C |
| ATOM | 1212 | CD1 | LEU | A | 385 | −1.113 | −29.643 | −37.792 | 1.00 | 47.35 | C |
| ATOM | 1213 | CD2 | LEU | A | 385 | −1.960 | −30.350 | −35.464 | 1.00 | 52.18 | C |
| ATOM | 1214 | C | LEU | A | 385 | −0.262 | −26.895 | −35.325 | 1.00 | 51.90 | C |
| ATOM | 1215 | O | LEU | A | 385 | 0.665 | −27.648 | −35.421 | 1.00 | 62.42 | O |
| ATOM | 1216 | N | THR | A | 386 | −0.144 | −25.578 | −35.463 | 1.00 | 51.79 | N |
| ATOM | 1217 | CA | THR | A | 386 | 1.127 | −24.949 | −35.788 | 1.00 | 50.01 | C |
| ATOM | 1218 | CB | THR | A | 386 | 0.941 | −23.649 | −36.556 | 1.00 | 48.66 | C |
| ATOM | 1219 | OG1 | THR | A | 386 | 0.256 | −23.916 | −37.786 | 1.00 | 62.76 | O |
| ATOM | 1220 | CG2 | THR | A | 386 | 2.262 | −23.007 | −36.850 | 1.00 | 46.46 | C |
| ATOM | 1221 | C | THR | A | 386 | 1.833 | −24.610 | −34.517 | 1.00 | 56.25 | C |
| ATOM | 1222 | O | THR | A | 386 | 3.063 | −24.810 | −34.414 | 1.00 | 62.43 | O |
| ATOM | 1223 | N | ALA | A | 387 | 1.072 | −24.078 | −33.559 | 1.00 | 51.85 | N |
| ATOM | 1224 | CA | ALA | A | 387 | 1.618 | −23.782 | −32.247 | 1.00 | 51.84 | C |
| ATOM | 1225 | CB | ALA | A | 387 | 0.614 | −23.049 | −31.408 | 1.00 | 54.80 | C |
| ATOM | 1226 | C | ALA | A | 387 | 2.037 | −25.056 | −31.546 | 1.00 | 54.72 | C |
| ATOM | 1227 | O | ALA | A | 387 | 3.071 | −25.078 | −30.874 | 1.00 | 53.97 | O |
| ATOM | 1228 | N | ILE | A | 388 | 1.239 | −26.114 | −31.718 | 1.00 | 52.55 | N |
| ATOM | 1229 | CA | ILE | A | 388 | 1.586 | −27.423 | −31.192 | 1.00 | 49.29 | C |
| ATOM | 1230 | CB | ILE | A | 388 | 0.523 | −28.471 | −31.550 | 1.00 | 48.21 | C |
| ATOM | 1231 | CG1 | ILE | A | 388 | −0.601 | −28.382 | −30.551 | 1.00 | 49.02 | C |
| ATOM | 1232 | CD1 | ILE | A | 388 | −1.940 | −28.678 | −31.179 | 1.00 | 53.80 | C |
| ATOM | 1233 | CG2 | ILE | A | 388 | 1.072 | −29.885 | −31.478 | 1.00 | 46.19 | C |
| ATOM | 1234 | C | ILE | A | 388 | 2.942 | −27.834 | −31.725 | 1.00 | 47.95 | C |
| ATOM | 1235 | O | ILE | A | 388 | 3.756 | −28.403 | −30.984 | 1.00 | 50.26 | O |
| ATOM | 1236 | N | VAL | A | 389 | 3.196 | −27.531 | −32.992 | 1.00 | 44.58 | N |
| ATOM | 1237 | CA | VAL | A | 389 | 4.453 | −27.944 | −33.617 | 1.00 | 48.78 | C |
| ATOM | 1238 | CB | VAL | A | 389 | 4.391 | −27.901 | −35.147 | 1.00 | 49.00 | C |
| ATOM | 1239 | CG1 | VAL | A | 389 | 5.794 | −27.903 | −35.732 | 1.00 | 48.38 | C |
| ATOM | 1240 | CG2 | VAL | A | 389 | 3.648 | −29.122 | −35.636 | 1.00 | 51.92 | C |
| ATOM | 1241 | C | VAL | A | 389 | 5.678 | −27.175 | −33.161 | 1.00 | 50.05 | C |
| ATOM | 1242 | O | VAL | A | 389 | 6.775 | −27.733 | −33.124 | 1.00 | 50.82 | O |
| ATOM | 1243 | N | ILE | A | 390 | 5.515 | −25.892 | −32.852 | 1.00 | 52.16 | N |
| ATOM | 1244 | CA | ILE | A | 390 | 6.654 | −25.117 | −32.394 | 1.00 | 48.94 | C |
| ATOM | 1245 | CB | ILE | A | 390 | 6.393 | −23.604 | −32.437 | 1.00 | 51.15 | C |
| ATOM | 1246 | CG1 | ILE | A | 390 | 6.071 | −23.163 | −33.869 | 1.00 | 54.64 | C |
| ATOM | 1247 | CD1 | ILE | A | 390 | 5.219 | −21.902 | −33.931 | 1.00 | 58.23 | C |
| ATOM | 1248 | CG2 | ILE | A | 390 | 7.571 | −22.837 | −31.860 | 1.00 | 47.19 | C |
| ATOM | 1249 | C | ILE | A | 390 | 6.899 | −25.576 | −30.983 | 1.00 | 42.50 | C |
| ATOM | 1250 | O | ILE | A | 390 | 7.994 | −25.964 | −30.639 | 1.00 | 46.94 | O |
| ATOM | 1251 | N | LEU | A | 391 | 5.852 | −25.577 | −30.193 | 1.00 | 38.46 | N |
| ATOM | 1252 | CA | LEU | A | 391 | 5.965 | −25.865 | −28.783 | 1.00 | 42.84 | C |
| ATOM | 1253 | CB | LEU | A | 391 | 4.714 | −25.393 | −28.078 | 1.00 | 40.16 | C |
| ATOM | 1254 | CG | LEU | A | 391 | 4.791 | −23.881 | −27.828 | 1.00 | 43.05 | C |
| ATOM | 1255 | CD1 | LEU | A | 391 | 3.506 | −23.313 | −27.227 | 1.00 | 42.47 | C |
| ATOM | 1256 | CD2 | LEU | A | 391 | 5.977 | −23.642 | −26.927 | 1.00 | 44.73 | C |
| ATOM | 1257 | C | LEU | A | 391 | 6.156 | −27.322 | −28.459 | 1.00 | 47.29 | C |
| ATOM | 1258 | O | LEU | A | 391 | 5.381 | −27.875 | −27.698 | 1.00 | 52.99 | O |
| ATOM | 1259 | N | SER | A | 392 | 7.192 | −27.935 | −29.010 | 1.00 | 45.21 | N |
| ATOM | 1260 | CA | SER | A | 392 | 7.332 | −29.367 | −28.964 | 1.00 | 47.68 | C |
| ATOM | 1261 | CB | SER | A | 392 | 7.564 | −29.914 | −30.365 | 1.00 | 48.60 | C |
| ATOM | 1262 | OG | SER | A | 392 | 6.391 | −29.720 | −31.150 | 1.00 | 55.97 | O |
| ATOM | 1263 | C | SER | A | 392 | 8.461 | −29.747 | −28.042 | 1.00 | 53.30 | C |
| ATOM | 1264 | O | SER | A | 392 | 9.623 | −29.498 | −28.354 | 1.00 | 59.83 | O |
| ATOM | 1265 | N | PRO | A | 393 | 8.133 | −30.357 | −26.900 | 1.00 | 51.03 | N |
| ATOM | 1266 | CA | PRO | A | 393 | 9.130 | −30.619 | −25.885 | 1.00 | 54.95 | C |
| ATOM | 1267 | CB | PRO | A | 393 | 8.303 | −30.838 | −24.607 | 1.00 | 55.32 | C |
| ATOM | 1268 | CG | PRO | A | 393 | 6.909 | −30.489 | −24.958 | 1.00 | 58.13 | C |
| ATOM | 1269 | CD | PRO | A | 393 | 6.785 | −30.669 | −26.426 | 1.00 | 55.17 | C |
| ATOM | 1270 | C | PRO | A | 393 | 10.078 | −31.786 | −26.147 | 1.00 | 58.89 | C |
| ATOM | 1271 | O | PRO | A | 393 | 10.857 | −32.150 | −25.269 | 1.00 | 62.84 | O |

APPENDIX 1-continued

| | | | | | | | | | | |
|---|---|---|---|---|---|---|---|---|---|---|
| ATOM | 1272 | N    | ASP | A | 394 | 10.048 | −32.355 | −27.339 | 1.00 | 64.81 N |
| ATOM | 1273 | CA   | ASP | A | 394 | 11.028 | −33.373 | −27.667 | 1.00 | 60.13 C |
| ATOM | 1274 | CB   | ASP | A | 394 | 10.326 | −34.689 | −27.986 | 1.00 | 65.44 C |
| ATOM | 1275 | CG   | ASP | A | 394 | 9.454  | −34.600 | −29.216 | 1.00 | 70.53 C |
| ATOM | 1276 | OD1  | ASP | A | 394 | 8.539  | −33.754 | −29.214 | 1.00 | 78.68 O |
| ATOM | 1277 | OD2  | ASP | A | 394 | 9.675  | −35.374 | −30.179 | 1.00 | 69.45 O |
| ATOM | 1278 | C    | ASP | A | 394 | 11.943 | −32.952 | −28.808 | 1.00 | 56.55 C |
| ATOM | 1279 | O    | ASP | A | 394 | 12.413 | −33.794 | −29.546 | 1.00 | 67.78 O |
| ATOM | 1280 | N    | ARG | A | 395 | 12.174 | −31.654 | −28.976 | 1.00 | 52.10 N |
| ATOM | 1281 | CA   | ARG | A | 395 | 13.197 | −31.169 | −29.911 | 1.00 | 52.11 C |
| ATOM | 1282 | CB   | ARG | A | 395 | 13.138 | −29.639 | −30.106 | 1.00 | 48.46 C |
| ATOM | 1283 | CG   | ARG | A | 395 | 11.931 | −29.086 | −30.830 | 1.00 | 47.46 C |
| ATOM | 1284 | CD   | ARG | A | 395 | 11.892 | −29.511 | −32.291 | 1.00 | 48.83 C |
| ATOM | 1285 | NE   | ARG | A | 395 | 10.622 | −29.142 | −32.909 | 1.00 | 59.19 N |
| ATOM | 1286 | CZ   | ARG | A | 395 | 9.976  | −29.882 | −33.810 | 1.00 | 60.59 C |
| ATOM | 1287 | NH1  | ARG | A | 395 | 10.469 | −31.040 | −34.207 | 1.00 | 64.00 N |
| ATOM | 1288 | NH2  | ARG | A | 395 | 8.834  | −29.456 | −34.325 | 1.00 | 62.02 N |
| ATOM | 1289 | C    | ARG | A | 395 | 14.531 | −31.482 | −29.289 | 1.00 | 56.44 C |
| ATOM | 1290 | O    | ARG | A | 395 | 14.673 | −31.395 | −28.059 | 1.00 | 59.21 O |
| ATOM | 1291 | N    | GLN | A | 396 | 15.517 | −31.839 | −30.103 | 1.00 | 61.16 N |
| ATOM | 1292 | CA   | GLN | A | 396 | 16.815 | −32.113 | −29.526 | 1.00 | 76.54 C |
| ATOM | 1293 | CB   | GLN | A | 396 | 17.731 | −32.891 | −30.478 | 1.00 | 80.97 C |
| ATOM | 1294 | CG   | GLN | A | 396 | 18.797 | −32.066 | −31.185 | 1.00 | 93.33 C |
| ATOM | 1295 | CD   | GLN | A | 396 | 19.987 | −32.896 | −31.635 | 1.00 | 103.47 C |
| ATOM | 1296 | OE1  | GLN | A | 396 | 20.066 | −34.103 | −31.362 | 1.00 | 102.37 O |
| ATOM | 1297 | NE2  | GLN | A | 396 | 20.926 | −32.249 | −32.330 | 1.00 | 103.13 N |
| ATOM | 1298 | C    | GLN | A | 396 | 17.381 | −30.767 | −29.104 | 1.00 | 82.16 C |
| ATOM | 1299 | O    | GLN | A | 396 | 17.186 | −29.773 | −29.803 | 1.00 | 84.74 O |
| ATOM | 1300 | N    | TYR | A | 397 | 18.011 | −30.735 | −27.929 | 1.00 | 89.04 N |
| ATOM | 1301 | CA   | TYR | A | 397 | 18.654 | −29.526 | −27.379 | 1.00 | 90.57 C |
| ATOM | 1302 | CB   | TYR | A | 397 | 19.177 | −28.582 | −28.485 | 1.00 | 98.66 C |
| ATOM | 1303 | CG   | TYR | A | 397 | 20.417 | −29.096 | −29.186 | 1.00 | 105.03 C |
| ATOM | 1304 | CD1  | TYR | A | 397 | 21.361 | −29.864 | −28.493 | 1.00 | 110.81 C |
| ATOM | 1305 | CE1  | TYR | A | 397 | 22.508 | −30.341 | −29.118 | 1.00 | 121.22 C |
| ATOM | 1306 | CZ   | TYR | A | 397 | 22.739 | −30.044 | −30.456 | 1.00 | 119.78 C |
| ATOM | 1307 | OH   | TYR | A | 397 | 23.892 | −30.531 | −31.055 | 1.00 | 101.40 O |
| ATOM | 1308 | CE2  | TYR | A | 397 | 21.815 | −29.273 | −31.169 | 1.00 | 121.69 C |
| ATOM | 1309 | CD2  | TYR | A | 397 | 20.662 | −28.804 | −30.533 | 1.00 | 109.75 C |
| ATOM | 1310 | C    | TYR | A | 397 | 17.852 | −28.769 | −26.309 | 1.00 | 82.64 C |
| ATOM | 1311 | O    | TYR | A | 397 | 18.410 | −27.953 | −25.573 | 1.00 | 88.62 O |
| ATOM | 1312 | N    | ILE | A | 398 | 16.561 | −29.055 | −26.197 | 1.00 | 81.15 N |
| ATOM | 1313 | CA   | ILE | A | 398 | 15.767 | −28.549 | −25.065 | 1.00 | 76.03 C |
| ATOM | 1314 | CB   | ILE | A | 398 | 14.305 | −29.011 | −25.139 | 1.00 | 73.57 C |
| ATOM | 1315 | CG1  | ILE | A | 398 | 13.665 | −28.557 | −26.454 | 1.00 | 67.67 C |
| ATOM | 1316 | CD1  | ILE | A | 398 | 13.880 | −27.094 | −26.773 | 1.00 | 68.20 C |
| ATOM | 1317 | CG2  | ILE | A | 398 | 13.533 | −28.530 | −23.915 | 1.00 | 72.57 C |
| ATOM | 1318 | C    | ILE | A | 398 | 16.338 | −29.016 | −23.736 | 1.00 | 65.41 C |
| ATOM | 1319 | O    | ILE | A | 398 | 16.814 | −30.128 | −23.635 | 1.00 | 62.01 O |
| ATOM | 1320 | N    | LYS | A | 399 | 16.302 | −28.146 | −22.738 | 1.00 | 66.74 N |
| ATOM | 1321 | CA   | LYS | A | 399 | 16.827 | −28.454 | −21.412 | 1.00 | 70.30 C |
| ATOM | 1322 | CB   | LYS | A | 399 | 17.733 | −27.317 | −20.915 | 1.00 | 69.27 C |
| ATOM | 1323 | CG   | LYS | A | 399 | 19.083 | −27.237 | −21.625 | 1.00 | 73.08 C |
| ATOM | 1324 | CD   | LYS | A | 399 | 19.920 | −26.044 | −21.176 | 1.00 | 78.10 C |
| ATOM | 1325 | CE   | LYS | A | 399 | 19.149 | −24.728 | −21.303 | 1.00 | 88.41 C |
| ATOM | 1326 | NZ   | LYS | A | 399 | 19.834 | −23.539 | −20.707 | 1.00 | 94.82 N |
| ATOM | 1327 | C    | LYS | A | 399 | 15.691 | −28.697 | −20.421 | 1.00 | 72.45 C |
| ATOM | 1328 | O    | LYS | A | 399 | 15.790 | −29.541 | −19.526 | 1.00 | 76.55 O |
| ATOM | 1329 | N    | ASP | A | 400 | 14.601 | −27.966 | −20.608 | 1.00 | 68.26 N |
| ATOM | 1330 | CA   | ASP | A | 400 | 13.505 | −27.981 | −19.683 | 1.00 | 66.01 C |
| ATOM | 1331 | CB   | ASP | A | 400 | 13.416 | −26.604 | −19.040 | 1.00 | 76.11 C |
| ATOM | 1332 | CG   | ASP | A | 400 | 12.632 | −26.591 | −17.745 | 1.00 | 79.20 C |
| ATOM | 1333 | OD1  | ASP | A | 400 | 11.683 | −27.394 | −17.553 | 1.00 | 89.45 O |
| ATOM | 1334 | OD2  | ASP | A | 400 | 12.956 | −25.717 | −16.927 | 1.00 | 84.83 O |
| ATOM | 1335 | C    | ASP | A | 400 | 12.224 | −28.360 | −20.432 | 1.00 | 65.85 C |
| ATOM | 1336 | O    | ASP | A | 400 | 11.349 | −27.526 | −20.705 | 1.00 | 65.84 O |
| ATOM | 1337 | N    | ARG | A | 401 | 12.124 | −29.647 | −20.746 | 1.00 | 62.84 N |
| ATOM | 1338 | CA   | ARG | A | 401 | 11.024 | −30.177 | −21.527 | 1.00 | 56.25 C |
| ATOM | 1339 | CB   | ARG | A | 401 | 11.244 | −31.659 | −21.801 | 1.00 | 51.53 C |
| ATOM | 1340 | CG   | ARG | A | 401 | 12.606 | −31.870 | −22.407 | 1.00 | 49.85 C |
| ATOM | 1341 | CD   | ARG | A | 401 | 12.819 | −33.222 | −23.054 | 1.00 | 54.50 C |
| ATOM | 1342 | NE   | ARG | A | 401 | 14.171 | −33.264 | −23.604 | 1.00 | 52.60 N |
| ATOM | 1343 | CZ   | ARG | A | 401 | 14.515 | −32.827 | −24.812 | 1.00 | 57.93 C |
| ATOM | 1344 | NH1  | ARG | A | 401 | 13.610 | −32.338 | −25.657 | 1.00 | 64.60 N |
| ATOM | 1345 | NH2  | ARG | A | 401 | 15.775 | −32.887 | −25.193 | 1.00 | 62.34 N |
| ATOM | 1346 | C    | ARG | A | 401 | 9.685  | −29.894 | −20.866 | 1.00 | 56.34 C |
| ATOM | 1347 | O    | ARG | A | 401 | 8.715  | −29.530 | −21.546 | 1.00 | 58.60 O |
| ATOM | 1348 | N    | GLU | A | 402 | 9.630  | −30.019 | −19.548 | 1.00 | 58.98 N |
| ATOM | 1349 | CA   | GLU | A | 402 | 8.370  | −29.778 | −18.857 | 1.00 | 68.93 C |
| ATOM | 1350 | CB   | GLU | A | 402 | 8.327  | −30.361 | −17.431 | 1.00 | 76.65 C |
| ATOM | 1351 | CG   | GLU | A | 402 | 9.327  | −29.776 | −16.442 | 1.00 | 98.71 C |

APPENDIX 1-continued

| ATOM | 1352 | CD  | GLU | A | 402 | 8.807  | −28.531 | −15.729 | 1.00 | 117.03 | C |
|------|------|-----|-----|---|-----|--------|---------|---------|------|--------|---|
| ATOM | 1353 | OE1 | GLU | A | 402 | 9.657  | −27.711 | −15.303 | 1.00 | 121.28 | O |
| ATOM | 1354 | OE2 | GLU | A | 402 | 7.561  | −28.368 | −15.594 | 1.00 | 112.07 | O |
| ATOM | 1355 | C   | GLU | A | 402 | 7.987  | −28.301 | −18.921 | 1.00 | 67.07  | C |
| ATOM | 1356 | O   | GLU | A | 402 | 6.789  | −27.964 | −18.913 | 1.00 | 65.84  | O |
| ATOM | 1357 | N   | ALA | A | 403 | 8.987  | −27.424 | −19.027 | 1.00 | 60.94  | N |
| ATOM | 1358 | CA  | ALA | A | 403 | 8.681  | −26.003 | −19.198 | 1.00 | 61.26  | C |
| ATOM | 1359 | CB  | ALA | A | 403 | 9.936  | −25.171 | −19.160 | 1.00 | 52.63  | C |
| ATOM | 1360 | C   | ALA | A | 403 | 7.909  | −25.803 | −20.511 | 1.00 | 66.74  | C |
| ATOM | 1361 | O   | ALA | A | 403 | 6.930  | −25.021 | −20.562 | 1.00 | 65.40  | O |
| ATOM | 1362 | N   | VAL | A | 404 | 8.327  | −26.554 | −21.544 | 1.00 | 59.50  | N |
| ATOM | 1363 | CA  | VAL | A | 404 | 7.659  | −26.557 | −22.845 | 1.00 | 55.42  | C |
| ATOM | 1364 | CB  | VAL | A | 404 | 8.592  | −27.045 | −23.967 | 1.00 | 53.67  | C |
| ATOM | 1365 | CG1 | VAL | A | 404 | 7.868  | −27.091 | −25.311 | 1.00 | 50.11  | C |
| ATOM | 1366 | CG2 | VAL | A | 404 | 9.816  | −26.144 | −24.050 | 1.00 | 49.09  | C |
| ATOM | 1367 | C   | VAL | A | 404 | 6.345  | −27.345 | −22.830 | 1.00 | 59.48  | C |
| ATOM | 1368 | O   | VAL | A | 404 | 5.345  | −26.892 | −23.399 | 1.00 | 58.36  | O |
| ATOM | 1369 | N   | GLU | A | 405 | 6.323  | −28.503 | −22.167 | 1.00 | 62.42  | N |
| ATOM | 1370 | CA  | GLU | A | 405 | 5.074  | −29.274 | −22.104 | 1.00 | 59.91  | C |
| ATOM | 1371 | CB  | GLU | A | 405 | 5.251  | −30.706 | −21.564 | 1.00 | 61.01  | C |
| ATOM | 1372 | CG  | GLU | A | 405 | 5.175  | −30.877 | −20.069 | 1.00 | 73.57  | C |
| ATOM | 1373 | CD  | GLU | A | 405 | 3.780  | −31.214 | −19.595 | 1.00 | 88.54  | C |
| ATOM | 1374 | OE1 | GLU | A | 405 | 3.283  | −30.581 | −18.629 | 1.00 | 97.08  | O |
| ATOM | 1375 | OE2 | GLU | A | 405 | 3.177  | −32.116 | −20.200 | 1.00 | 99.51  | O |
| ATOM | 1376 | C   | GLU | A | 405 | 3.961  | −28.495 | −21.434 | 1.00 | 55.89  | C |
| ATOM | 1377 | O   | GLU | A | 405 | 2.842  | −28.505 | −21.936 | 1.00 | 52.83  | O |
| ATOM | 1378 | N   | LYS | A | 406 | 4.258  | −27.771 | −20.349 | 1.00 | 57.14  | N |
| ATOM | 1379 | CA  | LYS | A | 406 | 3.202  | −26.934 | −19.733 | 1.00 | 58.73  | C |
| ATOM | 1380 | CB  | LYS | A | 406 | 3.654  | −26.136 | −18.491 | 1.00 | 49.12  | C |
| ATOM | 1381 | C   | LYS | A | 406 | 2.587  | −26.033 | −20.801 | 1.00 | 57.66  | C |
| ATOM | 1382 | O   | LYS | A | 406 | 1.383  | −25.943 | −20.876 | 1.00 | 64.58  | O |
| ATOM | 1383 | N   | LEU | A | 407 | 3.414  | −25.429 | −21.658 | 1.00 | 59.01  | N |
| ATOM | 1384 | CA  | LEU | A | 407 | 2.937  | −24.537 | −22.736 | 1.00 | 56.49  | C |
| ATOM | 1385 | CB  | LEU | A | 407 | 4.093  | −23.745 | −23.327 | 1.00 | 58.83  | C |
| ATOM | 1386 | CG  | LEU | A | 407 | 4.693  | −22.629 | −22.480 | 1.00 | 59.07  | C |
| ATOM | 1387 | CD1 | LEU | A | 407 | 5.710  | −21.851 | −23.303 | 1.00 | 53.56  | C |
| ATOM | 1388 | CD2 | LEU | A | 407 | 3.590  | −21.725 | −21.958 | 1.00 | 55.33  | C |
| ATOM | 1389 | C   | LEU | A | 407 | 2.207  | −25.197 | −23.899 | 1.00 | 56.99  | C |
| ATOM | 1390 | O   | LEU | A | 407 | 1.297  | −24.594 | −24.460 | 1.00 | 60.16  | O |
| ATOM | 1391 | N   | GLN | A | 408 | 2.636  | −26.403 | −24.288 | 1.00 | 55.78  | N |
| ATOM | 1392 | CA  | GLN | A | 408 | 2.014  | −27.149 | −25.390 | 1.00 | 46.25  | C |
| ATOM | 1393 | CB  | GLN | A | 408 | 2.924  | −28.289 | −25.860 | 1.00 | 43.35  | C |
| ATOM | 1394 | CG  | GLN | A | 408 | 2.206  | −29.249 | −26.800 | 1.00 | 50.51  | C |
| ATOM | 1395 | CD  | GLN | A | 408 | 3.100  | −30.243 | −27.499 | 1.00 | 52.91  | C |
| ATOM | 1396 | OE1 | GLN | A | 408 | 3.573  | −31.189 | −26.891 | 1.00 | 57.63  | O |
| ATOM | 1397 | NE2 | GLN | A | 408 | 3.317  | −30.048 | −28.803 | 1.00 | 55.80  | N |
| ATOM | 1398 | C   | GLN | A | 408 | 0.667  | −27.717 | −24.971 | 1.00 | 48.70  | C |
| ATOM | 1399 | O   | GLN | A | 408 | −0.253 | −27.836 | −25.790 | 1.00 | 47.93  | O |
| ATOM | 1400 | N   | GLU | A | 409 | 0.553  | −28.044 | −23.682 | 1.00 | 52.95  | N |
| ATOM | 1401 | CA  | GLU | A | 409 | −0.548 | −28.845 | −23.166 | 1.00 | 55.81  | C |
| ATOM | 1402 | CB  | GLU | A | 409 | −0.383 | −29.020 | −21.679 | 1.00 | 62.24  | C |
| ATOM | 1403 | CG  | GLU | A | 409 | −0.810 | −30.362 | −21.141 | 1.00 | 74.06  | C |
| ATOM | 1404 | CD  | GLU | A | 409 | −0.007 | −30.744 | −19.900 | 1.00 | 89.68  | C |
| ATOM | 1405 | OE1 | GLU | A | 409 | 0.142  | −29.904 | −18.967 | 1.00 | 93.22  | O |
| ATOM | 1406 | OE2 | GLU | A | 409 | 0.486  | −31.893 | −19.860 | 1.00 | 98.84  | O |
| ATOM | 1407 | C   | GLU | A | 409 | −1.903 | −28.218 | −23.461 | 1.00 | 57.56  | C |
| ATOM | 1408 | O   | GLU | A | 409 | −2.726 | −28.841 | −24.145 | 1.00 | 56.45  | O |
| ATOM | 1409 | N   | PRO | A | 410 | −2.122 | −26.963 | −22.986 | 1.00 | 58.17  | N |
| ATOM | 1410 | CA  | PRO | A | 410 | −3.419 | −26.303 | −23.135 | 1.00 | 51.28  | C |
| ATOM | 1411 | CB  | PRO | A | 410 | −3.165 | −24.897 | −22.578 | 1.00 | 46.19  | C |
| ATOM | 1412 | CG  | PRO | A | 410 | −1.962 | −25.040 | −21.687 | 1.00 | 47.71  | C |
| ATOM | 1413 | CD  | PRO | A | 410 | −1.118 | −26.015 | −22.448 | 1.00 | 55.96  | C |
| ATOM | 1414 | C   | PRO | A | 410 | −3.863 | −26.224 | −24.582 | 1.00 | 49.99  | C |
| ATOM | 1415 | O   | PRO | A | 410 | −5.065 | −26.353 | −24.835 | 1.00 | 55.00  | O |
| ATOM | 1416 | N   | LEU | A | 411 | −2.916 | −26.029 | −25.507 | 1.00 | 45.60  | N |
| ATOM | 1417 | CA  | LEU | A | 411 | −3.209 | −25.968 | −26.935 | 1.00 | 48.64  | C |
| ATOM | 1418 | CB  | LEU | A | 411 | −2.012 | −25.438 | −27.710 | 1.00 | 49.55  | C |
| ATOM | 1419 | CG  | LEU | A | 411 | −1.476 | −24.032 | −27.506 | 1.00 | 52.73  | C |
| ATOM | 1420 | CD1 | LEU | A | 411 | −0.033 | −23.982 | −27.984 | 1.00 | 58.81  | C |
| ATOM | 1421 | CD2 | LEU | A | 411 | −2.275 | −23.011 | −28.263 | 1.00 | 49.99  | C |
| ATOM | 1422 | C   | LEU | A | 411 | −3.636 | −27.342 | −27.517 | 1.00 | 53.47  | C |
| ATOM | 1423 | O   | LEU | A | 411 | −4.574 | −27.419 | −28.331 | 1.00 | 50.37  | O |
| ATOM | 1424 | N   | LEU | A | 412 | −2.964 | −28.427 | −27.116 | 1.00 | 52.80  | N |
| ATOM | 1425 | CA  | LEU | A | 412 | −3.510 | −29.774 | −27.391 | 1.00 | 49.51  | C |
| ATOM | 1426 | CB  | LEU | A | 412 | −2.614 | −30.873 | −26.856 | 1.00 | 46.07  | C |
| ATOM | 1427 | CG  | LEU | A | 412 | −1.355 | −31.075 | −27.676 | 1.00 | 47.72  | C |
| ATOM | 1428 | CD1 | LEU | A | 412 | −0.267 | −31.693 | −26.812 | 1.00 | 46.79  | C |
| ATOM | 1429 | CD2 | LEU | A | 412 | −1.636 | −31.879 | −28.938 | 1.00 | 46.85  | C |
| ATOM | 1430 | C   | LEU | A | 412 | −4.901 | −29.950 | −26.804 | 1.00 | 47.38  | C |
| ATOM | 1431 | O   | LEU | A | 412 | −5.797 | −30.467 | −27.465 | 1.00 | 46.89  | O |

APPENDIX 1-continued

| | | | | | | | | | |
|---|---|---|---|---|---|---|---|---|---|
| ATOM | 1432 | N | ASP | A | 413 | −5.080 | −29.491 | −25.572 | 1.00 50.02 N |
| ATOM | 1433 | CA | ASP | A | 413 | −6.387 | −29.555 | −24.925 | 1.00 60.48 C |
| ATOM | 1434 | CB | ASP | A | 413 | −6.325 | −29.039 | −23.484 | 1.00 70.74 C |
| ATOM | 1435 | CG | ASP | A | 413 | −5.833 | −30.111 | −22.478 | 1.00 83.93 C |
| ATOM | 1436 | OD1 | ASP | A | 413 | −4.898 | −30.896 | −22.778 | 1.00 85.17 O |
| ATOM | 1437 | OD2 | ASP | A | 413 | −6.383 | −30.154 | −21.356 | 1.00 100.73 O |
| ATOM | 1438 | C | ASP | A | 413 | −7.505 | −28.884 | −25.741 | 1.00 62.80 C |
| ATOM | 1439 | O | ASP | A | 413 | −8.573 | −29.502 | −25.968 | 1.00 61.06 O |
| ATOM | 1440 | N | VAL | A | 414 | −7.257 | −27.659 | −26.213 | 1.00 58.87 N |
| ATOM | 1441 | CA | VAL | A | 414 | −8.264 | −26.949 | −27.009 | 1.00 59.45 C |
| ATOM | 1442 | CB | VAL | A | 414 | −7.884 | −25.488 | −27.368 | 1.00 60.02 C |
| ATOM | 1443 | CG1 | VAL | A | 414 | −9.076 | −24.792 | −27.968 | 1.00 59.79 C |
| ATOM | 1444 | CG2 | VAL | A | 414 | −7.453 | −24.693 | −26.154 | 1.00 62.81 C |
| ATOM | 1445 | C | VAL | A | 414 | −8.536 | −27.699 | −28.306 | 1.00 58.99 C |
| ATOM | 1446 | O | VAL | A | 414 | −9.680 | −27.788 | −28.743 | 1.00 61.10 O |
| ATOM | 1447 | N | LEU | A | 415 | −7.488 | −28.234 | −28.923 | 1.00 59.50 N |
| ATOM | 1448 | CA | LEU | A | 415 | −7.654 | −28.854 | −30.230 | 1.00 60.81 C |
| ATOM | 1449 | CB | LEU | A | 415 | −6.327 | −29.231 | −30.875 | 1.00 59.84 C |
| ATOM | 1450 | CG | LEU | A | 415 | −6.424 | −29.812 | −32.289 | 1.00 50.72 C |
| ATOM | 1451 | CD1 | LEU | A | 415 | −7.227 | −28.945 | −33.246 | 1.00 48.88 C |
| ATOM | 1452 | CD2 | LEU | A | 415 | −5.014 | −29.949 | −32.783 | 1.00 49.83 C |
| ATOM | 1453 | C | LEU | A | 415 | −8.520 | −30.073 | −30.116 | 1.00 62.84 C |
| ATOM | 1454 | O | LEU | A | 415 | −9.449 | −30.257 | −30.911 | 1.00 68.74 O |
| ATOM | 1455 | N | GLN | A | 416 | −8.233 | −30.899 | −29.119 | 1.00 65.22 N |
| ATOM | 1456 | CA | GLN | A | 416 | −9.096 | −32.043 | −28.855 | 1.00 66.79 C |
| ATOM | 1457 | CB | GLN | A | 416 | −8.706 | −32.762 | −27.571 | 1.00 65.76 C |
| ATOM | 1458 | CG | GLN | A | 416 | −9.459 | −34.062 | −27.355 | 1.00 67.80 C |
| ATOM | 1459 | CD | GLN | A | 416 | −8.674 | −35.018 | −26.484 | 1.00 73.78 C |
| ATOM | 1460 | OE1 | GLN | A | 416 | −8.110 | −34.621 | −25.467 | 1.00 86.43 O |
| ATOM | 1461 | NE2 | GLN | A | 416 | −8.613 | −36.280 | −26.886 | 1.00 76.04 N |
| ATOM | 1462 | C | GLN | A | 416 | −10.565 | −31.604 | −28.855 | 1.00 62.03 C |
| ATOM | 1463 | O | GLN | A | 416 | −11.308 | −32.026 | −29.724 | 1.00 65.46 O |
| ATOM | 1464 | N | LYS | A | 417 | −10.953 | −30.718 | −27.934 | 1.00 61.20 N |
| ATOM | 1465 | CA | LYS | A | 417 | −12.319 | −30.168 | −27.899 | 1.00 57.88 C |
| ATOM | 1466 | CB | LYS | A | 417 | −12.389 | −28.954 | −26.984 | 1.00 56.75 C |
| ATOM | 1467 | CG | LYS | A | 417 | −12.055 | −29.241 | −25.531 | 1.00 58.63 C |
| ATOM | 1468 | CD | LYS | A | 417 | −13.242 | −28.976 | −24.616 | 1.00 59.71 C |
| ATOM | 1469 | CE | LYS | A | 417 | −12.794 | −28.766 | −23.169 | 1.00 62.16 C |
| ATOM | 1470 | NZ | LYS | A | 417 | −13.894 | −28.272 | −22.282 | 1.00 61.95 N |
| ATOM | 1471 | C | LYS | A | 417 | −12.893 | −29.800 | −29.276 | 1.00 54.47 C |
| ATOM | 1472 | O | LYS | A | 417 | −13.982 | −30.284 | −29.639 | 1.00 48.54 O |
| ATOM | 1481 | N | CYS | A | 419 | −12.242 | −30.614 | −32.209 | 1.00 64.55 N |
| ATOM | 1482 | CA | CYS | A | 419 | −12.508 | −31.828 | −32.945 | 1.00 63.36 C |
| ATOM | 1483 | CB | CYS | A | 419 | −11.340 | −32.770 | −32.791 | 1.00 66.64 C |
| ATOM | 1484 | SG | CYS | A | 419 | −9.910 | −32.161 | −33.685 | 1.00 73.04 S |
| ATOM | 1485 | C | CYS | A | 419 | −13.757 | −32.474 | −32.429 | 1.00 66.21 C |
| ATOM | 1486 | O | CYS | A | 419 | −14.667 | −32.754 | −33.194 | 1.00 74.12 O |
| ATOM | 1487 | N | LYS | A | 420 | −13.795 | −32.667 | −31.114 | 1.00 73.78 N |
| ATOM | 1488 | CA | LYS | A | 420 | −14.904 | −33.289 | −30.393 | 1.00 75.38 C |
| ATOM | 1489 | CB | LYS | A | 420 | −14.486 | −33.493 | −28.936 | 1.00 76.69 C |
| ATOM | 1490 | CG | LYS | A | 420 | −15.019 | −34.748 | −28.272 | 1.00 80.41 C |
| ATOM | 1491 | CD | LYS | A | 420 | −14.106 | −35.177 | −27.125 | 1.00 90.64 C |
| ATOM | 1492 | CE | LYS | A | 420 | −14.232 | −36.669 | −26.810 | 1.00 93.41 C |
| ATOM | 1493 | NZ | LYS | A | 420 | −13.202 | −37.105 | −25.823 | 1.00 89.08 N |
| ATOM | 1494 | C | LYS | A | 420 | −16.189 | −32.456 | −30.441 | 1.00 79.70 C |
| ATOM | 1495 | O | LYS | A | 420 | −17.206 | −32.851 | −29.861 | 1.00 85.34 O |
| ATOM | 1496 | N | ILE | A | 421 | −16.136 | −31.308 | −31.119 | 1.00 71.31 N |
| ATOM | 1497 | CA | ILE | A | 421 | −17.297 | −30.446 | −31.276 | 1.00 69.53 C |
| ATOM | 1498 | CB | ILE | A | 421 | −17.021 | −29.028 | −30.730 | 1.00 63.55 C |
| ATOM | 1499 | CG1 | ILE | A | 421 | −17.218 | −29.003 | −29.216 | 1.00 67.12 C |
| ATOM | 1500 | CD1 | ILE | A | 421 | −16.534 | −27.831 | −28.529 | 1.00 72.24 C |
| ATOM | 1501 | CG2 | ILE | A | 421 | −17.906 | −27.987 | −31.396 | 1.00 59.06 C |
| ATOM | 1502 | C | ILE | A | 421 | −17.715 | −30.380 | −32.737 | 1.00 80.37 C |
| ATOM | 1503 | O | ILE | A | 421 | −18.868 | −30.645 | −33.052 | 1.00 92.14 O |
| ATOM | 1504 | N | HIS | A | 422 | −16.764 | −30.039 | −33.611 | 1.00 87.06 N |
| ATOM | 1505 | CA | HIS | A | 422 | −17.006 | −29.738 | −35.032 | 1.00 88.20 C |
| ATOM | 1506 | CB | HIS | A | 422 | −15.856 | −28.894 | −35.581 | 1.00 88.80 C |
| ATOM | 1507 | CG | HIS | A | 422 | −15.994 | −27.408 | −35.325 | 1.00 93.84 C |
| ATOM | 1508 | ND1 | HIS | A | 422 | −15.746 | −26.481 | −36.282 | 1.00 103.34 N |
| ATOM | 1509 | CE1 | HIS | A | 422 | −15.937 | −25.248 | −35.775 | 1.00 96.73 C |
| ATOM | 1510 | NE2 | HIS | A | 422 | −16.311 | −25.383 | −34.487 | 1.00 94.67 N |
| ATOM | 1511 | CD2 | HIS | A | 422 | −16.354 | −26.700 | −34.179 | 1.00 93.11 C |
| ATOM | 1512 | C | HIS | A | 422 | −17.155 | −30.976 | −35.882 | 1.00 87.14 C |
| ATOM | 1513 | O | HIS | A | 422 | −17.463 | −30.890 | −37.071 | 1.00 83.68 O |
| ATOM | 1514 | N | GLN | A | 423 | −16.902 | −32.135 | −35.286 | 1.00 87.95 N |
| ATOM | 1515 | CA | GLN | A | 423 | −17.031 | −33.432 | −35.963 | 1.00 97.55 C |
| ATOM | 1516 | CB | GLN | A | 423 | −15.963 | −33.632 | −37.080 | 1.00 90.40 C |
| ATOM | 1517 | CG | GLN | A | 423 | −14.597 | −32.984 | −36.816 | 1.00 98.93 C |
| ATOM | 1518 | CD | GLN | A | 423 | −13.860 | −32.494 | −38.073 | 1.00 101.26 C |
| ATOM | 1519 | OE1 | GLN | A | 423 | −13.589 | −31.288 | −38.222 | 1.00 91.60 O |

APPENDIX 1-continued

| | | | | | | | | | | |
|---|---|---|---|---|---|---|---|---|---|---|
| ATOM | 1520 | NE2 | GLN | A | 423 | −13.506 | −33.427 | −38.967 | 1.00 | 92.59 N |
| ATOM | 1521 | C | GLN | A | 423 | −17.036 | −34.557 | −34.906 | 1.00 | 100.38 C |
| ATOM | 1522 | O | GLN | A | 423 | −16.002 | −35.197 | −34.661 | 1.00 | 91.43 O |
| ATOM | 1523 | N | PRO | A | 424 | −18.198 | −34.771 | −34.243 | 1.00 | 100.72 N |
| ATOM | 1524 | CA | PRO | A | 424 | −18.288 | −35.854 | −33.264 | 1.00 | 102.59 C |
| ATOM | 1525 | CB | PRO | A | 424 | −19.430 | −35.413 | −32.341 | 1.00 | 93.52 C |
| ATOM | 1526 | CG | PRO | A | 424 | −20.214 | −34.396 | −33.113 | 1.00 | 97.36 C |
| ATOM | 1527 | CD | PRO | A | 424 | −19.477 | −34.048 | −34.379 | 1.00 | 99.11 C |
| ATOM | 1528 | C | PRO | A | 424 | −18.616 | −37.163 | −33.977 | 1.00 | 107.48 C |
| ATOM | 1529 | O | PRO | A | 424 | −18.546 | −38.258 | −33.383 | 1.00 | 99.01 O |
| ATOM | 1530 | N | GLU | A | 425 | −18.948 | −37.033 | −35.259 | 1.00 | 107.88 N |
| ATOM | 1531 | CA | GLU | A | 425 | −19.209 | −38.181 | −36.110 | 1.00 | 115.14 C |
| ATOM | 1532 | CB | GLU | A | 425 | −19.649 | −37.738 | −37.511 | 1.00 | 115.00 C |
| ATOM | 1533 | CG | GLU | A | 425 | −21.035 | −37.087 | −37.553 | 1.00 | 116.54 C |
| ATOM | 1534 | CD | GLU | A | 425 | −21.987 | −37.568 | −36.451 | 1.00 | 113.17 C |
| ATOM | 1535 | OE1 | GLU | A | 425 | −22.635 | −36.709 | −35.819 | 1.00 | 103.23 O |
| ATOM | 1536 | OE2 | GLU | A | 425 | −22.098 | −38.793 | −36.204 | 1.00 | 112.87 O |
| ATOM | 1537 | C | GLU | A | 425 | −18.020 | −39.138 | −36.153 | 1.00 | 109.54 C |
| ATOM | 1538 | O | GLU | A | 425 | −18.173 | −40.334 | −35.895 | 1.00 | 118.69 O |
| ATOM | 1539 | N | ASN | A | 426 | −16.839 | −38.602 | −36.442 | 1.00 | 99.12 N |
| ATOM | 1540 | CA | ASN | A | 426 | −15.620 | −39.397 | −36.413 | 1.00 | 93.27 C |
| ATOM | 1541 | CB | ASN | A | 426 | −14.882 | −39.337 | −37.758 | 1.00 | 95.06 C |
| ATOM | 1542 | CG | ASN | A | 426 | −15.046 | −38.005 | −38.467 | 1.00 | 99.63 C |
| ATOM | 1543 | OD1 | ASN | A | 426 | −15.329 | −37.960 | −39.669 | 1.00 | 101.37 O |
| ATOM | 1544 | ND2 | ASN | A | 426 | −14.856 | −36.913 | −37.733 | 1.00 | 96.63 N |
| ATOM | 1545 | C | ASN | A | 426 | −14.698 | −39.056 | −35.244 | 1.00 | 81.44 C |
| ATOM | 1546 | O | ASN | A | 426 | −13.941 | −38.093 | −35.323 | 1.00 | 80.55 O |
| ATOM | 1547 | N | PRO | A | 427 | −14.737 | −39.878 | −34.170 | 1.00 | 78.48 N |
| ATOM | 1548 | CA | PRO | A | 427 | −13.974 | −39.641 | −32.933 | 1.00 | 73.80 C |
| ATOM | 1549 | CB | PRO | A | 427 | −14.477 | −40.736 | −31.982 | 1.00 | 75.15 C |
| ATOM | 1550 | CG | PRO | A | 427 | −14.900 | −41.839 | −32.894 | 1.00 | 86.15 C |
| ATOM | 1551 | CD | PRO | A | 427 | −15.453 | −41.171 | −34.128 | 1.00 | 80.35 C |
| ATOM | 1552 | C | PRO | A | 427 | −12.490 | −39.802 | −33.105 | 1.00 | 69.45 C |
| ATOM | 1553 | O | PRO | A | 427 | −11.765 | −39.769 | −32.115 | 1.00 | 72.63 O |
| ATOM | 1554 | N | GLN | A | 428 | −12.042 | −39.984 | −34.345 | 1.00 | 75.00 N |
| ATOM | 1555 | CA | GLN | A | 428 | −10.621 | −40.196 | −34.636 | 1.00 | 73.25 C |
| ATOM | 1556 | CB | GLN | A | 428 | −10.379 | −41.553 | −35.296 | 1.00 | 80.26 C |
| ATOM | 1557 | CG | GLN | A | 428 | −10.496 | −41.544 | −36.819 | 1.00 | 78.26 C |
| ATOM | 1558 | CD | GLN | A | 428 | −11.927 | −41.651 | −37.314 | 1.00 | 75.72 C |
| ATOM | 1559 | OE1 | GLN | A | 428 | −12.722 | −42.394 | −36.752 | 1.00 | 70.39 O |
| ATOM | 1560 | NE2 | GLN | A | 428 | −12.252 | −40.927 | −38.387 | 1.00 | 71.60 N |
| ATOM | 1561 | C | GLN | A | 428 | −10.109 | −39.113 | −35.539 | 1.00 | 66.96 C |
| ATOM | 1562 | O | GLN | A | 428 | −9.324 | −39.365 | −36.441 | 1.00 | 72.66 O |
| ATOM | 1563 | N | HIS | A | 429 | −10.551 | −37.894 | −35.295 | 1.00 | 66.17 N |
| ATOM | 1564 | CA | HIS | A | 429 | −10.038 | −36.771 | −36.038 | 1.00 | 64.78 C |
| ATOM | 1565 | CB | HIS | A | 429 | −11.100 | −35.700 | −36.120 | 1.00 | 64.36 C |
| ATOM | 1566 | CG | HIS | A | 429 | −10.805 | −34.643 | −37.131 | 1.00 | 60.62 C |
| ATOM | 1567 | ND1 | HIS | A | 429 | −10.406 | −34.935 | −38.379 | 1.00 | 64.02 N |
| ATOM | 1568 | CE1 | HIS | A | 429 | −10.227 | −33.801 | −39.060 | 1.00 | 69.88 C |
| ATOM | 1569 | NE2 | HIS | A | 429 | −10.526 | −32.774 | −38.242 | 1.00 | 70.69 N |
| ATOM | 1570 | CD2 | HIS | A | 429 | −10.888 | −33.267 | −37.049 | 1.00 | 60.34 C |
| ATOM | 1571 | C | HIS | A | 429 | −8.789 | −36.225 | −35.404 | 1.00 | 63.01 C |
| ATOM | 1572 | O | HIS | A | 429 | −7.789 | −35.934 | −36.101 | 1.00 | 58.11 O |
| ATOM | 1573 | N | PHE | A | 430 | −8.838 | −36.072 | −34.080 | 1.00 | 52.42 N |
| ATOM | 1574 | CA | PHE | A | 430 | −7.743 | −35.432 | −33.358 | 1.00 | 56.65 C |
| ATOM | 1575 | CB | PHE | A | 430 | −8.112 | −35.208 | −31.877 | 1.00 | 53.08 C |
| ATOM | 1576 | CG | PHE | A | 430 | −7.005 | −34.638 | −31.028 | 1.00 | 45.34 C |
| ATOM | 1577 | CD1 | PHE | A | 430 | −6.377 | −33.432 | −31.365 | 1.00 | 46.47 C |
| ATOM | 1578 | CE1 | PHE | A | 430 | −5.362 | −32.913 | −30.569 | 1.00 | 41.31 C |
| ATOM | 1579 | CZ | PHE | A | 430 | −4.978 | −33.597 | −29.416 | 1.00 | 41.25 C |
| ATOM | 1580 | CE2 | PHE | A | 430 | −5.613 | −34.780 | −29.068 | 1.00 | 38.72 C |
| ATOM | 1581 | CD2 | PHE | A | 430 | −6.615 | −35.289 | −29.873 | 1.00 | 40.49 C |
| ATOM | 1582 | C | PHE | A | 430 | −6.517 | −36.301 | −33.553 | 1.00 | 57.09 C |
| ATOM | 1583 | O | PHE | A | 430 | −5.465 | −35.835 | −33.982 | 1.00 | 62.69 O |
| ATOM | 1584 | N | ALA | A | 431 | −6.684 | −37.591 | −33.322 | 1.00 | 63.48 N |
| ATOM | 1585 | CA | ALA | A | 431 | −5.625 | −38.549 | −33.620 | 1.00 | 62.18 C |
| ATOM | 1586 | CB | ALA | A | 431 | −6.153 | −39.960 | −33.433 | 1.00 | 55.42 C |
| ATOM | 1587 | C | ALA | A | 431 | −4.999 | −38.348 | −35.033 | 1.00 | 56.11 C |
| ATOM | 1588 | O | ALA | A | 431 | −3.786 | −38.443 | −35.218 | 1.00 | 49.59 O |
| ATOM | 1589 | N | CYS | A | 432 | −5.810 | −38.035 | −36.028 | 1.00 | 56.05 N |
| ATOM | 1590 | CA | CYS | A | 432 | −5.226 | −37.831 | −37.347 | 1.00 | 59.54 C |
| ATOM | 1591 | CB | CYS | A | 432 | −6.289 | −37.840 | −38.432 | 1.00 | 64.93 C |
| ATOM | 1592 | SG | CYS | A | 432 | −7.009 | −39.472 | −38.697 | 1.00 | 70.90 S |
| ATOM | 1593 | C | CYS | A | 432 | −4.404 | −36.561 | −37.404 | 1.00 | 55.56 C |
| ATOM | 1594 | O | CYS | A | 432 | −3.349 | −36.532 | −38.024 | 1.00 | 59.39 O |
| ATOM | 1595 | N | LEU | A | 433 | −4.866 | −35.516 | −36.736 | 1.00 | 50.72 N |
| ATOM | 1596 | CA | LEU | A | 433 | −4.103 | −34.291 | −36.715 | 1.00 | 47.48 C |
| ATOM | 1597 | CB | LEU | A | 433 | −4.816 | −33.183 | −35.920 | 1.00 | 50.56 C |
| ATOM | 1598 | CG | 1.EU | A | 433 | −6.136 | −32.737 | −36.594 | 1.00 | 46.45 C |
| ATOM | 1599 | CD1 | LEU | A | 433 | −6.989 | −31.822 | −35.741 | 1.00 | 40.50 C |

APPENDIX 1-continued

| ATOM | 1600 | CD2 | LEU | A | 433 | -5.837 | -32.093 | -37.938 | 1.00 | 47.93 | C |
|---|---|---|---|---|---|---|---|---|---|---|---|
| ATOM | 1601 | C | LEU | A | 433 | -2.747 | -34.614 | -36.167 | 1.00 | 43.21 | C |
| ATOM | 1602 | O | LEU | A | 433 | -1.741 | -34.333 | -36.821 | 1.00 | 48.74 | O |
| ATOM | 1603 | N | LEU | A | 434 | -2.708 | -35.253 | -35.009 | 1.00 | 39.41 | N |
| ATOM | 1604 | CA | LEU | A | 434 | -1.411 | -35.670 | -34.439 | 1.00 | 47.95 | C |
| ATOM | 1605 | CB | LEU | A | 434 | -1.572 | -36.447 | -33.129 | 1.00 | 50.42 | C |
| ATOM | 1606 | CG | LEU | A | 434 | -2.021 | -35.611 | -31.919 | 1.00 | 51.41 | C |
| ATOM | 1607 | CD1 | LEU | A | 434 | -1.840 | -36.409 | -30.638 | 1.00 | 52.36 | C |
| ATOM | 1608 | CD2 | LEU | A | 434 | -1.263 | -34.285 | -31.840 | 1.00 | 48.27 | C |
| ATOM | 1609 | C | LEU | A | 434 | -0.596 | -36.486 | -35.412 | 1.00 | 50.07 | C |
| ATOM | 1610 | O | LEU | A | 434 | 0.561 | -36.171 | -35.670 | 1.00 | 55.51 | O |
| ATOM | 1611 | N | GLY | A | 435 | -1.221 | -37.527 | -35.957 | 1.00 | 53.60 | N |
| ATOM | 1612 | CA | GLY | A | 435 | -0.631 | -38.377 | -36.985 | 1.00 | 53.10 | C |
| ATOM | 1613 | C | GLY | A | 435 | 0.151 | -37.674 | -38.073 | 1.00 | 48.76 | C |
| ATOM | 1614 | O | GLY | A | 435 | 1.165 | -38.179 | -38.527 | 1.00 | 52.55 | O |
| ATOM | 1615 | N | ARG | A | 436 | -0.317 | -36.506 | -38.473 | 1.00 | 48.94 | N |
| ATOM | 1616 | CA | ARG | A | 436 | 0.363 | -35.708 | -39.475 | 1.00 | 54.03 | C |
| ATOM | 1617 | CB | ARG | A | 436 | -0.629 | -34.735 | -40.100 | 1.00 | 59.23 | C |
| ATOM | 1618 | CG | ARG | A | 436 | -1.859 | -35.430 | -40.694 | 1.00 | 66.51 | C |
| ATOM | 1619 | CD | ARG | A | 436 | -1.544 | -36.651 | -41.566 | 1.00 | 68.91 | C |
| ATOM | 1620 | NE | ARG | A | 436 | -2.705 | -37.537 | -41.713 | 1.00 | 83.28 | N |
| ATOM | 1621 | CZ | ARG | A | 436 | -2.848 | -38.723 | -41.106 | 1.00 | 102.33 | C |
| ATOM | 1622 | NH1 | ARG | A | 436 | -1.887 | -39.187 | -40.300 | 1.00 | 117.35 | N |
| ATOM | 1623 | NH2 | ARG | A | 436 | -3.948 | -39.461 | -41.307 | 1.00 | 88.32 | N |
| ATOM | 1624 | C | ARG | A | 436 | 1.654 | -35.008 | -39.023 | 1.00 | 57.04 | C |
| ATOM | 1625 | O | ARG | A | 436 | 2.587 | -34.874 | -39.817 | 1.00 | 64.38 | O |
| ATOM | 1626 | N | LEU | A | 437 | 1.732 | -34.567 | -37.766 | 1.00 | 57.29 | N |
| ATOM | 1627 | CA | LEU | A | 437 | 2.990 | -34.020 | -37.219 | 1.00 | 54.51 | C |
| ATOM | 1628 | CB | LEU | A | 437 | 2.867 | -33.643 | -35.743 | 1.00 | 48.04 | C |
| ATOM | 1629 | CG | LEU | A | 437 | 1.580 | -32.888 | -35.373 | 1.00 | 52.90 | C |
| ATOM | 1630 | CD1 | LEU | A | 437 | 1.504 | -32.711 | -33.877 | 1.00 | 49.56 | C |
| ATOM | 1631 | CD2 | LEU | A | 437 | 1.422 | -31.551 | -36.085 | 1.00 | 49.13 | C |
| ATOM | 1632 | C | LEU | A | 437 | 4.134 | -35.001 | -37.379 | 1.00 | 60.72 | C |
| ATOM | 1633 | O | LEU | A | 437 | 5.306 | -34.641 | -37.229 | 1.00 | 74.06 | O |
| ATOM | 1634 | N | THR | A | 438 | 3.796 | -36.245 | -37.682 | 1.00 | 57.18 | N |
| ATOM | 1635 | CA | THR | A | 438 | 4.793 | -37.272 | -37.813 | 1.00 | 53.65 | C |
| ATOM | 1636 | CB | THR | A | 438 | 4.211 | -38.637 | -37.456 | 1.00 | 62.06 | C |
| ATOM | 1637 | OG1 | THR | A | 438 | 3.432 | -38.526 | -36.256 | 1.00 | 64.51 | O |
| ATOM | 1638 | CG2 | THR | A | 438 | 5.311 | -39.603 | -37.190 | 1.00 | 67.52 | C |
| ATOM | 1639 | C | THR | A | 438 | 5.382 | -37.268 | -39.214 | 1.00 | 55.70 | C |
| ATOM | 1640 | O | THR | A | 438 | 6.607 | -37.314 | -39.381 | 1.00 | 62.54 | O |
| ATOM | 1641 | N | GLU | A | 439 | 4.531 | -37.201 | -40.230 | 1.00 | 58.80 | N |
| ATOM | 1642 | CA | GLU | A | 439 | 5.025 | -36.972 | -41.595 | 1.00 | 58.26 | C |
| ATOM | 1643 | CB | GLU | A | 439 | 3.883 | -36.852 | -42.591 | 1.00 | 60.07 | C |
| ATOM | 1644 | CG | GLU | A | 439 | 3.358 | -38.193 | -43.067 | 1.00 | 68.73 | C |
| ATOM | 1645 | CD | GLU | A | 439 | 2.142 | -38.045 | -43.942 | 1.00 | 73.41 | C |
| ATOM | 1646 | OE1 | GLU | A | 439 | 2.305 | -37.861 | -45.186 | 1.00 | 70.86 | O |
| ATOM | 1647 | OE2 | GLU | A | 439 | 1.027 | -38.109 | -43.365 | 1.00 | 73.97 | O |
| ATOM | 1648 | C | GLU | A | 439 | 5.878 | -35.728 | -41.623 | 1.00 | 59.04 | C |
| ATOM | 1649 | O | GLU | A | 439 | 6.817 | -35.646 | -42.406 | 1.00 | 60.59 | O |
| ATOM | 1650 | N | LEU | A | 440 | 5.546 | -34.770 | -40.749 | 1.00 | 63.30 | N |
| ATOM | 1651 | CA | LEU | A | 440 | 6.360 | -33.577 | -40.550 | 1.00 | 65.21 | C |
| ATOM | 1652 | CB | LEU | A | 440 | 5.616 | -32.565 | -39.684 | 1.00 | 66.60 | C |
| ATOM | 1653 | CG | LEU | A | 440 | 4.981 | -31.330 | -40.334 | 1.00 | 64.16 | C |
| ATOM | 1654 | CD1 | LEU | A | 440 | 4.945 | -31.373 | -41.860 | 1.00 | 59.95 | C |
| ATOM | 1655 | CD2 | LEU | A | 440 | 3.592 | -31.107 | -39.749 | 1.00 | 69.64 | C |
| ATOM | 1656 | C | LEU | A | 440 | 7.753 | -33.917 | -40.003 | 1.00 | 65.04 | C |
| ATOM | 1657 | O | LEU | A | 440 | 8.742 | -33.689 | -40.688 | 1.00 | 75.49 | O |
| ATOM | 1658 | N | ARG | A | 441 | 7.837 | -34.514 | -38.816 | 1.00 | 61.14 | N |
| ATOM | 1659 | CA | ARG | A | 441 | 9.137 | -34.940 | -38.286 | 1.00 | 62.28 | C |
| ATOM | 1660 | CB | ARG | A | 441 | 9.016 | -35.823 | -37.043 | 1.00 | 56.38 | C |
| ATOM | 1661 | CG | ARG | A | 441 | 8.140 | -35.244 | -35.961 | 1.00 | 59.09 | C |
| ATOM | 1662 | CD | ARG | A | 441 | 8.701 | -33.998 | -35.295 | 1.00 | 54.25 | C |
| ATOM | 1663 | NE | ARG | A | 441 | 7.984 | -33.868 | -34.036 | 1.00 | 54.02 | N |
| ATOM | 1664 | CZ | ARG | A | 441 | 8.517 | -34.168 | -32.862 | 1.00 | 50.03 | C |
| ATOM | 1665 | NH1 | ARG | A | 441 | 7.804 | -34.096 | -31.765 | 1.00 | 46.11 | N |
| ATOM | 1666 | NH2 | ARG | A | 441 | 9.777 | -34.542 | -32.798 | 1.00 | 55.41 | N |
| ATOM | 1667 | C | ARG | A | 441 | 9.942 | -35.684 | -39.310 | 1.00 | 61.22 | C |
| ATOM | 1668 | O | ARG | A | 441 | 11.156 | -35.543 | -39.364 | 1.00 | 70.19 | O |
| ATOM | 1669 | N | THR | A | 442 | 9.277 | -36.499 | -40.110 | 1.00 | 62.64 | N |
| ATOM | 1670 | CA | THR | A | 442 | 10.004 | -37.257 | -41.119 | 1.00 | 70.69 | C |
| ATOM | 1671 | CB | THR | A | 442 | 9.131 | -38.313 | -41.822 | 1.00 | 71.74 | C |
| ATOM | 1672 | OG1 | THR | A | 442 | 7.764 | -38.112 | -41.455 | 1.00 | 80.59 | O |
| ATOM | 1673 | CG2 | THR | A | 442 | 9.526 | -39.687 | -41.371 | 1.00 | 74.92 | C |
| ATOM | 1674 | C | THR | A | 442 | 10.718 | -36.343 | -42.118 | 1.00 | 67.80 | C |
| ATOM | 1675 | O | THR | A | 442 | 11.923 | -36.466 | -42.280 | 1.00 | 75.79 | O |
| ATOM | 1676 | N | ALA | A | 443 | 10.002 | -35.406 | -42.739 | 1.00 | 61.80 | N |
| ATOM | 1677 | CA | ALA | A | 443 | 10.593 | -34.563 | -43.776 | 1.00 | 65.25 | C |
| ATOM | 1678 | CB | ALA | A | 443 | 9.565 | -33.579 | -44.325 | 1.00 | 72.69 | C |
| ATOM | 1679 | C | ALA | A | 443 | 11.850 | -33.832 | -43.290 | 1.00 | 66.39 | C |

APPENDIX 1-continued

| ATOM | 1680 | O   | ALA | A | 443 | 12.665 | −33.371 | −44.096 | 1.00 | 66.41  | O |
|------|------|-----|-----|---|-----|--------|---------|---------|------|--------|---|
| ATOM | 1681 | N   | ASN | A | 444 | 11.997 | −33.746 | −41.970 | 1.00 | 63.69  | N |
| ATOM | 1682 | CA  | ASN | A | 444 | 13.191 | −33.204 | −41.338 | 1.00 | 63.80  | C |
| ATOM | 1683 | CB  | ASN | A | 444 | 12.952 | −33.003 | −39.837 | 1.00 | 66.70  | C |
| ATOM | 1684 | CG  | ASN | A | 444 | 12.706 | −31.549 | −39.468 | 1.00 | 69.12  | C |
| ATOM | 1685 | OD1 | ASN | A | 444 | 12.919 | −30.642 | −40.267 | 1.00 | 78.39  | O |
| ATOM | 1686 | ND2 | ASN | A | 444 | 12.278 | −31.322 | −38.247 | 1.00 | 72.52  | N |
| ATOM | 1687 | C   | ASN | A | 444 | 14.477 | −33.996 | −41.557 | 1.00 | 65.88  | C |
| ATOM | 1688 | O   | ASN | A | 444 | 15.489 | −33.689 | −40.943 | 1.00 | 71.85  | O |
| ATOM | 1689 | N   | HIS | A | 445 | 14.442 | −35.002 | −42.428 | 1.00 | 74.09  | N |
| ATOM | 1690 | CA  | HIS | A | 445 | 15.634 | −35.760 | −42.777 | 1.00 | 78.71  | C |
| ATOM | 1691 | CB  | HIS | A | 445 | 15.456 | −37.216 | −42.379 | 1.00 | 90.40  | C |
| ATOM | 1692 | CG  | HIS | A | 445 | 14.916 | −38.102 | −43.486 | 1.00 | 99.18  | C |
| ATOM | 1693 | ND1 | HIS | A | 445 | 15.596 | −39.164 | −43.958 | 1.00 | 100.65 | N |
| ATOM | 1694 | CE1 | HIS | A | 445 | 14.882 | −39.752 | −44.937 | 1.00 | 112.37 | C |
| ATOM | 1695 | NE2 | HIS | A | 445 | 13.736 | −39.063 | −45.092 | 1.00 | 105.91 | N |
| ATOM | 1696 | CD2 | HIS | A | 445 | 13.724 | −38.043 | −44.213 | 1.00 | 106.09 | C |
| ATOM | 1697 | C   | HIS | A | 445 | 15.954 | −35.621 | −44.243 | 1.00 | 87.44  | C |
| ATOM | 1698 | O   | HIS | A | 445 | 17.120 | −35.468 | −44.617 | 1.00 | 97.42  | O |
| ATOM | 1699 | N   | HIS | A | 446 | 14.917 | −35.672 | −45.082 | 1.00 | 92.78  | N |
| ATOM | 1700 | CA  | HIS | A | 446 | 15.026 | −35.477 | −46.538 | 1.00 | 95.68  | C |
| ATOM | 1701 | CB  | HIS | A | 446 | 13.779 | −35.991 | −47.248 | 1.00 | 93.64  | C |
| ATOM | 1702 | C   | HIS | A | 446 | 15.252 | −34.034 | −46.898 | 1.00 | 93.63  | C |
| ATOM | 1703 | O   | HIS | A | 446 | 15.743 | −33.731 | −47.980 | 1.00 | 97.93  | O |
| ATOM | 1704 | N   | HIS | A | 447 | 14.848 | −33.135 | −46.004 | 1.00 | 97.08  | N |
| ATOM | 1705 | CA  | HIS | A | 447 | 15.281 | −31.743 | −46.026 | 1.00 | 99.16  | C |
| ATOM | 1706 | CB  | HIS | A | 447 | 14.078 | −30.780 | −45.818 | 1.00 | 100.70 | C |
| ATOM | 1707 | CG  | HIS | A | 447 | 14.336 | −29.293 | −46.174 | 1.00 | 97.57  | C |
| ATOM | 1708 | ND1 | HIS | A | 447 | 15.459 | −28.625 | −45.827 | 1.00 | 100.29 | N |
| ATOM | 1709 | CE1 | HIS | A | 447 | 15.369 | −27.339 | −46.243 | 1.00 | 95.32  | C |
| ATOM | 1710 | NE2 | HIS | A | 447 | 14.172 | −27.170 | −46.830 | 1.00 | 88.39  | N |
| ATOM | 1711 | CD2 | HIS | A | 447 | 13.503 | −28.344 | −46.795 | 1.00 | 97.92  | C |
| ATOM | 1712 | C   | HIS | A | 447 | 16.236 | −31.750 | −44.870 | 1.00 | 96.88  | C |
| ATOM | 1713 | O   | HIS | A | 447 | 16.042 | −31.045 | −43.885 | 1.00 | 102.68 | O |
| ATOM | 1714 | N   | ALA | A | 448 | 17.259 | −32.602 | −44.966 | 1.00 | 100.72 | N |
| ATOM | 1715 | CA  | ALA | A | 448 | 18.356 | −32.646 | −43.988 | 1.00 | 106.39 | C |
| ATOM | 1716 | CB  | ALA | A | 448 | 19.713 | −32.625 | −44.697 | 1.00 | 107.12 | C |
| ATOM | 1717 | C   | ALA | A | 448 | 18.241 | −31.484 | −43.008 | 1.00 | 106.92 | C |
| ATOM | 1718 | O   | ALA | A | 448 | 17.702 | −31.658 | −41.903 | 1.00 | 94.38  | O |
| ATOM | 1719 | N   | GLU | A | 449 | 18.740 | −30.313 | −43.431 | 1.00 | 105.12 | N |
| ATOM | 1720 | CA  | GLU | A | 449 | 18.495 | −29.044 | −42.748 | 1.00 | 100.79 | C |
| ATOM | 1721 | CB  | GLU | A | 449 | 19.456 | −28.884 | −41.554 | 1.00 | 94.59  | C |
| ATOM | 1722 | CG  | GLU | A | 449 | 18.991 | −29.609 | −40.282 | 1.00 | 101.78 | C |
| ATOM | 1723 | CD  | GLU | A | 449 | 19.497 | −29.013 | −38.963 | 1.00 | 109.32 | C |
| ATOM | 1724 | OE1 | GLU | A | 449 | 19.711 | −27.787 | −38.875 | 1.00 | 104.34 | O |
| ATOM | 1725 | OE2 | GLU | A | 449 | 19.658 | −29.780 | −37.983 | 1.00 | 112.57 | O |
| ATOM | 1726 | C   | GLU | A | 449 | 18.505 | −27.813 | −43.702 | 1.00 | 104.05 | C |
| ATOM | 1727 | O   | GLU | A | 449 | 19.300 | −27.761 | −44.649 | 1.00 | 106.57 | O |
| ATOM | 1728 | N   | MET | A | 450 | 17.601 | −26.851 | −43.467 | 1.00 | 89.32  | N |
| ATOM | 1729 | CA  | MET | A | 450 | 17.652 | −25.542 | −44.136 | 1.00 | 93.70  | C |
| ATOM | 1730 | CB  | MET | A | 450 | 16.246 | −25.030 | −44.401 | 1.00 | 94.11  | C |
| ATOM | 1731 | CG  | MET | A | 450 | 16.138 | −23.549 | −44.762 | 1.00 | 91.31  | C |
| ATOM | 1732 | SD  | MET | A | 450 | 14.782 | −22.780 | −43.826 | 1.00 | 99.00  | S |
| ATOM | 1733 | CE  | MET | A | 450 | 14.249 | −21.524 | −44.978 | 1.00 | 104.95 | C |
| ATOM | 1734 | C   | MET | A | 450 | 18.450 | −24.487 | −43.337 | 1.00 | 100.86 | C |
| ATOM | 1735 | O   | MET | A | 450 | 17.912 | −23.428 | −42.955 | 1.00 | 82.40  | O |
| ATOM | 1736 | N   | LEU | A | 451 | 19.730 | −24.771 | −43.077 | 1.00 | 103.14 | N |
| ATOM | 1737 | CA  | LEU | A | 451 | 20.589 | −23.777 | −42.424 | 1.00 | 103.77 | C |
| ATOM | 1738 | CB  | LEU | A | 451 | 21.541 | −24.393 | −41.396 | 1.00 | 89.77  | C |
| ATOM | 1739 | CG  | LEU | A | 451 | 21.120 | −25.506 | −40.441 | 1.00 | 90.84  | C |
| ATOM | 1740 | CD1 | LEU | A | 451 | 19.644 | −25.498 | −40.031 | 1.00 | 73.62  | C |
| ATOM | 1741 | CD2 | LEU | A | 451 | 21.526 | −26.816 | −41.092 | 1.00 | 93.42  | C |
| ATOM | 1742 | C   | LEU | A | 451 | 21.387 | −22.980 | −43.445 | 1.00 | 114.92 | C |
| ATOM | 1743 | O   | LEU | A | 451 | 21.254 | −23.187 | −44.661 | 1.00 | 110.68 | O |
| ATOM | 1744 | N   | MET | A | 452 | 22.218 | −22.074 | −42.923 | 1.00 | 118.46 | N |
| ATOM | 1745 | CA  | MET | A | 452 | 22.966 | −21.100 | −43.717 | 1.00 | 107.65 | C |
| ATOM | 1746 | CB  | MET | A | 452 | 23.969 | −21.799 | −44.644 | 1.00 | 111.30 | C |
| ATOM | 1747 | C   | MET | A | 452 | 22.014 | −20.195 | −44.504 | 1.00 | 106.81 | C |
| ATOM | 1748 | O   | MET | A | 452 | 21.446 | −19.250 | −43.947 | 1.00 | 105.09 | O |
| ATOM | 1749 | N   | SER | A | 453 | 21.819 | −20.527 | −45.782 | 1.00 | 117.80 | N |
| ATOM | 1750 | CA  | SER | A | 453 | 21.102 | −19.685 | −46.761 | 1.00 | 122.52 | C |
| ATOM | 1751 | CB  | SER | A | 453 | 21.692 | −19.920 | −48.162 | 1.00 | 121.72 | C |
| ATOM | 1752 | OG  | SER | A | 453 | 21.628 | −21.284 | −48.553 | 1.00 | 114.02 | O |
| ATOM | 1753 | C   | SER | A | 453 | 19.573 | −19.906 | −46.671 | 1.00 | 118.89 | C |
| ATOM | 1754 | O   | SER | A | 453 | 19.138 | −20.481 | −45.680 | 1.00 | 134.67 | O |
| ATOM | 1755 | N   | TRP | A | 454 | 18.722 | −19.490 | −47.621 | 1.00 | 112.65 | N |
| ATOM | 1756 | CA  | TRP | A | 454 | 18.996 | −18.924 | −48.952 | 1.00 | 109.31 | C |
| ATOM | 1757 | CB  | TRP | A | 454 | 19.733 | −17.581 | −48.892 | 1.00 | 106.13 | C |
| ATOM | 1758 | CG  | TRP | A | 454 | 19.274 | −16.664 | −47.784 | 1.00 | 96.11  | C |
| ATOM | 1759 | CD1 | TRP | A | 454 | 18.169 | −16.823 | −46.956 | 1.00 | 95.92  | C |

APPENDIX 1-continued

| ATOM | 1760 | NE1 | TRP | A | 454 | 18.066 | −15.777 | −46.075 | 1.00 | 105.74 | N |
|---|---|---|---|---|---|---|---|---|---|---|---|
| ATOM | 1761 | CE2 | TRP | A | 454 | 19.048 | −14.869 | −46.281 | 1.00 | 92.90 | C |
| ATOM | 1762 | CD2 | TRP | A | 454 | 19.872 | −15.377 | −47.379 | 1.00 | 89.99 | C |
| ATOM | 1763 | CE3 | TRP | A | 454 | 20.965 | −14.631 | −47.798 | 1.00 | 86.91 | C |
| ATOM | 1764 | CZ3 | TRP | A | 454 | 21.246 | −13.433 | −47.136 | 1.00 | 77.69 | C |
| ATOM | 1765 | CH2 | TRP | A | 454 | 20.454 | −12.970 | −46.072 | 1.00 | 78.50 | C |
| ATOM | 1766 | CZ2 | TRP | A | 454 | 19.332 | −13.667 | −45.637 | 1.00 | 82.13 | C |
| ATOM | 1767 | C | TRP | A | 454 | 19.632 | −19.900 | −49.922 | 1.00 | 108.91 | C |
| ATOM | 1768 | O | TRP | A | 454 | 19.559 | −21.126 | −49.748 | 1.00 | 98.17 | O |
| ATOM | 3485 | O1 | FMT | X | 1 | −2.798 | −41.152 | −25.987 | 1.00 | 53.40 | O |
| ATOM | 3486 | C | FMT | X | 1 | −3.990 | −40.894 | −26.261 | 1.00 | 61.42 | C |
| ATOM | 3487 | O2 | FMT | X | 1 | −4.400 | −40.564 | −27.518 | 1.00 | 65.83 | O |
| ATOM | 3488 | O1 | FMT | X | 2 | −5.245 | −44.027 | −28.469 | 1.00 | 75.04 | O |
| ATOM | 3489 | C | FMT | X | 2 | −4.653 | −43.216 | −29.174 | 1.00 | 70.78 | C |
| ATOM | 3490 | O2 | FMT | X | 2 | −4.592 | −43.444 | −30.483 | 1.00 | 66.32 | O |
| ATOM | 3491 | O1 | FMT | X | 3 | −7.393 | −44.564 | −27.272 | 1.00 | 89.05 | O |
| ATOM | 3492 | C | FMT | X | 3 | −7.419 | −44.851 | −26.079 | 1.00 | 95.81 | C |
| ATOM | 3493 | O2 | FMT | X | 3 | −6.347 | −44.676 | −25.299 | 1.00 | 85.52 | O |
| ATOM | 3494 | O1 | FMT | X | 4 | 0.104 | −43.401 | −27.890 | 1.00 | 83.82 | O |
| ATOM | 3495 | C | FMT | X | 4 | −0.922 | −42.820 | −27.533 | 1.00 | 79.19 | C |
| ATOM | 3496 | O2 | FMT | X | 4 | −1.273 | −41.673 | −28.109 | 1.00 | 73.77 | O |
| ATOM | 3509 | O | HOH | H | 1 | −0.025 | −40.433 | −30.245 | 0.50 | 53.19 | O |
| ATOM | 3511 | O | HOH | H | 2 | 2.383 | −34.329 | −59.541 | 1.00 | 63.63 | O |
| ATOM | 3512 | O | HOH | H | 3 | 17.876 | −8.232 | −45.202 | 1.00 | 50.92 | O |
| ATOM | 3513 | O | HOH | H | 4 | 23.564 | −14.407 | −46.075 | 1.00 | 63.41 | O |
| ATOM | 3514 | O | HOH | H | 5 | −12.464 | −36.958 | −23.418 | 1.00 | 79.65 | O |
| ATOM | 3520 | O | HOH | H | 6 | 20.925 | −11.121 | −41.216 | 1.00 | 53.50 | O |
| ATOM | 3521 | O | HOH | H | 7 | 14.694 | −6.599 | −47.111 | 1.00 | 80.57 | O |
| ATOM | 3522 | O | HOH | H | 8 | 20.186 | −9.607 | −44.541 | 1.00 | 46.88 | O |
| ATOM | 3523 | O | HOH | H | 9 | 18.634 | −22.911 | −51.218 | 1.00 | 56.55 | O |
| ATOM | 3525 | O | HOH | H | 10 | 15.435 | −24.628 | −69.491 | 1.00 | 95.44 | O |
| ATOM | 3526 | O | HOH | H | 11 | 17.275 | −17.501 | −43.269 | 1.00 | 52.94 | O |
| ATOM | 3530 | O | HOH | H | 12 | −8.123 | −38.910 | −21.499 | 1.00 | 72.83 | O |
| ATOM | 3593 | O4 | IVE | F | 1 | 5.562 | −23.549 | −57.435 | 1.00 | 34.73 | O |
| ATOM | 3594 | C30 | IVE | F | 1 | 6.253 | −23.361 | −56.483 | 1.00 | 42.27 | C |
| ATOM | 3595 | C25 | IVE | F | 1 | 6.851 | −22.035 | −56.366 | 1.00 | 41.94 | C |
| ATOM | 3596 | C24 | IVE | F | 1 | 5.830 | −21.162 | −57.036 | 1.00 | 45.13 | C |
| ATOM | 3597 | O6 | IVE | F | 1 | 5.960 | −19.849 | −56.530 | 1.00 | 48.25 | O |
| ATOM | 3598 | C23 | IVE | F | 1 | 5.888 | −21.173 | −58.561 | 1.00 | 41.83 | C |
| ATOM | 3599 | C28 | IVE | F | 1 | 6.497 | −22.395 | −59.183 | 1.00 | 42.70 | C |
| ATOM | 3600 | O3 | IVE | F | 1 | 6.887 | −22.052 | −60.508 | 1.00 | 44.36 | O |
| ATOM | 3601 | C27 | IVE | F | 1 | 7.588 | −22.876 | −58.287 | 1.00 | 46.83 | C |
| ATOM | 3602 | C29 | IVE | F | 1 | 8.178 | −24.237 | −58.349 | 1.00 | 42.29 | C |
| ATOM | 3603 | C26 | IVE | F | 1 | 7.967 | −22.092 | −57.317 | 1.00 | 42.50 | C |
| ATOM | 3604 | C21 | IVE | F | 1 | 4.454 | −21.635 | −56.814 | 1.00 | 47.17 | C |
| ATOM | 3605 | C22 | IVE | F | 1 | 3.880 | −22.126 | −58.097 | 1.00 | 48.41 | C |
| ATOM | 3606 | O2 | IVE | F | 1 | 4.564 | −21.300 | −59.018 | 1.00 | 48.52 | O |
| ATOM | 3607 | C20 | IVE | F | 1 | 3.737 | −21.615 | −55.680 | 1.00 | 52.89 | C |
| ATOM | 3608 | C19 | IVE | F | 1 | 4.066 | −21.170 | −54.329 | 1.00 | 52.54 | C |
| ATOM | 3609 | C18 | IVE | F | 1 | 3.070 | −21.492 | −53.519 | 1.00 | 50.84 | C |
| ATOM | 3610 | C17 | IVE | F | 1 | 2.811 | −21.291 | −52.048 | 1.00 | 46.67 | C |
| ATOM | 3611 | C31 | IVE | F | 1 | 1.920 | −22.423 | −51.587 | 1.00 | 44.91 | C |
| ATOM | 3612 | C16 | IVE | F | 1 | 3.931 | −21.428 | −51.088 | 1.00 | 45.07 | C |
| ATOM | 3613 | C15 | IVE | F | 1 | 4.453 | −22.798 | −51.161 | 1.00 | 43.49 | C |
| ATOM | 3614 | C46 | IVE | F | 1 | 5.807 | −23.099 | −50.643 | 1.00 | 47.11 | C |
| ATOM | 3615 | C14 | IVE | F | 1 | 3.759 | −23.799 | −51.649 | 1.00 | 34.92 | C |
| ATOM | 3616 | C13 | IVE | F | 1 | 4.490 | −25.104 | −51.616 | 1.00 | 40.02 | C |
| ATOM | 3617 | C12 | IVE | F | 1 | 5.892 | −24.866 | −52.109 | 1.00 | 40.15 | C |
| ATOM | 3618 | O1 | IVE | F | 1 | 6.440 | −26.057 | −52.591 | 1.00 | 41.50 | O |
| ATOM | 3619 | C8 | IVE | F | 1 | 7.794 | −25.799 | −52.731 | 1.00 | 41.58 | C |
| ATOM | 3620 | O | IVE | F | 1 | 8.512 | −26.984 | −52.915 | 1.00 | 42.09 | O |
| ATOM | 3621 | C4 | IVE | F | 1 | 9.767 | −26.790 | −52.353 | 1.00 | 38.79 | C |
| ATOM | 3622 | C2 | IVE | F | 1 | 9.368 | −26.942 | −50.936 | 1.00 | 35.80 | C |
| ATOM | 3623 | C1 | IVE | F | 1 | 10.587 | −27.145 | −50.096 | 1.00 | 40.97 | C |
| ATOM | 3624 | C | IVE | F | 1 | 11.476 | −25.994 | −50.449 | 1.00 | 42.24 | C |
| ATOM | 3625 | C3 | IVE | F | 1 | 8.424 | −28.113 | −50.913 | 1.00 | 39.75 | C |
| ATOM | 3626 | C5 | IVE | F | 1 | 10.204 | −25.374 | −52.596 | 1.00 | 35.48 | C |
| ATOM | 3627 | C47 | IVE | F | 1 | 11.705 | −25.188 | −52.585 | 1.00 | 36.77 | C |
| ATOM | 3628 | C6 | IVE | F | 1 | 9.586 | −24.572 | −51.505 | 1.00 | 38.03 | C |
| ATOM | 3629 | C7 | IVE | F | 1 | 8.164 | −25.062 | −51.471 | 1.00 | 36.96 | C |
| ATOM | 3630 | C9 | IVE | F | 1 | 8.027 | −24.961 | −53.950 | 1.00 | 42.04 | C |
| ATOM | 3631 | C11 | IVE | F | 1 | 5.784 | −23.950 | −53.301 | 1.00 | 43.98 | C |
| ATOM | 3632 | C10 | IVE | F | 1 | 6.927 | −23.989 | −54.303 | 1.00 | 48.72 | C |
| ATOM | 3633 | O5 | IVE | F | 1 | 6.450 | −24.416 | −55.545 | 1.00 | 45.48 | O |
| ATOM | 3634 | O7 | IVE | F | 1 | 3.180 | −21.459 | −49.920 | 1.00 | 44.35 | O |
| ATOM | 3635 | C32 | IVE | F | 1 | 3.919 | −20.960 | −48.865 | 1.00 | 44.67 | C |
| ATOM | 3636 | C33 | IVE | F | 1 | 5.400 | −20.975 | −48.789 | 1.00 | 36.88 | C |
| ATOM | 3637 | C34 | IVE | F | 1 | 5.557 | −19.975 | −47.667 | 1.00 | 47.38 | C |
| ATOM | 3638 | O13 | IVE | F | 1 | 6.818 | −19.417 | −47.765 | 1.00 | 48.17 | O |
| ATOM | 3639 | C45 | IVE | F | 1 | 7.570 | −20.231 | −48.627 | 1.00 | 54.34 | C |

APPENDIX 1-continued

| ATOM | 3640 | C35 | IVE | F | 1 | 4.576 | −18.865 | −47.897 | 1.00 | 46.83 | C |
|---|---|---|---|---|---|---|---|---|---|---|---|
| ATOM | 3641 | C36 | IVE | F | 1 | 3.445 | −19.589 | −48.449 | 1.00 | 40.88 | C |
| ATOM | 3642 | C37 | IVE | F | 1 | 2.045 | −19.107 | −48.138 | 1.00 | 37.66 | C |
| ATOM | 3643 | O8 | IVE | F | 1 | 3.367 | −20.712 | −47.614 | 1.00 | 45.84 | O |
| ATOM | 3644 | O9 | IVE | F | 1 | 4.079 | −18.406 | −46.691 | 1.00 | 56.29 | O |
| ATOM | 3645 | C38 | IVE | F | 1 | 5.114 | −17.919 | −45.898 | 1.00 | 44.61 | C |
| ATOM | 3646 | C39 | IVE | F | 1 | 4.492 | −16.762 | −45.173 | 1.00 | 42.48 | C |
| ATOM | 3647 | C40 | IVE | F | 1 | 4.874 | −15.387 | −45.689 | 1.00 | 50.96 | C |
| ATOM | 3648 | O12 | IVE | F | 1 | 3.737 | −14.578 | −45.832 | 1.00 | 55.04 | O |
| ATOM | 3649 | C44 | IVE | F | 1 | 4.181 | −13.391 | −46.446 | 1.00 | 58.46 | C |
| ATOM | 3650 | C41 | IVE | F | 1 | 5.504 | −15.371 | −47.042 | 1.00 | 49.52 | C |
| ATOM | 3651 | O11 | IVE | F | 1 | 6.895 | −15.337 | −46.846 | 1.00 | 44.10 | O |
| ATOM | 3652 | C42 | IVE | F | 1 | 5.266 | −16.684 | −47.674 | 1.00 | 54.85 | C |
| ATOM | 3653 | O10 | IVE | F | 1 | 6.039 | −17.467 | −46.827 | 1.00 | 39.32 | O |
| ATOM | 3654 | C43 | IVE | F | 1 | 5.796 | −16.638 | −49.094 | 1.00 | 59.34 | C |
| END. | | | | | | | | | | | |

The invention claimed is:

1. A method of treating a Farnesoid X receptor mediated disease, the method comprising:
   administering to a patient a composition comprising ivermectin or a pharmaceutically acceptable salt thereof and a pharmaceutically acceptable excipient, wherein the Farnesoid X receptor mediated disease is non-alcoholic fatty liver disease.

2. A method of treating a Farnesoid X receptor mediated disease, the method comprising:
   administering to a patient a composition comprising avermectin or a pharmaceutically acceptable salt thereof and a pharmaceutically acceptable excipient, wherein the Farnesoid X receptor mediated disease is non-alcoholic fatty liver disease.

3. A method of treating a Farnesoid X receptor mediated disease, the method comprising:
   administering to a patient a composition comprising doramectin or a pharmaceutically acceptable salt thereof and a pharmaceutically acceptable excipient, wherein the Farnesoid X receptor mediated disease is non-alcoholic fatty liver disease.

* * * * *